US012788985B2

(12) United States Patent
Minar et al.

(10) Patent No.: US 12,788,985 B2
(45) Date of Patent: Nov. 10, 2026

(54) METHOD AND DEVICE TO ENHANCE WASTE CLEARANCE IN THE BRAIN

(71) Applicant: Neuraworx Medical Technologies, Inc., Excelsior, MN (US)

(72) Inventors: Chris Minar, Excelsior, MN (US); Kip Allan Ludwig, Middleton, WI (US); Justin Williams, Cambridge, WI (US)

( * ) Notice: Subject to any disclaimer, the term of this patent is extended or adjusted under 35 U.S.C. 154(b) by 478 days.

(21) Appl. No.: 17/965,747

(22) Filed: Oct. 13, 2022

(65) Prior Publication Data

US 2023/0233858 A1 Jul. 27, 2023

Related U.S. Application Data

(60) Provisional application No. 63/302,609, filed on Jan. 25, 2022.

(51) Int. Cl.
*A61N 1/36* (2006.01)
*A61N 1/04* (2006.01)
*A61N 1/05* (2006.01)
*A61N 1/372* (2006.01)

(52) U.S. Cl.
CPC ......... *A61N 1/3606* (2013.01); *A61N 1/0484* (2013.01); *A61N 1/0548* (2013.01); *A61N 1/36025* (2013.01); *A61N 1/36031* (2017.08); *A61N 1/36034* (2017.08); *A61N 1/36135* (2013.01); *A61N 1/36153* (2013.01); *A61N 1/36157* (2013.01); *A61N 1/36178* (2013.01); *A61N 1/37223* (2013.01)

(58) Field of Classification Search
CPC ............ A61N 1/36025; A61N 1/36031; A61N 1/36034; A61N 1/36135; A61N 1/36153; A61N 1/36157; A61N 1/0529
See application file for complete search history.

(56) References Cited

U.S. PATENT DOCUMENTS

2021/0338973 A1* 11/2021 Poltorak .............. G06V 10/764
2022/0266015 A1* 8/2022 Simon ................ A61N 1/36034

FOREIGN PATENT DOCUMENTS

AU 2015202180 A1 * 5/2015
EP 3337557 B1 * 8/2020 ......... A61N 1/37211
WO WO-2005051329 A2 * 6/2005 ............. A61B 5/682

* cited by examiner

*Primary Examiner* — Carl H Layno
*Assistant Examiner* — Maria Catherine Anthony
(74) *Attorney, Agent, or Firm* — John M Berns

(57) ABSTRACT

Medical devices and methods of medical treatment for the electrical stimulation of target nerves to enhance waste clearance in the brain for treating neurological disorders such as Alzheimer's disease (AD), including prodromal, mild cognitive impairment (MCI) and early stage Alzheimer's disease.

18 Claims, 18 Drawing Sheets

METHOD AND DEVICE TO ENHANCE WASTE CLEARANCE IN THE BRAIN

BACKGROUND OF THE INVENTION

Field of the Invention

The invention relates to medical devices and methods of medical treatment for the electrical stimulation of target nerves to enhance waste clearance in the brain for treating neurological disorders such as Alzheimer's disease (AD), including prodromal, mild cognitive impairment (MCI) and early stage Alzheimer's disease.

Background Art

There are more than six million cases of AD each year in the United States. Alzheimer's is a progressive neurodegenerative disease that destroys memory and other brain functions and presents a significant problem to the aging population. Neurodegenerative diseases advance with increasing loss of neuronal cell connections, neuronal cell death and progressive symptoms including memory loss and loss of cognitive function. As the disease advances, symptoms can include problems with language, disorientation, behavioral changes and loss of independent function. In developed countries AD is one of the most financially costly diseases. At present, no cure exists, but medications and management strategies may temporarily improve symptoms and reduce the speed of cognitive decline. The story is similar for Parkinson's disease, small vessel disease, and other forms of dementia.

The large body of evidence connecting toxic protein metabolites such as amyloid-β (Aβ) and tau sub-species to the cognitive decline in late-stage AD has to date led scientists to pursue pharmacological strategies to reduce Aβ or tau burden in the brain. Their aim is to slow or reverse the course of the disease; yet, clinical trials to address Aβ or tau have been largely unsuccessful in ameliorating cognitive deficits, despite imaging studies demonstrating a clear reduction in at least Aβ burden in the therapeutic arm.

Retrospective studies of subjects who eventually go on to exhibit cognitive deficits due to AD show that these subjects exhibit decreases in cerebral blood flow (CBF) and reduced brain metabolism years or even decades before the deposition of toxic forms of Aβ or tau are evident. This reduction in CBF is also critically important in the context of the recently discovered clearance systems of the brain, the glymphatic system and the meningeal lymphatic systems. Brain waste clearance is facilitated by the interchange of cerebrospinal fluid (CSF) and interstitial fluid (ISF) in a process dependent on the astrocytic membrane water channel aquaporin-4 (AQP4) lining the glia limitans (hence the term 'glymphatic'). CSF flows in the perivascular space (PVS) surrounding an artery or descending arteriole. Arterial dilation alters the size of the surrounding perivascular space, with the natural pulsatility of the artery acting as a peristaltic pump to drive CSF in the associated paravascular space and facilitate CSF-ISF. Consequently, the reduced CBF at the prodromal stages of AD ultimately also reduces metabolite clearance function that naturally occurs during sleep.

These data in aggregate suggest that prodromal AD patients experience a decrease in CBF, a reduction in brain metabolism, and a deficit in clearance of metabolic waste that not only impacts the accumulation of Aβ and tau, but the concentration of other bioactive extracellular waste molecules such as lactate and the concentration of neurochemical transmitters. These newer players have recently received increased attention, and putatively contribute to reported neural hyperactivity, synaptic dysfunction and neuronal loss function years prior to stereotypical Aβ plaques or tau tangles becoming evident. Given the redundant function within the brain, even AD patients with only mild cognitive impairments likely experience extensive synaptic and neuronal dysfunction before cognitive impairments are evident or degeneration is detectable via non-invasive imaging.

Several working theories for the root cause of Alzheimer's and other Dementias are under investigation. At present there is no consensus on the cause of the disease or how to treat it. The potential cause may be a lack of blood flow, reduced metabolism, the buildup of toxins in the brain, a combination of these, or something else related to the root cause of these.

Neural activity in the brain is dramatically increased during the day. Similar to exercise, this increased neural activity causes the accumulation of byproducts of increased metabolic demand including small molecule metabolites that interfere with learning, memory, alertness and concentration. In addition, concentrations of neurotransmitters and stress hormones within the brain increase. Sleep is a human body's way to remove the unwanted toxic byproducts of increased activity during the day. Recent discoveries of the glymphatic and meningeal lymphatic clearance system within the brain—which act preferentially during sleep—represent a paradigm shift in understanding the restorative function of sleep.

The brain is immersed in cerebral spinal fluid (CSF), which travels along perivascular spaces around descending arterioles and into the deep tissue of the brain (parenchyma). The perivascular space around these arterioles is defined by astrocytic end-feet which have channels in them through which CSF can pass, known as AQP4 channels. As the arteries pulse they drive the CSF in the associated perivascular space like a peristaltic pump through these AQP4 channels and into the deep tissues of the brain. Throughout during the day AQP4 channels are predominantly closed, but preferentially open during slow wave sleep to allow the flow of CSF into the parenchyma. This flow of CSF through the extracellular space drives metabolic waste products towards passive and active transport locations at the venous system where they are cleared from the brain.

Blood flow and CSF flow are influenced by several factors while we are awake and while we sleep. Evidence suggest that CSF flow in the human brain increases during sleep, and is influenced by cardiovascular, respiratory and vasomotor pulsations.

The nutrient delivery and waste clearance system of the brain and the eyes has profound implications for the management of misfolded proteins such as β-amyloid, α-synuclein, and p-tau within the brain. If left unaddressed these misfolded proteins aggregate to create plaques and inclusions in the brain where they begin to cause neurodegeneration and ultimately lead to Alzheimer's Disease and Parkinson's disease. These aggregates of misfolded proteins also trigger the immune response within the brain, causing chronic inflammation and the buildup of vascular plaques which inhibit brain clearance, both of which lead to further neurodegeneration in a vicious slippery-slope cycle. Recent drug studies in patients with severe Alzheimer's Disease have shown that reducing amyloid load after widespread brain inflammation and severe neurodegeneration have occurred does not positively impact neurocognitive deficits of late state Alzheimer's Disease and current anti-amyloid therapies have a significant risk of cerebral edema and microhemorrhage. See e.g., *Disease-modifying drugs for Alzheimer's: hope or hype? New Alzheimer's drugs are now in clinical trials. Experts advise cautious optimism.* Hary Ment Health Lett, 2007. 24(4): p. 1-3. The data have led many to suggest we must intervene much earlier in the disease process, to prevent misfolded proteins from every reaching the 'tipping point' initiating this unrecoverable sequence of events.

Thus, there is a need for an early acting medical device that is readily usable by a patient to restore natural blood flow and CSF flow, to improve the balance of healthy molecules and with a lower risk profile than pharmacologic therapies. Ideally the device should be capable of function at anytime, but especially tailored to function at night while the patient sleeps, and ideally be capable of treatment without active intervention from the patient.

BRIEF SUMMARY OF THE INVENTION

The present invention solves these needs by providing a stimulation system for changing cerebral spinal fluid flow rates through the brain. The system includes a stimulator with a first electrode designed to stimulate a nerve, a modulator system designed to provide a stimulation wave to the first electrode, a power controller designed to control the power of the stimulation wave to the first electrode, a communications module designed to receive instructions executable by one of the stimulator, the modulator system, or the power controller to change the stimulation wave, a remote device that includes a processor and a memory coupled to the processor, the memory comprising computer readable instructions executable by the processor, the processor operable when executing the instructions to send instructions to the communications module to change the stimulation wave.

The remote device can include a wireless communication module designed to wirelessly communicate with the communications module in the stimulator. The stimulator can include a second electrode, and the remote device can be designed to provide a different wave to each electrode.

In one embodiment the stimulator further comprises a second electrode, and wherein the remote device is designed to determine which electrode to stimulate. In another, the power controller is designed to control the voltage or the current to the electrode.

In one embodiment the stimulation wave is a temporally patterned short higher frequency burst. In another, the stimulation wave is designed to cause pulsations of vessel dilation and contraction. In another, the stimulation wave is designed to open APQ4 channels. In another, the stimulation wave is designed to increase the distance between neuronal/non-neuronal cells to allow more flow around these cells.

In one embodiment the stimulation wave is designed to increase phagocytic activity in glial cells. In another embodiment, the stimulation wave is designed to reduce central sympathetic tone.

In another embodiment, the stimulation wave has a predetermined periodicity providing a first period of stimulation of the perivascular system and a second period of relaxation of the perivascular system. In one embodiment the stimulator further comprises a sleep sensor, or can comprise a respiratory sensor.

The stimulator can be a mouthpiece. The mouthpiece can include first and second electrodes, a power supply, and a stimulator circuit. The power supply can be a battery. The system can include a charging station designed to hold the stimulator and recharge the battery.

In another embodiment the stimulation system for changing cerebral spinal fluid flow rates through the brain includes a stimulator designed to stimulate a nerve, a modulator designed to provide a stimulation wave form to the stimulator, a power controller designed to control the power of the stimulation wave to the stimulator, a communications module designed to receive instructions executable by one of the stimulator, the modulator system, or the power controller to change the stimulation wave, a remote device that includes a processor, a memory coupled to the processor, the memory comprising computer readable instructions executable by the processors, the processors operable when executing the instructions to send instructions to the communications module to change the stimulation wave, and a remote device cloud module designed to upload data to a cloud based memory.

Another embodiment is a stimulation method for changing cerebral spinal fluid flow rates through the brain that includes the steps of stimulating a nerve, modulating the stimulation, controlling the power of the stimulation, and communicating stimulation instructions between a remote device and the stimulator.

DETAILED DESCRIPTION OF THE PREFERRED EMBODIMENTS

Figure 1A:
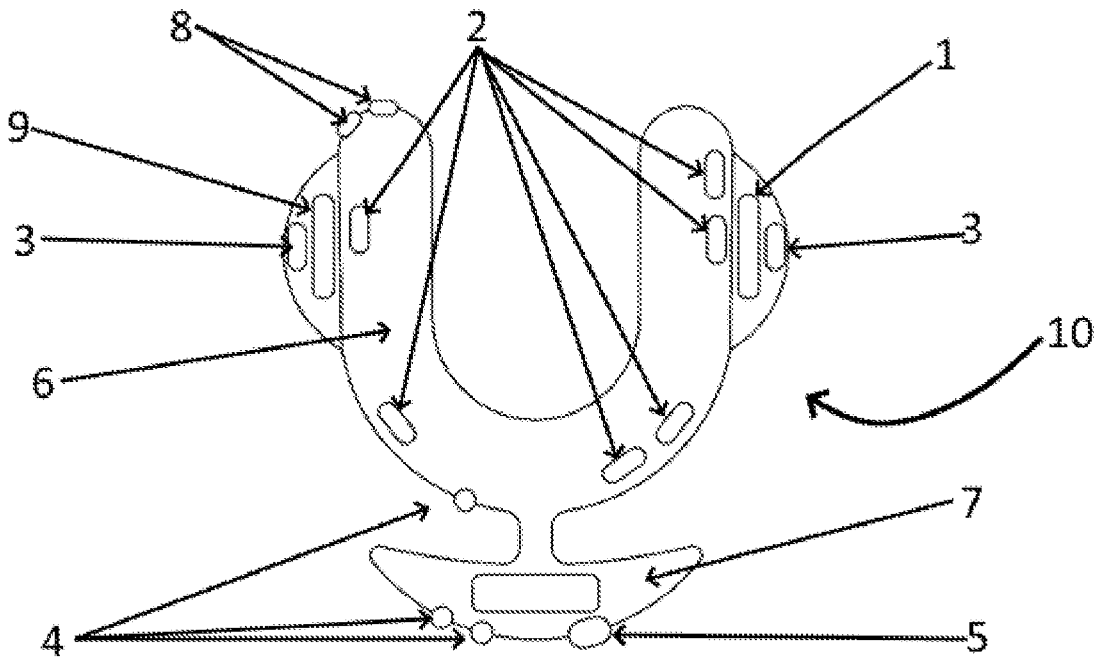
FIG. 1*a* is a partial perspective view of a mouthpiece of the present invention.

In general, the invention is a medical device that is readily usable by a patient to help optimize molecular chemistry within the brain, including improving the balance of necessary nutrients, and neurotransmitters, and improving brain (including the eyes) metabolism, and improving clearance of metabolites and misfolded proteins. The device may be in use at any time. In some embodiments the device should function at night while the patient sleeps, and be capable of treatment without active intervention from the patient. Peripheral stimulation induced neurovascular coupling and glymphatic penetrance of CSF are both more facile during sleep.

Existing treatments for AD in clinical trials focus primarily on pharmacological methods to solely reduce the burden of Aβ or tau, in a disease we know to have multimodal consequences. These treatments are also implemented well after prodromal physiological deficits are retrospectively detectable. In contrast, the ideal therapy would not only address both Aβ and tau, but target the decrease in blood flow, brain metabolism, and clearance that lead to a sequelae of negative consequences. Ideally, this therapy would have a low risk profile and ease of implementation so it could not only be used in patients with mild to severe cognitive deficits, but even be used prophylactically in people with known AD risk factors such as high blood pressure, high cholesterol, diabetes or familial history/genetic AD predisposition, or as diagnosed via emerging AD blood-based biomarkers.

Similarly, due to the very tight coupling between the arteries/descending arterioles in the brain and their surrounding perivascular spaces defined by astrocytic end-feet, any perturbation that changes pulsatility of the artery—for example modest upstream ligation, administration of dobutamine to increase heart contractility and consequent blood flow, etc.—all impact the movement of CSF in the associated perivascular space and ultimately alter brain clearance. Somatosensory coupling induced changes in brain blood flow have been shown to be heightened during sleep vs an active state, with mechanical stimulation in rodents inducing 3-8 percent increase in blood flow in the awake state vs up to 50 percent during sleep. Some of the inventors have demonstrated in rodents that stimulation of the vagus nerve increases CSF penetration into the brain parenchyma. Importantly, continuous vagus nerve stimulation—which should only create sustained dilation of the artery/arterioles within the brain—did not alter CSF penetration. Only temporally patterned stimulation to intermittently dilate and then allow the vasculature to return to its normal state over the course of several minutes resulted in increased CSF penetration into the brain parenchyma, consistent with the glymphatic hypothesis that arterial pulsations drive CSF in the associated perivascular space like a peristaltic pump. Experiments with pigs were also performed using a doppler flow ultrasound placed on the surface of the brain during facial nerve stimulation to identify the delay between applied stimulus parameters and peak flow response as well as understand optimal stimulation frequencies (data not shown due to space constraints).

The central nervous system (CNS) cerebrovascular and lymphatic system is made up of multiple components that are interconnected, including the glymphatic system. The glymphatic system (or glymphatic clearance pathway) is a macroscopic waste clearance system for the vertebrate CNS utilizing a unique system of perivascular tunnels formed by glial cells to promote efficient elimination of soluble and insoluble proteins and metabolites from the CNS. The glymphatic system is interconnected to the cerebrovascular system. The glymphatic pathway provides a para-arterial influx route for cerebral spinal fluid (CSF) to travel in the perivascular space surrounding descending vasculature and enter the brain (including the eyes) through AQP4 channels, and a clearance mechanism via convective movement of interstitial fluid (ISF) for extracellular solutes such as misfolded proteins and unwanted metabolites to be removed from the brain. Combined, the interconnected cerebrovascular, meningeal lymphatic system, and glymphatic systems provide the brain most of its needed molecules and removes most of its waste products.

The aggregation of pathogenic proteins β-amyloid, α-synuclein, and C-tau in the brain may cause the deleterious effects of numerous diseases and disorders such as traumatic brain injury/chronic traumatic encephalopathy, stroke, Alzheimer's disease, and Parkinson's disease. Removal of these pathogenic proteins and other brain metabolites and toxins has been found to have substantial therapeutic benefit, for example, in treating traumatic brain injury/chronic traumatic encephalopathy, epilepsy, Alzheimer's disease, Parkinson's disease, and improvement of general mental clarity and cognition. Modulating blood and CSF flow in the brain may also help treat normal pressure hydrocephalus and traumatic brain injuries.

Controlling the penetration rate of cerebral blood flow and CSF into the brain parenchyma can serve many therapeutic purposes, including improved nutrient delivery, increasing the rate of dilution of endogenous neurochemical transmitter concentrations within the brain, increasing the rate of pathogenic protein clearance, and altering the clearance rates of drugs delivered orally that penetrate through the blood-brain barrier or delivered via a catheter system to the brain, and reducing non-synaptic coupling between neurons to treat diverse conditions leading to increased neural activity including anxiety disorders, tremor, and seizure. Increasing transport of blood and CSF along the periarterial spaces, into the brain parenchyma, and into the cervical and thoracic lymph nodes can be driven by nerve stimulation, including electrical stimulation in the following ways.

First, temporally patterned short higher frequency bursts cause pulsations of vessel dilation and contraction, increasing arterial pulsatility which in turn increases perivascular pulsatility, increasing the blood and CSF pumping action of the perivascular space. To achieve vessel (artery and vein) pulsatility, the stimulator output engaging the nerve is also in a pulsatile form factor, such as an on and then off, or high and then low amplitude, pattern for certain durations, increasing and then decreasing arterial vessel wall dilation and contraction. The stimulation power amplitude can generate the pulsatile pattern with on off cycles, or high low, and by using square wave patterns, sinusoidal patterns, or any pattern which causes the arterial and perivascular wall to change in diameter in a temporal pattern. In general, respiration, heart beat and changes in parasympathetic sympathetic tone drive pulsatility of descending arteries in the following ways; The heart beat defines the baseline 'pulsing' of the artery, but also causes movement of the brain that can cause CSF to move in the perivascular space associated with the descending arterioles. Ligation of the carotid artery or administration of a central sympatholytic such as dobutamine can alter the pulsatility of the cerebral vasculature to drive CSF movement in the associated perivascular space. This may also be useful for driving movement of the meningeal lymphatics clearance path, which is a valvular system akin to the traditional lymphatics where flow from valve gated compartment to compartment is caused by relative motion of surrounding structures. Respiration also causes movement of the brain, causes movement of the brain tissue that can cause CSF to move in the perivascular space associated with the descending arterioles. This may also be useful for driving movement of the meningeal lymphatics clearance path, which is a valvular system akin to the traditional lymphatics where flow from valve gated compartment to compartment is caused by relative motion of surrounding structures. Sleep also drives physiological pulsations which induce electrohydrodynamic changes to brain tissue, including slow-wave vasomotor pulsations in the <0.1-2 Hz range. These very low frequency pulsations can be imaged during NREM sleep using blood oxygen level-dependent (BOLD) signal techniques, and several researchers have demonstrated that increases in BOLD signals (increases in cerebral blood volume) are inversely proportional to CSF volume. The fixed skull volume can predict that when blood flows increases into the skull during these cardiac (4-15 Hz), respiratory (1-4 Hz), vasomotor pulsations (<0.1-2 Hz), and REM sleep, the CSF flow would likely be in the opposite direction, out of the skull, and when the cerebral blood flow decreases (reduction in blood volume in the cranial vault) an increase in CSF inflow to the brain parenchyma would result. It is believed that these pulsations of cerebral blood vessels cause similar pulsations and oscillations in CSF compartments which in turn drive glymphatic clearance. The various vessel pulsation frequencies during NREM sleep cause blood flow and CSF flow to the brain parenchyma. The blood flow delivers oxygen, glucose and immune cells critical for tissue hemostasis during the vessel dilation part of the pulsations. The vessel constriction part of the pulsations directionally drives CSF and causes CSF and ISF to mix and clear metabolites from the brain parenchyma. The glymphatic system moves CSF through the brain parenchyma, delivering and removing vitamins, neuromodulators, potassium, lactate, peptides and proteins. After NREM mixing, diluting and metabolite clearance, the clearance of metabolites is further increased during REM sleep when the cerebral artery dilation further increases with reduced or minimal pulsations for an extended period. It is the goal of the present invention, at least in part, to match the cerebral vessel pulsations and vessel dilations as close as possible to their natural states during NREM and REM sleep. Changes in parasympathetic/sympathetic tone can change 'pulsing' of the artery through several mechanisms. There are direct parasympathetic/sympathetic connections to the cerebral arteries which cause them to constrict/dilate. Changes in central sympathetic/parasympathetic tone also change heart rate, respiration rate, and dilate the peripheral arteries causing compensatory changes in the cerebral arteries to maintain perfusion of the brain. Cranial nerve stimulation can alter all three of the above factors. Stimulation of the vagus has direct parasympathetic efferents to the heart which slow heart rate (isolated direct mechanism for cervical vagus stimulation). The majority of cranial nerves have cross-talk to the facial nerve, which has direct parasympathetic projections to the cerebral arteries through the sphenopalatine ganglia causing the arteries to dilate. The cranial nerves project to the trigeminal sensory nucleus which indirectly connects to the nucleus of the solitary tract (NTS), or project directly to NTS. NTS in turn causes central changes in sympathetic/parasympathetic tone, making changes to arterial pulsatility. Cranial nerves have sensory fibers which can cause 'entrainment' oscillations at the applied frequency of stimulation within the connected regions of the brain. By inducing activity in these areas, local blood vessels dilate to keep up with the stimulation driven increased metabolic demand, known as neurovascular coupling.

Electrical stimulation of easily accessible neural inputs located outside of the brain can modulate CSF flow variables, including induced cardiovascular and respiratory changes, dilation of arterial vessels and increase the pulsatility (change in the vessel diameters over time relative to a mean vessel diameter) of penetrating arterial vessels in the brain thus leading to increased clearance of misfolded proteins from the brain. See U.S. Pat. No. 11,395,914, incorporated herein by reference (hereinafter the '914 patent).

Specifically, electrical stimulation of other cranial nerves or local areas around the other cranial nerves may selectively cause oscillations in pressure and dilation of arteries that help to improve waste clearance in the brain. However, these methods are limited by the body's compensation responses that quickly habituate these effects over time and do not maintain a sustained response when nerves are continuously and repeatedly electrically stimulated. In this respect, continuous stimulation of the other cranial nerves only causes brief transient changes in blood flow. They also don't cause sustained changes in neural activity which tend to peak early in a pulse train and then return to near baseline (and even overshoot after the period of stimulation ends).

A pulsatility of vessels has intrinsic time constraints related to the time for vasodilation/constriction and time to return to baseline (TBL) after electrical stimulation, which may affect the pulsatility response. In this respect, these time constraints for stimulation induced vasodilation/constriction and subsequent return to baseline define the maximum and minimum changes to pulsatility. The '914 patent provides control of temporal patterning and the stimulation waveform in order to maximize the physiological response to cerebral pulsatility and its resulting effects on brain waste clearance. Thus, the electrical stimulation is temporally patterned to generate multiple vasodilation/constriction pulses in succession to optimize and sustain the pulsating action to continuously drive CSF into the brain parenchyma over long periods of time. Data such as imaging data may be used to isolate the time lags to sync with closed-loop measures such as accelerometer measuring respiration rate, which may account for this delay in a closed-loop fashion, which will have a nerve specific and potentially a subject specific component. This calibration may use and inform AI/Deep Learning to develop the most efficient solutions for control.

Electrical stimulation of specific cranial nerves such as the branches of the trigeminal nerve, i.e., buccal and lingual branch nerves, and the facial nerve creates a more sustained pulsatility activity compared to stimulation of other cranial nerves. One possible explanation for this is that the facial and trigeminal nerves have direct sympathetic/parasympathetic innervation of the cerebral vasculature through several routes, including through the sphenopalatine ganglion (SPG), which are part of neural pathways that directly control the vasodilation/constriction of the cerebral arteries. As a result, the time course for dilation and constriction after a stimulation burst can be quicker than other cranial nerves because the response is quicker than inputs from the spinal cord which change peripheral sympathetic tone or peripheral inputs such as the sciatic nerve that change blood flow primarily through sensory activity mediated neurovascular coupling. Other advantages include having sensory only points of interface that are superficial to the skin, making them easier to decouple from therapy limiting unwanted motor activation.

Also, stimulation through pathways that change sympathetic/parasympathetic tone outside the brain dilate the peripheral vasculature outside of the brain. The change in blood flow in the brain is primarily in response to this change in peripheral blood flow to maintain perfusion (there are also occasionally indirect connections between the vagus and facial nerve in some subjects). As vagus nerve stimulation only indirectly influences blood flow in cerebral vasculature, it has a slower time constant between burst of stimulation for changes in flow to return to normal.

A porcine study was performed using a unique temporal patterning to optimize pulsatility using direct neural inputs to cerebral vasculature, to impact dilation. 25-50 Hz for facial nerve stimulation was found to be the optimum period to create a full pulse without attenuating the peak flow response but accelerating the return to baseline to the 1-2 second range. At higher frequencies (75 Hz or above), habituation occurs before peak flow change is obtained, causing a weaker effective pulse. Hence optimum stimulation parameters are 1-5 second bursts at 50 Hz, with a period of 1-5 seconds unstimulated in-between bursts to allow for the system to recover before the next set of pulses. Baseline Stimulation Parameters: Pulse widths can vary between 15 microseconds and 5 milliseconds, amplitude at highest tolerable level without excessive EMG. For electrical stimulation, maximum amplitude varies for placing electrode non-invasively vs directly on the nerve of interest, but ranges between 100 microAmps for invasive and 40 mA for invasive. A high frequency carrier wave (300-5 Khz) may be used with non-invasive stimulation. Habituation may occur within a 30 second pulse train as low as 10 Hz, which may be advantageous in that you get a higher peak flow at 10 Hz that then gets cut off quickly through habituation.

A second means of nerve stimulation to modulate CSF flow in the brain parenchyma is by modulating the opening of APQ4 channels in astrocytic endfeet, thru nerve stimulation at low frequencies, in the approximate range of 0.1-10 Hz. AQP4 channels allow that the CSF in the perivascular space surrounding the descending arterioles to pass into the brain parenchyma can be opened with electrical stimulation. These channels are preferentially open during slow wave sleep (or slow waves introduced by anesthesia), causing an up to 60% increasing in CSF penetration into the brain parenchyma during slow wave sleep. However, in the aging brain, astrocytes may become increasingly reactive causing depolarization of the AQP4 channels. Electrical stimulation has been shown to reduce astrocyte reactivity and polarize the AQP4 channel. AQP4 channels are increasingly open during sleep because AQP4 channels are known to open due to local temperature changes, and changes in activity during slow wave sleep may cause local temperature changes that result in opening of the channels. Moreover, there are data to suggest AQP4 channels may be directly responsive to the electric field generated by slow wave sleep. There are lipid rafts in the AQP4 channels that have previously been shown to cluster based off of low frequency versus high frequency stimulation (ex vivo preparations), and this clustering of lipid rafts may cause the channels to open. Cranial nerve stimulation induces slow wave oscillations. It is a well-known phenomenon that most peripheral inputs, if stimulated at low frequencies, induce sensory entrainment within the associated sensory regions of the brain at the same frequencies.

A third means to modulate extracellular CSF and ISF flow in the parenchyma may be by increasing the distance between neuronal/non-neuronal cells to allow more flow around these cells, which may improve waste clearance. Application of a noradrenergic receptor antagonist will cause neurons to become less active and increase CSF penetration into the parenchyma. When neurons become less active they are known to 'shrink', expelling their fluid con-tents in to the extracellular space, increasing the distance between neuronal and non-neuronal cells, allowing for a wider 'path' for flow through the extracellular space. Electrical stimulation can reduce activity of neurons. Cranial nerve stimulation may decrease neural activity and reduce inflammatory cytokines, causing neurons to shrink thus decreasing extracellular resistance of CFS flow through the brain parenchyma. Low frequency entrainment may be used to shrink neurons globally due to lower neuron activity, thereby reducing resistance of CFS flow through the brain parenchyma.

A fourth means of modulation of CSF flow in the brain parenchyma is by stimulating for periods at approximately 40 Hz to increase phagocytic activity in glial cells. Gammaoscillations have produced several effects, such as increasing the brains immune system causing increased phagocytic activity of microglia. Animals research has shown 40 Hz stimulation reduced neurodegeneration and increased synaptic density, improved cognitive function, and normalized circadian rhythm (Adaikkan et al., 2019; Martorell et al., 2019; Yao et al., 2020). By optogenetically activating the visual cortex directly at 40 Hz, and then in subsequent studies flashed lights in front of the eyes at 40 Hz, researchers observed a reduction in Amyloid Beta. They speculate this is due to 40 Hz causing a change in glial cell activity, which phagocytose (meaning engulf and break down) misfolded proteins. They did not directly show an increase in phagocytosis mediated by glial cells/macrophages was responsible for their observed reduction in amyloid beta, but they did some gene expression afterwards and noted there was an increase in gene expression associated with phagocytic behavior. Similar stimulation patterns can be achieved via electrical stimulation.

Fifth, stimulation to reduce central sympathetic tone can increase CSF production and pressure for CSF movement through the perivascular space. Production of CSF at the choroid plexus creates the driving pressure to push CSF into the perivascular space associated with the descending arterioles, through the AQP4 channels in the astrocytic end feet, and into the brain parenchyma. This creates the pressure gradient to drive extracellular waste, such as misfolded proteins through the parenchyma to the veins/arteries, where active transport mechanisms transport misfolded proteins past the blood brain barrier. In addition, the CSF in the perivascular space drains into the traditional lymphatic system through the cribriform plate, as well as exits the brain through perineural routes such as the olfactory nerve. Increasing CSF production increases the driving pressure through this pathway. Prior studies have shown that sympathectomy of the choroid plexus (removing sympathetic nerve input to the choroid plexus) increases CSF production at the choroid plexus by 30%, increasing this driving pressure. The full glymphatic path of CSF production at the choroid plexus creates a driving pressure to 'push' CSF into the perivascular spaces associated with descending arterioles. This pressure and the pulsatility of the arterioles drives CSF through AQP4 channels in astrocytic end feet which surround the perivascular space into the brain parenchyma. This creates flow in the extracellular space in the parenchyma to drive waste movement/misfolded proteins to the perivascular and perineural spaces where clearance/efflux from the brain is mediated.

The present invention provides full commercial embodiments of unique devices to conveniently increase blood and CSF flow to the brain via stimulation of the trigeminal/facial nerves, nerve inputs associated with the baroreflex (vagus, aortic depressor, carotid sinus, baroreceptor beds in the bulb, aorta), and peripheral nerve inputs not clearly associated with the baroreflex (median nerve, sciatic nerve, tibial nerve, spinal cord), and also methods to optimize the effectiveness of the devices. Stimulation of the above nerves for the above reason may be accomplished by means other than electrical. Other Stimulation means may include thermal, vibration (force/sound), pressure, light, olfaction (odors), magnetic, to name a few.

Waste Clearance Enhancement System

The waste clearance enhancement system (WCES) described in this invention may include one or more of the following, or multiple of the following in any combination, combined into a single device, or separate devices connected via wire or wireless, but working together to provide therapy. The system includes a stimulator, and possibly one or more of the following, a charger, a reader, a digital application, a cleaner, a controller, a sensor, and other supporting devices as described. Some of these components may be combined into a single device. The WCES may also have means to connect with other systems in order to use data collected from other systems, or alternatively control the other systems, or both. For example, the waste clearance enhancement system may be linked to or combined with a CPAP system. Since one form of pulsations that effect the brain are respiratory pulsations, the waste clearance enhancement system may be programmed to coordinate with a CPAP system respiratory cycle and in conjunction with other cerebral pulsation cycles (cardiac and vasomotor). The WCES may also connect to other systems that collect and transmit bio data, such as smart watches, to understand proactively what therapy parameters to deliver, or proactively if the therapy being delivered is appropriate or optimal, or if the therapy needs to be modified or augmented. The WCES may monitor sleep stage either directly with on-board sensors or indirectly by harvesting sleep stage information from other devices. This sleep stage information may be used to adjust the stimulation algorithms. As one example, a slow vasomotor stimulation pattern may be used during deep sleep, and a longer stimulation may be used during REM and nREM sleep. Sensing the end of REM to light sleep transition where mixing can occur may also be incorporated. The WCES may apply stimulation patterns to match and amplify clearance system patterns from each sleep stage, or alternatively the WCES may proactively establish or set the optimal clearance system patterns, or there may be a combination of amplifying and establishing clearance, depending on each patients needs.

The WCES may or may not contain ancillary stimulation components for pill swallowing through deliberate activation of motor nerves, which can often be a problem in later stages of AD.

The WCES might also cooperatively share sleep data, sleep scoring data, cognitive test data, biometric trending data, etc., and data related to if the patient has improved to one or more of these measures. The data may be used to adjust the therapy (to further improve or stop) automatically, or by approval from a clinician, or patient. As noted above, the WCES may include and/or run a digital application. A digital application, as used herein, includes or refers to computer-readable instructions which are executable by processing resources to perform a task.

A digital application may include supporting diagnostic and therapeutic parameter adjustments by a clinician, care giver, supporting organizations, the patient, or by a cloud based solution, like an artificial intelligence or machine learning models. The digital application may reside on one or more components of the system, or an ancillary device connected to the system, like a computer, digital pad, smart phone, reader, or any part of the WCES, or another system connected to the WCES. The digital application or the hardware in the WCES, a connected system, or the like may allow for connections to the cloud, the internet, parts of the WCES, or connected systems, and it may act as a connecting hub for cloud resources, parts of the WCES, and/or other connected systems.

The digital application may be used for patient reported outcomes. As an example, upon waking and turning off the system using the controller, reader, cell phone application, or on-board button, the digital application may ask the patient how they feel, or how well they slept, if they would like to take a cognitive test, if they would like to do a blood test, (which may be an on-board blood test). The cognitive test results could be used for individual patient trending. The cognitive test results, sensor data, blood test data, sleep stage data, stimulation parameters, and other sleep or system or shared data, could be used by the digital application for AI learning, system parameter adjustment, recommendations, patient risk, or can be sent to a clinician who is following the patient. Onboard or connected biodata may inform, the digital application. Biomarkers such as as a Tau or Amyloid Beta blood levels may be used, along with cogs data, as an example, to diagnose if a patient is stable, or on a dementia trajectory requiring prevention or therapy. The results could be used for input into a machine learning algorithm to inform current or future stimulation parameters for the patient or a patient cohort. The digital application may also use the biometrics to track drugs waxing and waning that can be used to help tailor drug administration profiles and alternatively, or in combination with general drug tracking for the cognitively impaired. One stop 'shops' are important for people with mild cognitive impairment or caretakers of said individuals.

A potential patient may initiate patient data tracking and trending initially with only the digital application software part of the system or product. Initial baseline trending may show a stable or normal reading, including reference to a larger patient population data set. Over time the stability or normalcy of the patients' results may change, and the system may suggest a therapeutic solution to maintain optimal results. The therapeutic solution may include one or more of the system solution components described here in. The system solutions may include one or more components meant to improve blood flow, CSF or ISF flow through the brain parenchyma, improve sleep, dampen hyperexcitability of neurons, reduce inflammation or improve drug delivery to the brain parenchyma. Baseline digital application patient data collected years before therapy is required may give the system an optimal baseline of the patient, allowing therapeutic to be optimized. Therapy may initially be very minimal, in applied time, duty cycle, or amplitude.

Stimulation systems for nerve modulation of blood and CSF flow through the brain can be implemented in several form factors, such as implantable, wearable (on the skin), intra-cavity (in the ear, nose, eye, or mouth), or any form factor which in which the body can sense. Stimulation means may be direct or indirect electrical, mechanical (including sound), thermal, taste, auditory, ultrasound, IR, magnetic, or light. Any of these basic stimulation form factors may be used for nerve stimulation to modulate CSF flow through the brain by one or more of the previously mentioned stimulation mechanisms pathways. Implementing these stimulation methods for increasing blood and CSF flow through the brain parenchyma may be accomplished individually or in any combination of two or more, and in a single device or multiple devices, at a single stimulation location or multiple, and the timing of stimulation methods may be implemented in series or in parallel.

The stimulation level may be relatively low, or nonexistent, for an awake patient, such that the patient can fall asleep, but when the patient is asleep, the stimulation may start, or the stimulation amplitude may be increased, or modified based on a preprogrammed pattern, or adjust based on sensor feedback. Confirmation that the patient is asleep and what sleep stage they are in may be determined by one of more of several sensors, and the sensors may either be directly associated with or part of the stimulator system, or the sensor(s) maybe on another device with connectivity to the stimulator system. The associated devices with sensors may be those on a smart watch, a smart phone, a EEG system, activity trackers, or other biological measurement systems.

Alternatively, the start of the higher amplitude may be time based, for example, automatically adjusting stimulation parameters within a few minutes after a particular sleep stage in reached, as determined by sensors, or in another example, 30 minutes after the patients turns the stimulator on. Alternately, in an example, a smart phone microphone may listen to breathing rate and communicate to the stimulator system on when to start, change or stop a stimulation cycle. Similarly, pulse rate, heart rate variability, microneurography (non-invasive or patch) blood oxygen or body temperature may be monitored on a smartwatch, fitness tracker, or similar device and adjust the stimulator. The electrical stimulation may be initiated, stopped, or adjusted, in a closed-loop fashion, by way of combining any form of electrical stimulation mentioned with a sensing modality that may include electrophysiological and/or CSF flow rate measurement. Measurements may include EEG, skin conductance or electrodermal activity, skin temperature, heart rate variability, breathing rate, motion or actigraphy, blood pressure, heart rate, blood oxygenation. Additionally, non-invasive measurements of autonomic nerve activity may be performed, including, blood pressure, galvanic skin response, heart rate, and respiration variability. Measurements could be taken with a needle that is non-invasive or via a patch. Ideally, on-board sensors or connected sensors may provide information related to sleep stage as well as specific cardiovascular or glymphatic pulsation. The latter being optimal inputs for temporal stimulation patterning. Stimulation may be timed with natural vascular pulses to amplify the natural pulsations by following natural oscillations with a closed loop sensing system, or used to initiate natural pulsation timing of known optimal parameters, or override natural pulsations, or the natural and stimulated pulsations may work in parallel and independent. Initiating and entrainment of sleep oscillations and vascular pulsations may be enhanced by using multiple stimulation means, such as electrical, and auditory, for example.

A preferred embodiment of the stimulation system includes a stimulator, a means for powering the stimulator, and a means to communicate with the stimulator. An example stimulator may be in the form factor of a mouthpiece, a transdermal wearable stimulator, or an implantable stimulator. The stimulator may be powered by a rechargeable battery, which is charged by a battery charger. Communication with the stimulator may be via a wireless signal, e.g., Bluetooth or radio signal to a computer, digital tablet, digital watch, digital ring, cell phone or other computing device which contains appropriate digital application software.

The stimulator system may have only one stimulation output setting or may have multiple output settings that the patient can select from, or the stimulator system may be programmable by the patient or clinician through another device, such as a cell phone, or the stimulator system may automatically adjust itself per preprogrammed functions, to optimize key sensor measures such as arterial pulsatility, or the various settings may be partly user adjustable and partly automated. Stimulation output patterns, electrode selection, power amplitudes, sensor data selection, sensor amplification levels, or other variables may need to be adjusted manually or automatically to accommodate each patient's needs. For instance, some patients may not respond to certain electrode placements, or the nerve sensitivity to a particular electrode placement may change over time. Also, some patient may not respond to stimulation output routines meant to increased CSF flow via one of the means described above, such as arterial pulsatility, but they may respond to an algorithm meant to increase AQP4 channel opening.

Figure 1B:
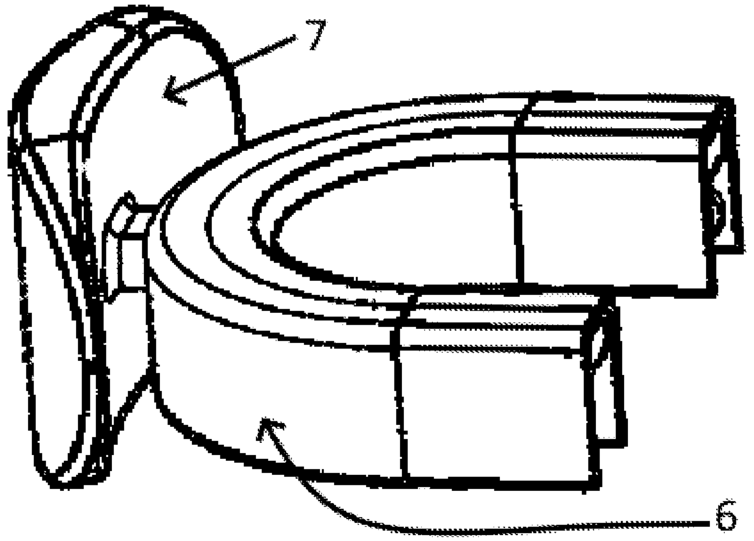
FIG. 1*b* is a partial perspective view of a mouthpiece of the present invention.
Figure 1C:
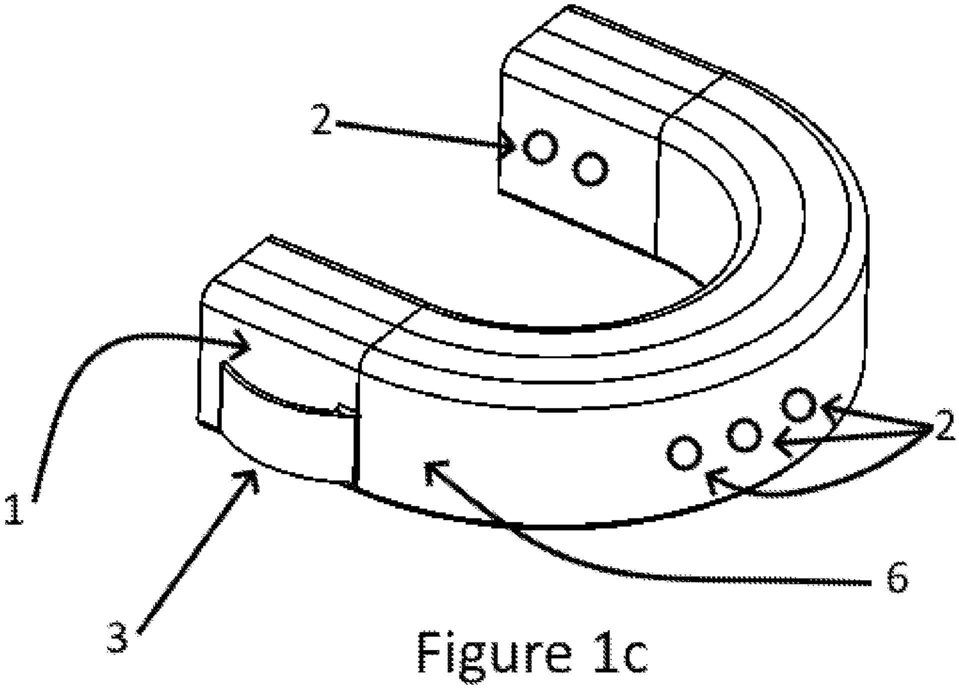
FIG. 1*c* is a partial perspective view of a mouthpiece of the present invention.

A patient or the stimulation system may learn which output stimulation routines give best results by monitoring biosensor feedback, or by monitoring cognition test data, or by noticing how refreshed and cognitively alert they feel after sleeping with particular stimulator system algorithms. Guided temporal interference/interferential stim strategies may also be incorporated. These variable settings may be scrolled through on the stimulator system by pressing an on off button multiple times or holding it down. Visual and audible indicators may indicate to the patient which setting the stimulator is on. With reference to FIG. 1, visual indicators 4 on stimulator may be LEDs, such as multiple color lights or a single-colored light that flashes a differing temporal pattern for different settings. Similarly, an audible indicator (not shown) may be, as an example, a beep, which beeps a different number of times for each setting. Alternatively, the device may communicate with another user interface device, e.g. communicating wirelessly or through a corded connection with a handheld device, through the cloud or another network with a remote device, or with a software application for user control and data logging. Such an application may be used to control all variables or only some of them. For instance, the stimulator may have an on off switch, with all other variables adjusted via the software application. Adjustable variable settings may be output voltage amplitude, output current amplitude, stimulation patterning such as duty cycle or frequency, interweaving and combining of various temporal stimulation patterns meant to engage different mechanisms for CSF flow modulation, and which electrodes 2 (FIG. 1) to use if multiple electrode 2 locations are present, and what electrodes to stimulate, in what order, and to what degree. Thus, the electrodes may be each similarly stimulated, or may be differently stimulated (duration, timing, and amplitude) as needed.

The inputs for these choices may be provided on a number of different devices. For example, a pressure sensitive switch may be present on a mouth guard 10 or other stimulation device. Electrodes 2 may sense when contact is being made with one or more of them. The visual and audible indicators may be on the stimulation device as well. The inputs may also be on the charging station, a reading station, a docking station, a connected hand held device such as a cell phone, ipad, controller, or other device. A screen may then aid the user in selecting the inputs.

The stimulator system may have one or more feedback mechanisms meant to sense its environment such that adjustment may be made to output by the patient, by the clinician, or by machine learning techniques, to optimize parameters such as battery life, patient safety and/or side effects, blood flow, CSF flow, or ease of use, placement and electrode selection and electrode movement. The preprogrammed settings may also include machine learning algorithms meant to optimize device outputs for a patient over time. An example of the latter may be that an individual stimulator system may initially cycle through a multitude of power, wave form, electrode selection, and other settings during initial uses and based on EEG data, muscle activation data, nerve activation or electrode impedance data, then select a new baseline set of power and electrode selection variables, which will then become the new baseline output variables. Automated modifications to the baseline output variable adjustments will likely reduce over time, unless key patient variables or device to patient fitment variables change. This type of learned data may also be collected from each user through a software application, such as a cell phone application, and then pooled and used as initial settings for new builds of stimulator devices for a patient, or for groups of similar patients, or for general groups of patients, and in doing so minimize initial set up time for a specific patient, groups of patients, or patient in general. Sensor systems may be used to track adjunct drug status to optimize drug administration separate from device, or synergize with device function.

Figure 7:
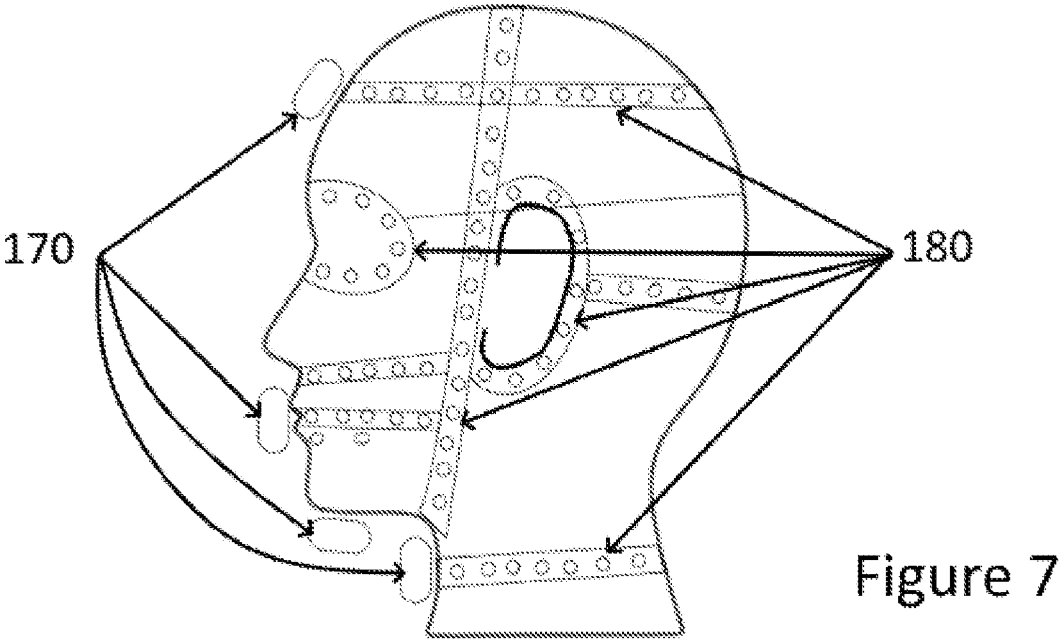
FIG. 7 is a partial perspective view of a stimulator system of the present invention.

The stimulator 10 form factor may be a mouthpiece placed in the mouth, as in FIG. 1. The stimulator may also take a multitude of other configurations, such as a transdermal patch or other device affixed to or worn on the skin, and or in the form of a hat, and or in the form of glasses, a sleep mask, and or in the form of goggles, and or strapped in a multitude of combinations as is depicted in FIG. 7. The stimulator may also be an earpiece placed in or on the ear, similar to the form of a hearing aid, ear clip or earplug. The Ear bud/ear clip may be on the cymba conchae for aVNS, but also the other areas of the ear that are routes for the facial and trigeminal in addition to auricular vagus. The stimulation system may have a portion inserted into the nose. The stimulation system may also be a combination of two or more of these, such as the multitude of configurations depicted in FIG. 7. An example of the latter is a mouthpiece or oral appliance with electrodes that are placed in the mouth, with a conductor running out of the mouthpiece, between the patient's lips, and to a stimulator which is adhered to the skin under the chin. A sleep mask or head band configuration may be of particular use as it can engage the V1 branch of the trigeminal nerve, in applying electrical stimulation, temperature changes, light, sound, or other stimulation, and at the same time the mask can have built in sensing capabilities, such at EEG electrodes for example. In another embodiment the stimulator system may include an adhesive strip placed across the nose. In several of these embodiments the stimulator system may serve multiple purposes such as assisting breathing, reducing snoring, or blocking out light, or be a part of a larger system that includes other components for these purposes.

The stimulator, and sensing system, or both, may be designed into, or operate in conjunction with, other systems, and in particular those which may contact the patients head and or neck during sleep. For example, the stimulator system may be incorporated into a mouthpiece which is also used to reduce snoring or teeth grinding, or the stimulator system may be incorporated into a CPAP facemask, or the stimulator system may also be combine with a tooth whitening and cleaning system. The stimulator system may stimulate for increased CSF flow and at the same time, or sometime during the same use period, it may stimulate for other preventative or treatment needs, such as stimulation for saliva production or stimulation to reduce pain.

FIG. 7 shows examples of additional cranial and facial locations for placement of the stimulator, electrodes, and sensors, but for clarity cannot show all locations, on the head where stimulation and sensing may be done with the invention.

The stimulator could also work in conjunction with other bio sensor systems and modalities commonly connected to software applications (such as on a cell phone) which measure other EEG, heart rate, body temperature, movement, whether through a smart watch or fitness tracker, cell phone app, or a medical device for those purposes.

The stimulation system may have one or more methods for stimulating the patient to increase CSF flow through the brain parenchyma, as well as it may clean the brain of miss-folded proteins. The stimulation system may also have direct or indirect means of feedback sensing or measuring the achieved results. Feedback sensor data may be used to inform the user of which output regimens or combination of output variables are the most effective for each patient including which electrodes should be stimulated during which sleep cycle periods. Direct or indirect feedback measures using nerve activation, EEG data or arterial pulsatility data may be used to measure if a stimulation algorithm is inducing the appropriate response. Output variables can be adjusted through ranges to find optimal outputs for a given patient. If the patient chooses, the patient data can be sent to a pooled data source at a company or in the cloud, such that it may be used to tailor initial stimulation settings for future users, or the pooled data may be used to inform future generations of the stimulator products, including general device configuration, starting algorithms, electrode placements, and other design variable. In patient treatment regimens involving drug administration, the system's sensors may be used to track adjunct drug status to optimize drug administration. This may occur for a treatment separate from device, but it may also be used to synergize the drug regimen with the stimulation system's function.

In one embodiment the stimulator system connects to the patient's phone or other digital medical equipment containing a digital software application such that the patient may adjust stimulation settings, including frequency, power levels, timing of certain cycles, or the patient may want to upload and track feedback data over time. A digital device, as used herein, includes a processor and memory, which may form a computing device and have communication capabilities. Communication between a cell phone and the stimulator could be facilitated through the radio, wifi, Bluetooth, other RF means or direct electrical contacts. The communications could give the patient an understanding of real-time data, such as real-time electrode impedance data to verify tissue contact, or vessel pulsation data to determine if the target nerve is engaged. It may be necessary to have simple LED's or similar visual or auditory means to identify the latter. LED's or other lights on a stimulator could be visualized in a mirror, or by having the user place an object, like a mirror, next to it, when in an dark environment.

In one embodiment the present invention provides a method of improving waste clearance through the perivascular system of the blood brain barrier including positioning at least one electrode in close proximity to a nerve; generating a carrier wave having a carrier frequency stimulating the perivascular system into increased CSF/ISF flow; generating the modulation wave having a predetermined periodicity providing a first period of stimulation of the perivascular system and a second period of relaxation of the perivascular system, the predetermined periodicity selected to increase pulsatility over continuous stimulation of the perivascular system by the carrier frequency; and modulating the carrier wave and applying the carrier wave to the electrode.

For stimulation of the facial nerves, trigeminal nerves, and sphenopalatine ganglia the carrier frequency of the carrier wave may be between 5 Hz and 55 Hz and centered around 50 Hz. In another embodiment, the carrier wave may be below 10 Hz. The carrier wave may be selected to prevent habituation, but may also be selected to provide a level of habituation where advantageous. The modulation wave may have a frequency between 0.5 Hz and 0.1 Hz. The modulation wave may have a time duration ("bursts") of between 1 second and 10 seconds with a pulse interval (unstimulated period between "bursts") between 1 second and 10 seconds. The off period to allow 'wash out' of the clamping effect before starting a new sequence may be, for example, 45 seconds to 1.5 minutes after a 30 second stimulation train.

For stimulation of the vagus nerve, carotid sinus nerve, and baroreceptors the carrier frequency of the carrier wave may be between 5 Hz and 50 Hz and centered around 30 Hz. In another embodiment the carrier wave may be between 5 Hz and 10 Hz, with for example a 30 second pulse, to prevent habituation. In another embodiment the carrier wave may be between 8 Hz and 25 Hz. The modulation wave may have a frequency between 1⁄45 Hz and 1⁄180 Hz. The modulation wave may have a time duration ("bursts") of between 15 second and 60 seconds and around 30 seconds with a pulse interval (unstimulated period between "bursts") between 30 seconds and 120 seconds and around 60 seconds.

For stimulation of the sciatic nerve and peripheral nerve the carrier frequency of the carrier wave may be between 5 Hz and 55 Hz and centered around 50 Hz. In another embodiment the carrier wave is centered below 10 Hz, to prevent habituation. The modulation wave may have a frequency between 1⁄300 Hz and 1⁄540 Hz. The modulation wave may have a time duration ("bursts") of between 1 minute and 4 minutes and around 3 minutes with a pulse interval (unstimulated period between "bursts") between 4 minutes and 6 minutes and around 5 minutes.

In one embodiment, the stimulation timing between electrodes can be a repeating sequential pulse electrode by electrode.

It is thus a feature of at least one embodiment of the present invention to introduce periods of relaxation into the electrical stimulation parameters allow for recovery processes of the dilated blood vessels In another embodiment, the stimulator is first placed in or on the user while under medical care. The results of the stimulation parameters may be monitored and adjusted manually or automatically through various techniques and equipment using EEG, computed tomography (CT) scans, magnetic resonance imaging (MRI) scans, or other medical equipment, to determine the ideal stimulation parameters, which are then set in place for the stimulator. These settings may then be used generally for all similar patients or may be optimized for particular patient classes such as by age, height and weight, and sex. Ideally the set point will provide a relaxation time (pulse interval) that is no less than the time to return to baseline ($T_{BL}$) measured after brief periods of stimulation (pulse duration).

In another embodiment the stimulation system is connected via Bluetooth, another RF means, IR means, or directly wired, to a user interface. The user may input into the user interface data such as daily or hourly or minute by minute quality of life results, cognitive test results, or other feelings, in response to prompts or questions and stimulator outputs, which would then allow the system to determine if the stimulator system outputs parameters or sensor selection or gain parameters need to be adjusted. The user may respond to tests, such as for example taking a dexterity test for muscle control in the interface. The patient information collected by the system or digital software application may be shared with the cloud for inputs into machine learning algorithms, or shared directly with clinicians, clinics or third parties managing patient outcomes.

In one embodiment of the stimulator system of FIG. 1 is charged via a standard power cord (not shown), and stimulator 10 is the entire system, such that other than the charging cord it operates independently to provide appropriate and fixed stimulation patterns. The device is switched on and off with a simple switch. The switch may be a pressure switch on the stimulator, or on/off switching may simply be determined by if the charger cord is plug in or not, so if it is plugged in the system is off and if it is not plugged in the system is on.

Alternatively, in another embodiment, the stimulator 10 is powered by a rechargeable battery within stimulator circuit 1. In one such application the stimulator 10 is charged via RF. It has multiple electrodes and multiple sensors and software means to use feedback data to understand when to turn on stimulation, what stimulation parameters to use, and how to adjust stimulation parameters to optimize therapy. Ideally the stimulator system is able to communicate to a user interface device with a custom digital software application, such as a smartphone, a digital tablet, a computer, or directly or indirectly to the cloud. The digital device may also track directly or indirectly various forms of user data from wearable patches, clothing, watches, rings, or other smart devices, such as EEG signals picked up through a EEG tracking pillow, or EEG headband, or neurography/microneurography, or respiration rate directly through the cellphone microphone, or SpO2 signal data, ECG, pupillometry, blood pressure, altitude, blood amyloid ratios, blood ptau levels, speech variability, heart rate variability, body movement or acceleration or movement variability and stability, body or environment metrics like temperature or pressure or light, tissue impedance or acidity, to name a few.

The stimulator may directly or indirectly measure beta amyloid levels or ratios in the blood, phosphorylated tau levels, or levels of other brain metabolites. The stimulator, reader, controller or other connected device, or non-connected device may include an on-board blood analyzer which may allow the patient to quickly collect the former data. The digital application software may read and record the results directly.

Increasing the penetration of CSF into the brain parenchyma can serve many therapeutic purposes, including diluting endogenous neurochemical transmitter concentrations within the brain, altering the clearance rates of drugs delivered orally that penetrate through the blood-brain barrier or delivered via a catheter system to the brain, and reducing non-synaptic coupling between neurons to treat diverse conditions leading to increased neural activity including anxiety disorders, tremor, and seizure. It is understood that the present invention is not limited to the treatment of traumatic brain injury/chronic traumatic encephalopathy, epilepsy, Alzheimer's disease, and Parkinson's disease and the like and may also be used to treat other conditions and disorders such as normal pressure hydrocephalus caused by a buildup of CSF in the brain parenchyma by increasing the clearance of CSF through the brain. Also, clearance of orally administered drugs that cross the blood brain barrier, or drugs/biomolecules that are infused via an injection/catheter, can be modulated by changing the CSF flow rate.

To facilitate memory consolidation of new information that was learned during daily tasks, the stimulator can be independently activated to create a paired sensation with daily learning tasks, create a distinct sensory pairing with the new neural circuit being formed to encode the memory. During sleep this nascent neural circuit is consolidate by 'replay'. Improving memory via automated targeted memory reactivation during sleep. The sensory stimulation that has been paired can be periodically activated during sleep to activate the paired neural circuit to help initiate 'replay' and create more 'replays' to consolidate the memory engram.

Stimulator

Figure 15:
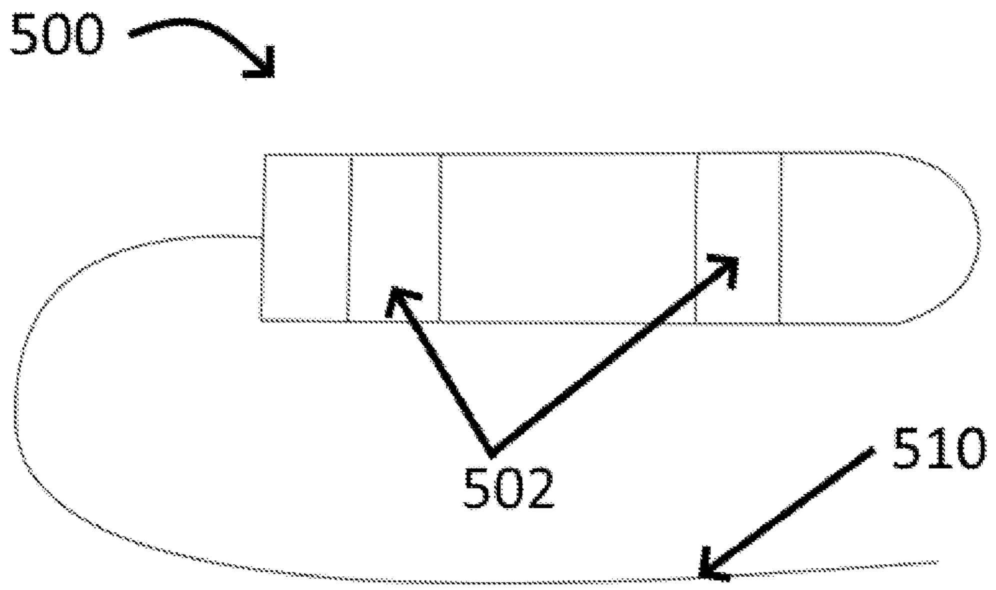
FIG. 15 is a micro electrode and antenna assembly for a stimulator assembly of the present invention.
Figure 16:
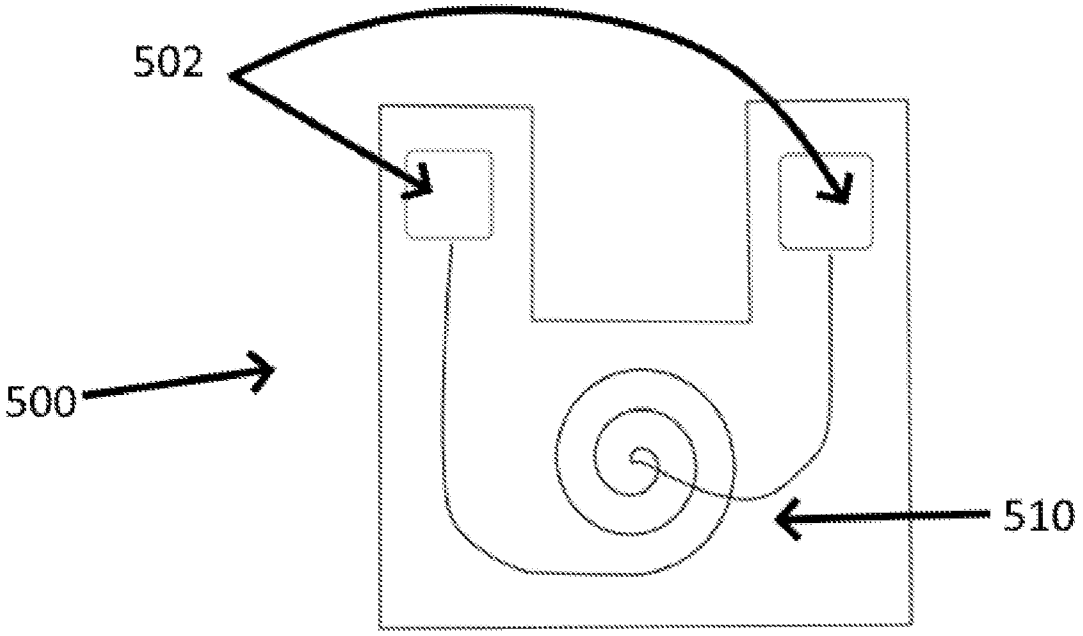
FIG. 16 is a minimally invasive electrode and antenna assembly of the present invention.
Figure 17:
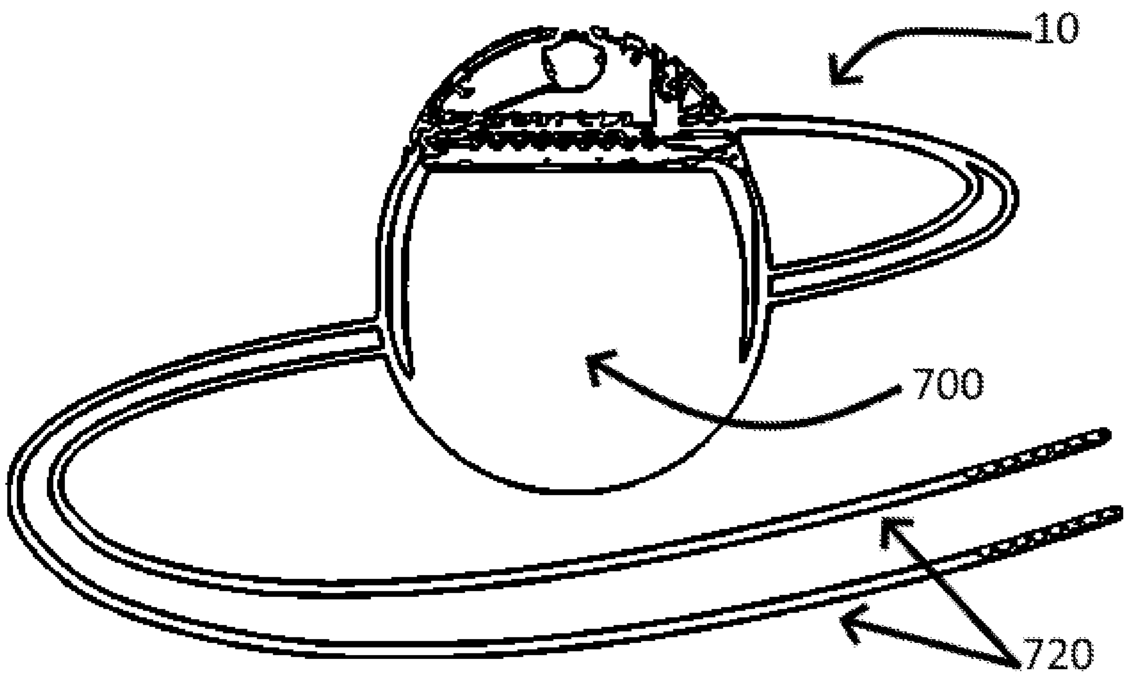
FIG. 17 is an implantable assembly of the present invention.

The stimulator 10 form factor may be one of several form factors. As an example, stimulator 10 it may be in the form of an implantable pulse generator 700 (IPG), with a lead or leads 720, FIG. 17. The IPG may be implanted anywhere transdermally, with leads placed such that the electrodes align with any of the nerves previously mentioned. In another example, an micro electrode and antenna assembly 500 in FIG. 15 may be injected or placed next to any of the nerves previously mentioned in a more minimally invasive configuration, such as injected near the mental nerve near the jaw, and then either powered by a wearable, such as a mouthpiece, or powered by an RF source near the patient, like an RF pad under the pillow. Ideally the assembly in FIG. 15 has at least two electrodes 502 and at least one antenna 510. The minimally invasive electrode and antenna assembly 500 could be made like that in FIG. 16, very thin and flexible, such that it may be placed directly under the skin without notice. Thus it may be placed in extremely close proximity to the V1 branch of the Trigeminal nerve near the eye brow, for example. Such an assembly would have at least two electrodes 502 at least one antenna 510, and be made of a very thin form factor, such as a thin flexible circuit known in the art. The stimulator may also be in the form factor of any wearable device, such as a watch.

In one embodiment the electrodes may be directional electrodes. Or an electrode may have multiple segments to it that can be manually or automatically chose to stimulate at different amplitudes and frequencies to optimize stimulation.

In one multi electrode embodiment, the system utilizes temporal interference stimulation to get depth of penetration. High frequency stimulation from two electrodes can meet at the target depth without stimulating the intervening tissue. A first electrode stimulating at 3000 Hz, and a second stimulating at 3010 Hz, can meet at the target, interfere, and create a 10 Hz signal.

FIG. 1 is a mouthpiece example of a configuration of the stimulator system device previously described. The following mouthpiece stimulator 10 details may apply to all of the stimulation device form factors above, and more, and for example, may be powered by a battery, either rechargeable or not. Power for the stimulation system may alternatively come from radio frequency power source. The battery, RF power antenna, or energy harvester may be housed on the stimulator circuit 1 or separately within the mouthpiece 6 or separately in a mouthpiece extension 7, or a combination of these.

For a rechargeable battery power source, the recharging power may come from directly connecting the mouthpiece (or stimulator system) to a charger via multiple electrical charging contacts 8. The contacts 8 on the mouthpiece stimulator maybe the stimulator electrodes 2, or may be separate charging contacts 8. Alternatively, the battery charging may be accomplished via radiofrequency via an RF antenna connected to or integrated into the stimulator circuit 1.

Figure 2A:
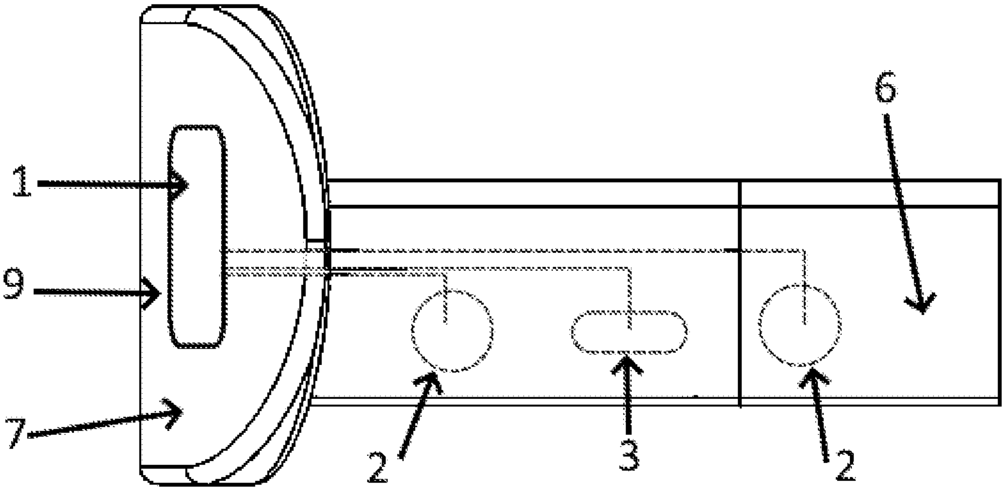
FIG. 2*a* is a partial perspective view of a mouthpiece portion and circuit of the present invention.
Figure 2B:
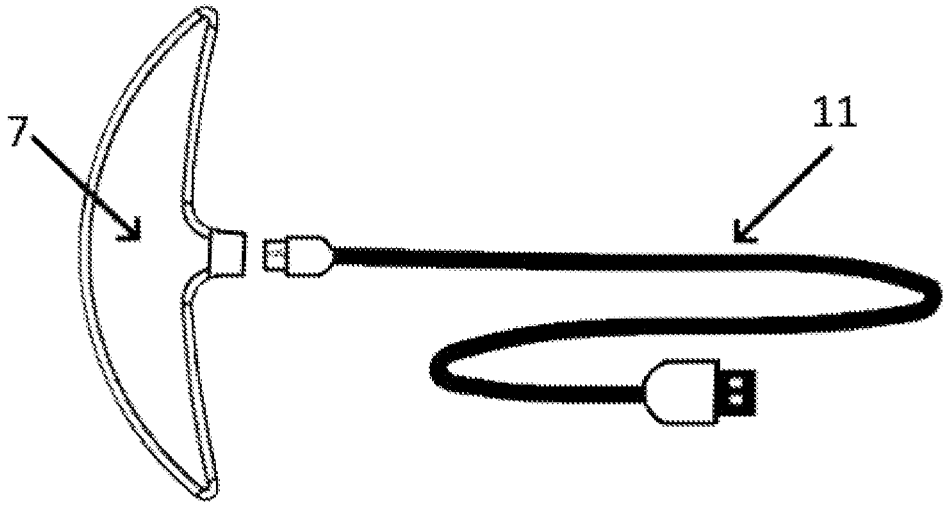
FIG. 2*b* is a partial perspective view of a mouthpiece and charging cable of the present invention.

Alternatively, as in FIG. 2, the stimulator circuit 1 may be removeable from the mouthpiece for charging, which is simplified if the stimulator circuit 1 is completely or mainly in a mouthpiece extension 7, such that saliva fluid leaking through connections is minimized. In this case the mouthpiece extension 7 may be unplugged from the mouthpiece 6, at which time the mouthpiece may be cleaned while the circuit in the mouthpiece extension is being charged.

The FIG. 1 stimulation electrodes 2 may be on the stimulator circuit 1, or wired to the stimulator circuit 1, or connected to an antenna which can communicate via RF with the stimulator circuit 1, or since at least two electrodes are preferred to complete the electrical stimulation circuit there may be a combination of ways that the electrodes may communicate with the stimulator. If a unipolar type configuration of a stimulator is used, the stimulator casing or part of the casing, may be used as one of the electrodes. All stimulation electrodes 2 may be used for stimulation and or sensing and or charging. An example of the latter maybe one in which the anode is part of the stimulator circuit 1 body, and the cathode is connected to the stimulator circuit 1 via an electrical wire, lead or cable. The number of stimulator electrodes 2 is at least one cathode or one anode, but more likely at least one of each, and most likely both anode and cathode may be in multiples. Each of the stimulation electrodes 2 may also be used as either anode or cathode, and may be of the same size, and different sizes. They may be of the same construction or of a different construction. As an example, the system may have 4 electrodes of the same or different size in differing locations as in FIG. 1. The patient or the system may select one of the stimulation electrodes 2 as the cathode(s) and the one or more of the others as the anode(s). The selection process may be automated based on system or patient feedback or be manually programmable by either a clinician or patient. Control and adjustment of the stimulation system parameters may be fully manual, fully automatic, or semi-automatic. Automated control may be time based or based on input from a variety of sensors 3. Sensors 3 may include electrophysiological and/or CSF flow rate measurement. Additionally, non-invasive measurements of autonomic nerve activity may be performed, including, blood pressure, galvanic skin response, heart rate, heart rate variability, and respiration variability. The device may include a phase modulation concept, where cycles of short waveforms cross different electrodes on the 'sensory nerve area of interest' to aggregate charge across the intended stim region while minimizing accumulation of charge on any nearby off target nerves.

Figure 11:
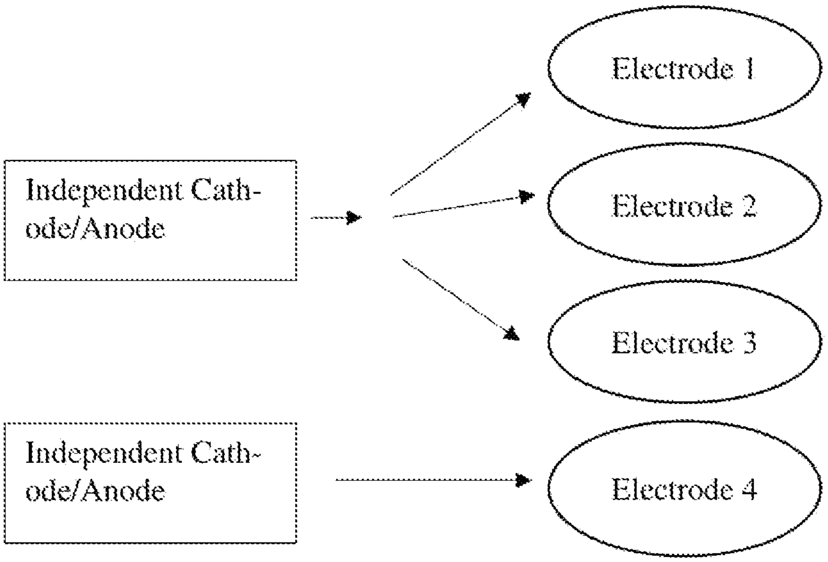
FIG. 11 is a chart of one electrical pathway for a stimulator system of the present invention.
Figure 12:
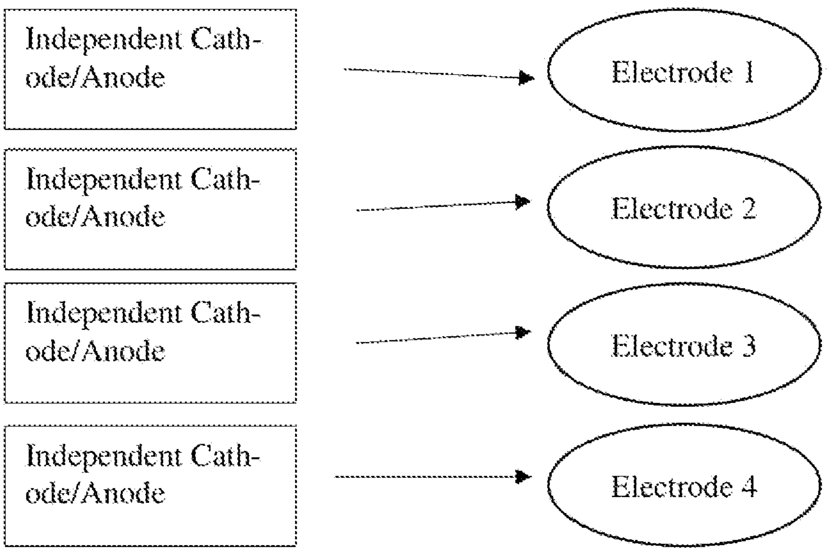
FIG. 12 is a chart of one electrical pathway for a stimulator system of the present invention.
Figure 13:
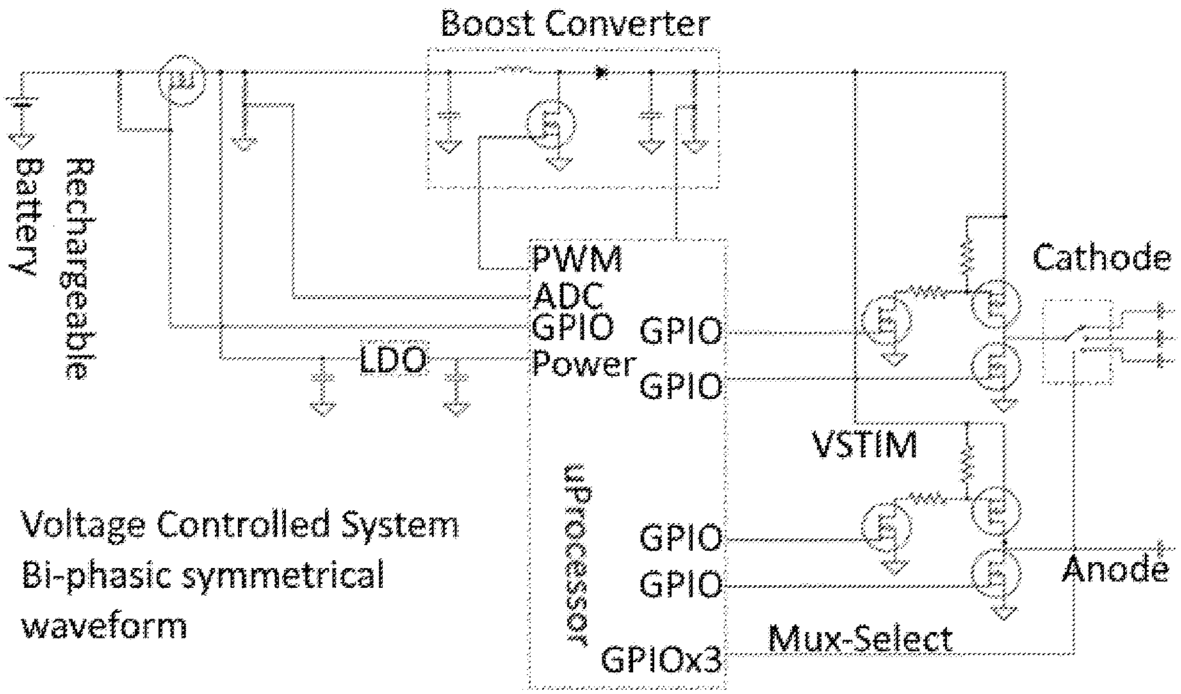
FIG. 13 is a diagram of a circuit for a stimulator system of the present invention.

The stimulation system 1 may be either voltage or current controlled. It may have an pulsatility output stimulation pattern of 10 seconds on and 10 seconds off, or 5 seconds on and 5 seconds off, or 5 seconds on and 30 seconds off, or similar. The pulse width may be 0.3 to 0.5 milli seconds, or more, or less. The stimulation frequency may be 1 Hz, or 10 Hz, or 100 Hz, or similar. The current output may be 0.1 milli amps, or 10 Milli amps, or 40 milliamps, or similar. The stimulation pattern may be a symmetric bi-phasic square wave form output, or a non-symmetric bi-phasic square wave form output, or a monophasic square wave, or a sinusoidal wave form, or a combination of these. There may be multiple stimulation electrodes. Only two of these may be used or multiple. There may be a switch to select and minimize the number of electrodes, as example FIG. 11 shows, or no switching may be done, as shown in example FIG. 12. A stimulator system circuit example FIG. 13 may log output and input data for latter downloading. The maximum voltage output of the stimulator may be as high as 3 volts, or as high as 9 volts, or higher or lower, but sufficient to give sufficient overhead. Electrode resistance may be around 10 ohms, or higher, or lower, with capacitance of around 10-15 micro-farads, or higher, or lower. The battery may be a single cell lithium polymer design with around 3.7 volts output, or similar and is designed to operate for at least 8 hours on a single charge, or at least 1 hour on a single charge. The output frequency may be approximately 100 hz maximum. The stimulation current may be around 10 milli amps and the circuit impedance around 500 ohms.

The trigeminal nerve is the fifth of twelve cranial nerves, and is responsible for recording sensations from the face and conveying them to the brain. It's a large three part nerve. There are two trigeminal nerves, one on each side of the body. In one embodiment the stimulator will stimulate one of the two nerves at a time. In another embodiment, the stimulator will alternate which nerve is stimulated. In still another embodiment the stimulator will stimulate both trigeminal nerves. The trigeminal nerve has three branches that perform distinct functions: Ophthalmic: This branch sends nerve impulses from the upper part of the face and scalp to the brain. Ophthalmic refers to the eye. The ophthalmic nerve relates to the eyes, upper eyelids and forehead. Maxillary: This nerve branch is responsible for sensations in the middle part of the face. Maxillary refers to the upper jaw.

The maxillary nerves extend to the cheeks, nose, lower eyelids and upper lip and gums. Mandibular: The mandibular (lower jaw) branch aids sensation to the lower part of the face, such as the jaws, lower lip and gum. These nerves also have a motor function. They help with biting, chewing and swallowing. The stimulator may seek to stimulate a portion of the mandibular trigeminal nerve, and as such will locate the stimulation devices toward the lower molars. In one preferred embodiment the stimulator stimulates the mental nerve, and or the buccal nerve, a sensory nerve that provides feeling to the lower lip, and is a portion of the mandibular branch of the trigeminal nerve, and or the lingual nerve. However, other arrangements are possible, including the upper molars, the premolars, or the bicuspid for stimulating the Mandibular trigeminal nerves, or the upper cuspids, incisors, or other teeth for stimulating the Maxillary trigeminal nerves.

In another set of embodiments the stimulator may seek to stimulate a facial nerve. The facial nerve is the seventh of twelve cranial nerves. It is responsible for controlling facial movement and expression, as well as taste and tears. The facial nerve has five main branches. The branches are: frontal (or temporal), zygomatic, buccal, marginal mandibular, and cervical. Frontal (temporal) controls the muscles of the forehead. The Zygomatic controls the muscles involved in forceful eye closure. The Buccal controls the muscles involved in moving the nostril, upper lip, spontaneous eye blinking, and raising the corner of the mouth to smile. The Marginal mandibular branch controls the muscles involved in depressing the lower lip. The Cervical controls the lower chin muscle (platysma), often tensed during facial hair shaving. It also lowers the corner of the mouth. Thus, the stimulator can provide stimulation to several facial nerves as well, in particular the buccal facial nerves. The stimulator can serve to stimulate multiple different nerves. For example, the lower back portion of the stimulator may stimulate the Mandibular trigeminal nerves while the upper portion stimulates the buccal facial nerves. The stimulator, or a second portion of the system, may stimulate the auricular vagus branch of the vagus nerve, which may also be a particularly good target for the invention.

The stimulator improves clearance during sleep of unwanted biomolecules from the brain that are generated during daily activities that ultimately impair learning, memory and concentration while increasing levels of stress and anxiety. These same pathways can be used to prophylactically prevent the onset of Alzheimer's Disease and Parkinson's Disease in subjects who are predispose towards these conditions as identified by several common biomarkers (hypertension, cholesterol, family history, etc.).

In one embodiment the stimulator is designed to be controlled by the end user. It may have a simple non-contact on off and power setting switches 5, such as magnetic switches. The switches 5 may also be of other types, such as capacitive, resistance, of other types of sensors. Alternatively, the switch 5 may be controlled by the user pushing a sealed button with a finger, or it could be also controlled by the user through biting. A first bite for on, another bite for off. The stimulator 10's on off functionality can also be controlled wirelessly. The device could have a simple power charger that charges a rechargeable battery 9 through two or more electrode type contacts 8, or an RF charging coil, or similar. One or more LED indicators 4 light up when the device is being charged. The charger 11 may also be used to turn the stimulator on and off. For example, when the stimulator senses that it is being charging, either through a plug in to mouthpiece extension 7 as shown in FIG. 2_b_, or via contact between charger contacts 8 and a charger, it can be programmed to automatically turn off, and then when it senses that it is not being charged it can automatically turn on, or at least turn on to sensing mode to look for appropriate impedances between stimulating electrode before beginning to stimulate. Some of the sensory capabilities mentioned have the potential for different functions to be considered. EEG can detect seizures or even seizure propensity to warn subjects (somewhat common with neural degeneration) to not drive a car, or in general to be cautious, etc. EGK pickup could detect cardiac abnormalities and give a warning via blue tooth, as an example. The sensors could also, as another example, detect a night time slip and fall walking to bathroom which are very common with dementia.

A mouthpiece is generally considered a protective device that covers the teeth and gums to prevent or reduce injury, especially to the teeth, and gums. However, as used herein the term includes non-protective devices that fit in the mouth but provide the circuitry described herein for stimulating nerves. The mouthpiece can be insulated to prevent electrical field escape, e.g., to nearby nerves. As bruxism is relatively common, the device may also protect against teeth grinding. In one embodiment it does so via use as a standard mouthpiece. In another embodiment stimulator 10 may be optimized to prevent grinding of teeth during sleep by detecting it and in a closed loop fashion, stimulate to minimize the bruxism.

Figure 3:
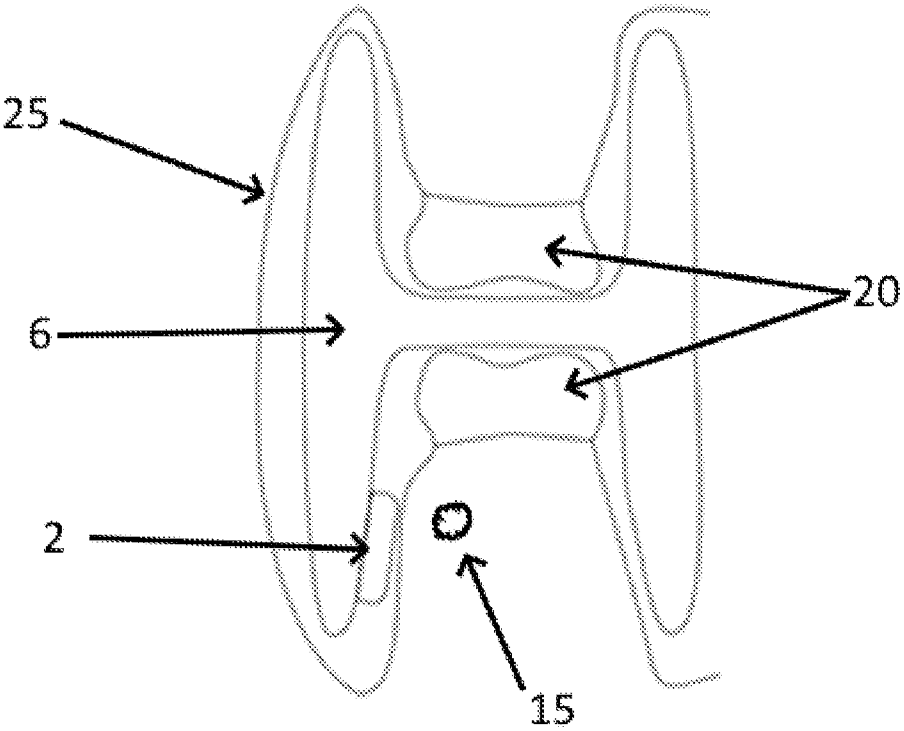
FIG. 3 is a side perspective view of a mouthpiece of the present invention.

The mouthpiece must have a base material that forms the shape and substance of the device. A mouthpiece is typically U-shaped, but as discussed below this is not required, the primary requirement for shape and form is that the stimulation elements be in proximity to the nerves targeted. The base material must hold the stimulating devices, or just electrodes, or electrodes and sensors, in the proper position for stimulating the target nerves. Commonly the mouthpiece includes at least one channel that is configured to receive at least one layer of teeth. That is, the mouthpiece wraps around at least one set of teeth, or a subset of teeth, to maintain its position. The mouthpiece may have layers that wrap around both sets of teeth as well, and thus has impressions for both the upper and lower teeth to fit into. The mouthpiece 6 may also have two portions, one to wrap around the upper teeth and one to wrap around the lower teeth 20, as in FIG. 3. The mouthpiece would fit between the teeth 20 and the gums 25. The two portions may be joined at one end or may be entirely separate. The mouthpiece 6 may contain or house the stimulator system 1 as in FIG. 4 or the mouthpiece may be attached to a mouthpiece extension, which contains the stimulator system 1, as in FIG. 1, or alternatively the stimulator system may be remote and powers the electrodes in the mouthpiece via a extension cable.

In other embodiments the mouthpiece may not wrap around teeth at all but may simply fit around them to place the electrodes or stimulation devices next to the target nerves 15. In those cases, there will need to be other means to hold the stimulation elements in position near the target nerves 15, such as a guard that sits outside of the mouth, with a nipple or probe that runs along the cheek to the target nerve. As in FIG. 7, the stimulator system 10 may also be attached to an adhesive electrode or electrode array 170 via mechanical connection, adhesive, or magnetic connection, and located in several other places on the head and neck which align with nerves identified in this application. As an example, the stimulator system may be attached to a strap or straps that wraps around the top of the head to form a headbands 180 or headbands 180 containing stimulator electrodes 2 and sensors 3, or hold leads running into the mouth, attached to the stimulator system 10. The headband example may be particularly beneficial for collecting EEG feedback. A headband version of the stimulation system could work in conjunction with or independent of a mouthpiece stimulator system, or other versions of the stimulator system, and communication between them may be directly through conductors, or via direct RF (Bluetooth, Wifi, LORA, LTE, GSM) connection, or via Bluetooth connection to a common device such as a cell phone. Another example is one in which the stimulator circuit 1 and power source are adhered under the chin, and communicates and powers electrodes and collects sensor data at the stimulator location at the chin or at the mouthpiece, or other locations as shown in FIG. 7. Connections between the stimulator system, electrode and sensors may either be direct through conductor leads, or via radio frequency. The stimulator system, electrodes and sensors may be in the mouth, on the scalp, on the forehead, on the neck, under the chin, on or in the ear, near the eyes, or anywhere the trigeminal, facial, or vagus nerves route. The stimulator may be also placed in a peripheral location on the body, and ideally located to engage a branch or a portion of the vagus nerve. In this case the stimulator may be included as part of a wrist worn watch, as only one of many examples. The stimulator may also stimulate the spinal cord stimulation (including sympathetic chain concept) to intervene with CSF at spinal cord, change sympathetic tone, change heart rate and blood pressure.

There are already several mouthpieces on the market for protecting teeth during sports, for protecting teeth from grinding during sleep, for reduction in snoring, for drug delivery, and for multiple other reasons. It is possible to combine these mouthpiece technologies with a stimulator to increase blood and CSF flow. This could be accomplished with a combination product, where the system could be separate but easily attachable to the other product. In the simplest form of the latter, a very low profile stimulator device, which is attachable to a mouthpiece, may consist of only an antenna and a pair of electrodes. Such a device could be attached to a mouthpiece or another device in the mouth which holds it on place (like a retainer), a replacement tooth, or it may be designed to be held in place on its own, or be attached to another device which holds it transdermally next to a described nerve, or the low profile electrodes and antenna could be injected or implanted next to a described nerve. To energize this most minimal antenna and electrode pair stimulator configuration, a transmitter antenna will need to be placed within appropriate proximity to the stimulator antenna. The transmitter antenna may be placed on or near the patient. For instance, the transmitter antenna could be placed on or in the patients bed or pillow. Alternatively the stimulator could be adhesively attached under the chin, or other part of the body close to the implanted antenna and electrodes. The transmitter antenna may also be part of a piece of patient clothing.

Figure 27:
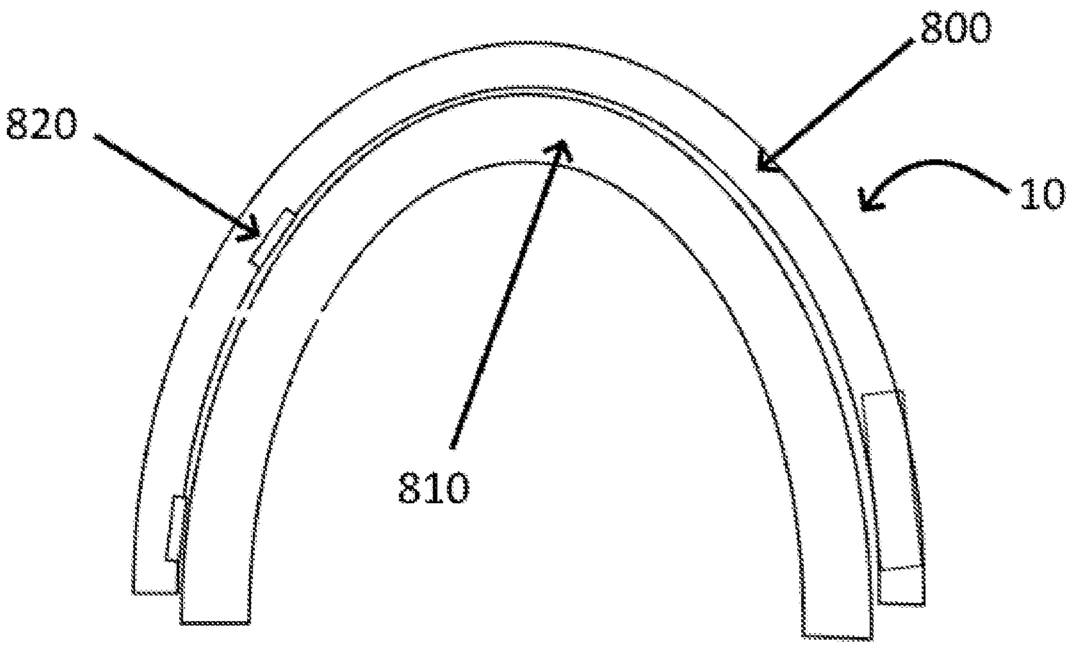
FIG. 27 is a partial perspective view of a mouthpiece of the present invention.

The waste clearance stimulator may be made in the form of a tooth or teeth, or may be attachable to a tooth or teeth, such that only a partial mouthpiece is necessary. The stimulator may also be in the form of a strip 800 that is placed between the gum and the lips as in FIG. 27, and may be kept in place simply by how it sits between the inside of the cheek and the gums. It may also be held in position with a tooth clip, partial retainer, or similar means. The strip type stimulator maybe in a u-shape, forming around the entire jaw, or a strip meant to be placed on only one side of the jaw. The strip type design may also be adhered to other oral devices 810, such as a retainer or OSA mouthpiece, for stabilization.

In this fashion the stimulator may be combined with other products on the market, and the electrodes 820 may be adjusted to optimally place the electrodes over the tissue/nerves by how the strip is adhered to the oral device that it is attached to. The mouthpiece or partial mouthpiece or tooth clip or strip between lips and gum may have a minimal level of electronics, and may only be an antenna or stimulator connected to a pair of electrodes. The minimal electronic designs may be powered or controlled by an antenna which is on or near a patient.

Figure 28:
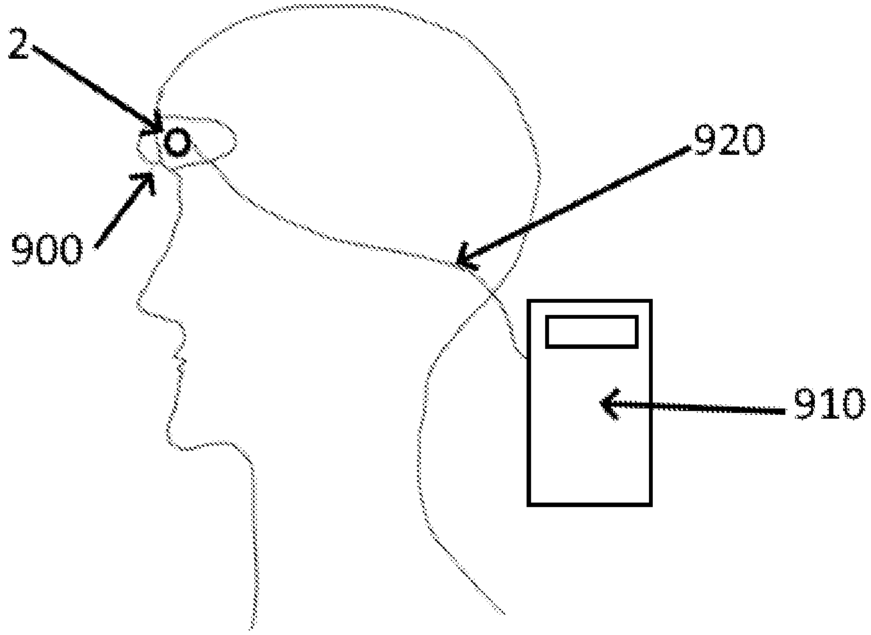
FIG. 28 is a partial perspective view of a stimulator system of the present invention.

An example of a transdermal solution of the invention may be accomplished by, for example, stimulating the V1 branch of the trigeminal nerve. The electrodes could be held in one or more transdermal electrode patches which adhere to the skin. As in FIG. 28, the stimulator, in part or in whole, may be directly attached to the electrode patch(s) 900 or the stimulator may be contained in part in a remote device 910 connected via an electrical conductor 920 to patch 900 having electrodes 2, or the electrode patch may have a built-in antenna and be stimulated via a nearby RF transmitter source, such as under a patients pillow (not shown). In one example the stimulator is attached directly to the electrode assembly as in FIG. 7. Alternatively, the electrode assembly is attached to a stimulator via a cable or wire, such that the stimulator maybe on a belt, on a nightstand, or similar. Stimulation of the V1 branch of the trigeminal nerve has some advantages. For instance, a product that stimulates the V1 branch may also have EEG sensors to measure sleep stage and specific oscillatory neuronal activity, both of which may be used as inputs to the stimulation system as to which stimulation algorithm to use and also the specific time to apply the stimulation.

In some embodiments, e.g., for treating stroke or traumatic brain injury the stimulator is paired with one or more learning tasks to facilitate brain plasticity. The system may include a configuration that involves sensory pairing during the day to increase plasticity, paired with a "replay" stimulation at night to reinforce that plasticity, which is interweaved with a stimulation to increase overall blood flow and clearance. The stimulator system could be learning from readings taken during the day, using a preset stimulation pattern, or using a "replay" stimulation at night to reinforce the plasticity. These stimulation patterns may be interleaved with a stimulation to increase overall blood flow and clearance.

Method of Fitment & Calibration

A method for custom fitment and calibration may be done by a clinician or by the patient, or user. This fitment and calibration may include shaping the device, and alignment of electrodes and or sensors, and including adjusting stimulation parameters, and sensing parameters, for each patient. Shaping the device for proper comfort and functionality may be necessary for the initial use, and reshaping may also be necessary as effectiveness of the initial fitment may change over time. Optimizing alignment and positioning of electrodes and sensor may initially be done with simple techniques such as sensing the location of nerves in tissue. Additional in office or at home techniques for calibrating the device maybe accomplished through the use of EEG feedback, and or retinal arterial pulsation data, and or similar techniques. The data may be used to determine if a patient is responding to treatment, and may help calibrate settings initially, or regularly, or after several months of use. Similarly, PET scans may be used to determine responders and the level of increased CSF flow, or a surrogate for CSF flow increase. Surrogate measures for CSF flow could include sleep studies to determine time in a particular sleep stage, or EEG measurements, or chemical measures, or retinal artery pulsation. Also, calibration of the entire stimulation cycle may be done at the time of initial fitment.

As initial stimulation may need to be lower or not at all, to allow the patient to fall asleep, temporal input/output parameters may need to be customized for each user. The stimulation may start at a very low level before the patient falls asleep, and then increases once sleep has been detected through various sensors 3. Ramping stimulation energy to increase threshold before side effects is used even during awake stimulation.

Figure 20:
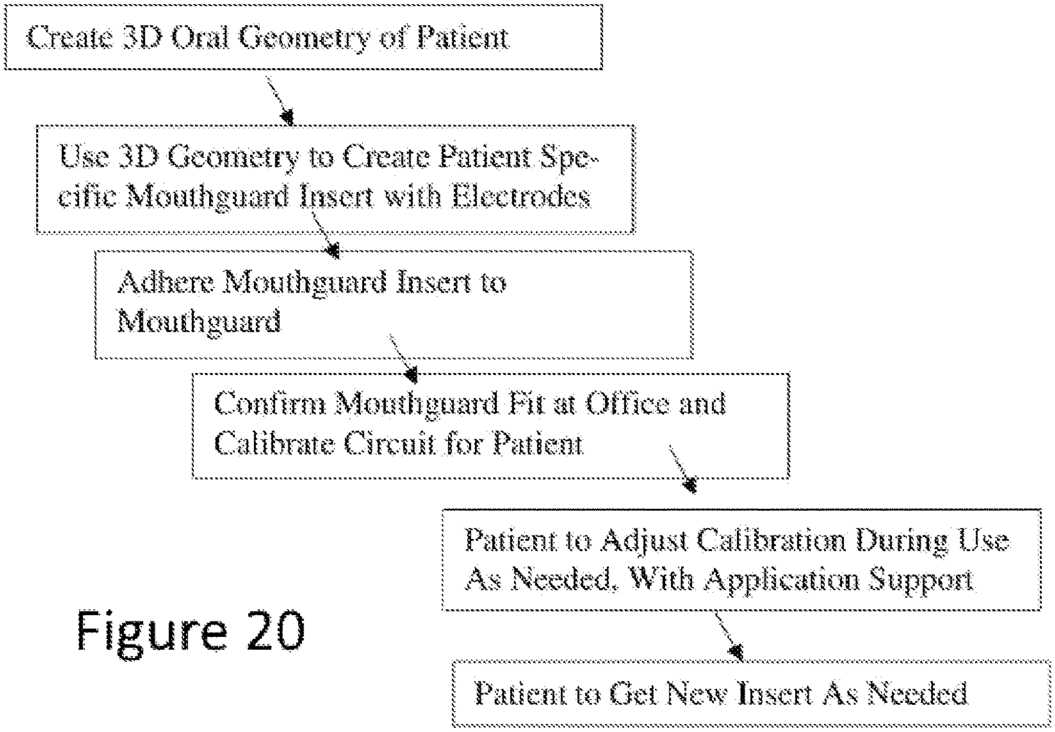
FIG. 20 is a flow chart of the method of using a stimulator system of the present invention.

The device may be fit to the user in several ways. First, as in FIG. 20, the user may get a 3D mouth scan from a dentist office or similar. The 3D scan may be from a specialized laser or ultrasound mouthpiece scanner, a specialized handheld wand laser scanner, multiple x-rays, or a cone beam CT scanner, or similar. The 3D image will then be used to configure and build the user's custom 3D printed mouthpiece, including patient specific electrode positions. Stimulator probes and sensing probes may be used to determine the most appropriate locations within the mouth for the stimulation electrodes and sensors. Other imaging techniques like MRI scanning may also be used for imaging for creating a custom mouthpiece. Other options may rely on dental offices, but not necessarily exclusively. Those other options for creating custom fitting mouthpieces are, mouthpieces formed from customer wax or polymer impressions, or from customer formed mouthpieces. The latter are believed by the inventors to give 90% of the electrode position accuracy of the custom mouthpieces created from CT or laser data.

The 3D printed version may not only custom fit the mouthpiece to the teeth, but also fit the electrodes to the optimal locations over the nerves, and at the appropriate distance from the gum or check tissue. The 3D printing may be done in such a way that the electrodes are printed into the mouthpiece during printing, such that most of the mouthpiece is printed from a relatively electrically insulative material, while electrode are printed in specified locations, per user needs. The 3D printer may also create the slots for the conductor wires or slots flexible circuits between the stimulator and the electrodes, and may also create the attachment point for the stimulator system, such as a detent, hook or snap feature. The latter may also be skipped if the stimulator is placed out of the mouth and energizes the electrodes via RF or conductor cable. If RF stimulation energy is used then a RF antenna is incorporated into the mouthpiece. These custom molded or printed mouthpieces are ideally made of a ridged moisture resistant polymer material like PEEK, PMMA, or a heat-cured acrylic resin like EVA that will hold its shape over time. Like sports mouthpieces, a thicker (e.g., about 2 mm or more) flexible membrane formed from a moisture-resistant polymer material is needed. In a preferred embodiment, the layer comprises a mixture of ethyl vinyl acetate and polypropylene. According to another embodiment, it may be formed of a polyolefin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes or polyesteramides, polyethylene (PE), high density polyethylene (HDPE), low density polyethylene (LDPE), ultra low density polyethylene (ULDPE), polypropylene, and polytetrafluoroethylene (PTFE). Plasticizers, UV Stabilizers, flow additives, and fillers known in the art can be used as desired to modify the properties of any of the foregoing polymers. The mouthpiece, will need to be rigid to keep its shape over time, hold its position in the mouth, and protect the electronic circuitry. It also needs to be flexible, comfortable, resilience, and cushioning, result in a layer that is relatively thicker, preferably having a thickness ranging from about 2 mm to about 5 mm, more preferably from about 2 mm to about 4 mm, and most preferably from about 2 mm to about 3 mm. This allows for use of a thinner mouthpiece, which is also more comfortable to wear for the user.

Second, alternatively, the initial fitment may be done via an at home fitment process, where the customer forms an impression and sends it to a company who then creates the custom form factor of the mouthpiece, such as commercially on the market devices for dental aligners, retainers or anti-snore guards. The user takes a set of molds to create dental impressions at home. The user then sends in the molds to the entity that will create and send the aligners. While the CT scan may provide better electrode positioning, specifically over the left mental foramen or buccal nerve or nerve endings with patient specific accuracy, this method is anticipated to be 90 percent accurate, and much more cost effective for the user. To increase this electrode positioning accuracy the spacing between electrodes may need to be increased.

Figure 4:
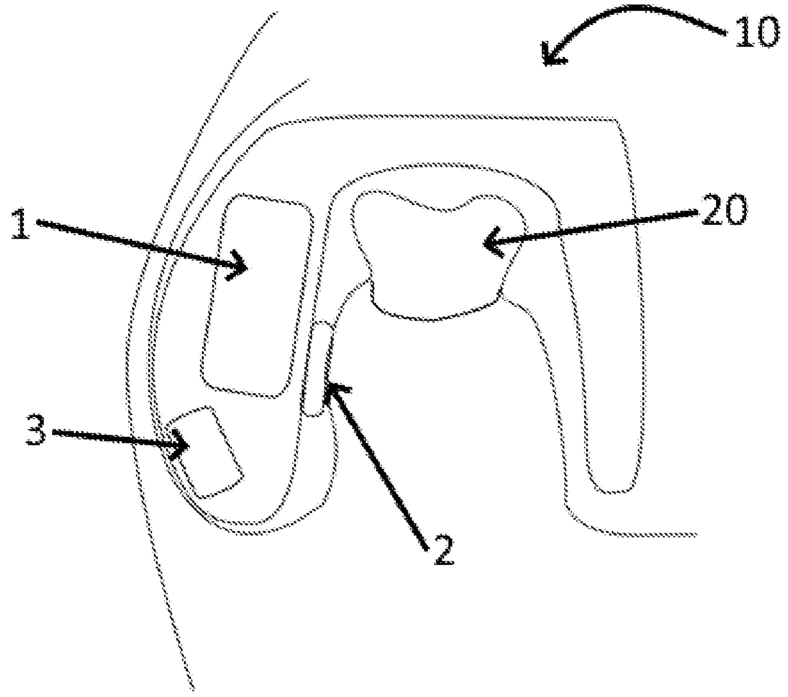
FIG. 4 is a side perspective view of a mouthpiece of the present invention.
Figure 5:
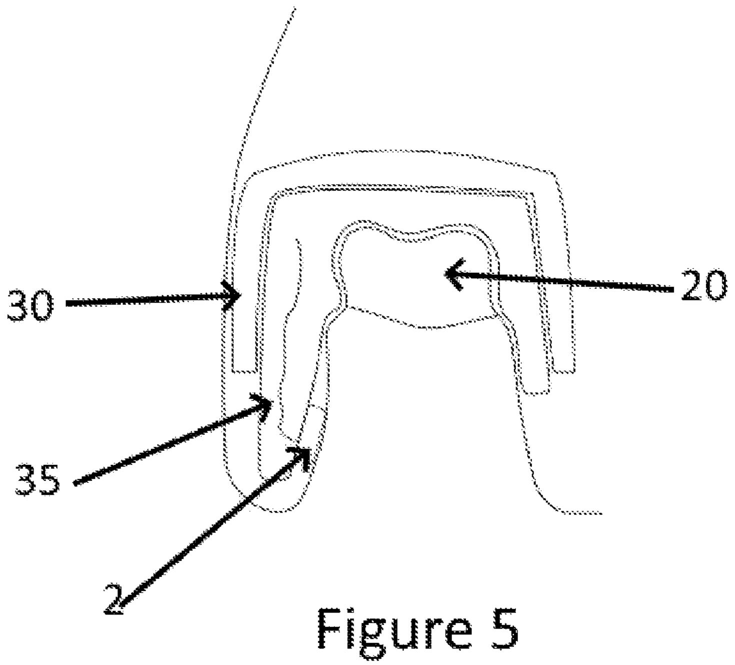
FIG. 5 is a side perspective view of a mouthpiece of the present invention.
Figure 6:
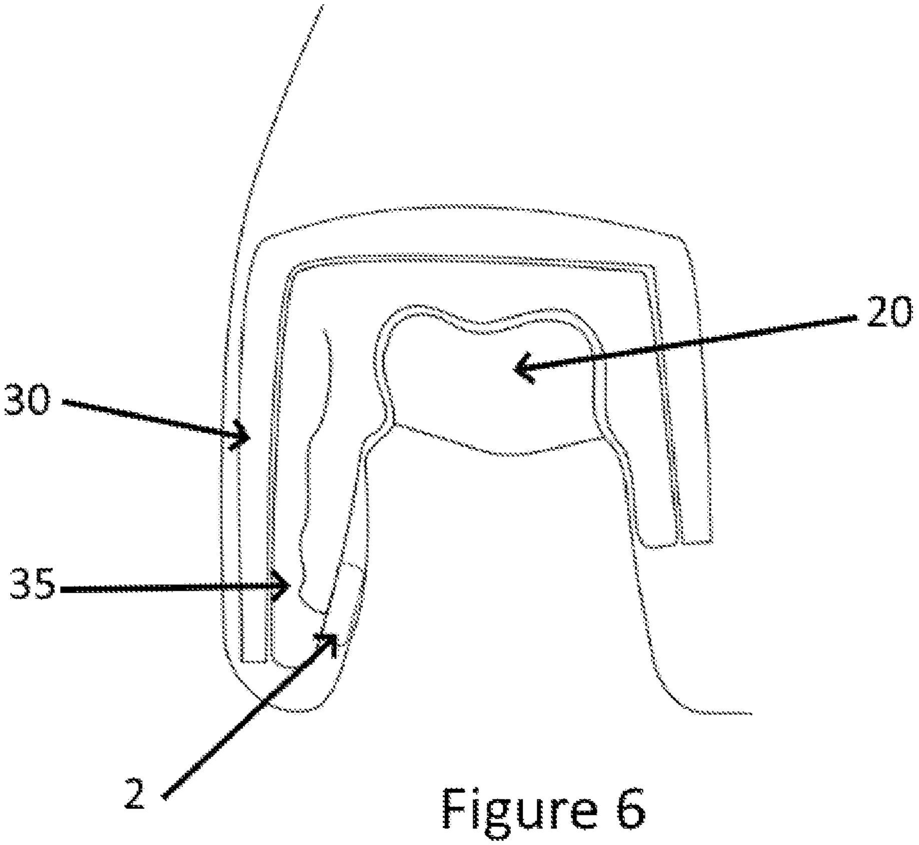
FIG. 6 is a side perspective view of a mouthpiece of the present invention.

Third, FIG. 5 is another embodiment in which the user or patient would self-fit or form the device around the teeth, gum, mouth, in what is known as a "boil and bite" method, similar to off the shelf sports mouthpieces. This device type such may be made of a rigid or semi rigid structure 30 like epoxy, or Delrin, or glass, or ceramic, or metal (e.g. titanium, stainless steel), which could contain most of the circuit and sensors as in FIG. 4, and a less rigid conformable polymer 35 component bonded to the rigid structure and circuit, or just bonded to the rigid structure. The rigid component may extend down to past the electrode as in FIG. 6, allowing more controlled and firmer contact pressure between the electrode and the gum, or the rigid polymer may not extend over the electrode, as in FIG. 5, such that the fit between the electrodes and sensors is more conformable. The less rigid polymer may be made of EVA, or similar polymers which have a glass transition temperature below the boiling point of water, or polyurethane, or a hydrogel such as Hypan hydrogel from Hymedix International, Inc., Dayton, N.J. Other hydrogel materials which are contemplated by the present invention include com-pounds such as polyhydroxy ethyl methacrylate, chemically or physically crosslinked poly-acrylamide, polyvinyl alcohols, poly(N-vinyl pyrolidone), polyethylene oxide, and hydrolyzed polyacrylonitrile. The device may ship with multiple electrode pairs, and the customer then selects the best electrode pairs for their custom use through a manual protocol or through the use of a closed loop system. The closed loop system could be integrated fully into the stimulation system, wherein, for example, a sensing system looks for proper electrode impedance and cycles through multiple electrode pairs until impedance is optimized. Alternatively, electrode positions and stimulator output may be adjusted based on other sensor data. If available for initial setup, arterial plurality or CSF flow may be measured by MRI, CT scan, x-ray, diffuse optical imaging, magnetoencephalography, PET, single photon emission computed tomography, or other brain imaging modalities. Likewise, the user may answer a set of testing questions, quality of life questions, or the like on a cell phone to understand if the stimulation is giving a positive cognitive impact.

In most cases the device should be fit to the user. Even in the case of a probe, the probe must be sized to reach the proper position. In the case of the embodiments that wrap around the teeth, while a standard size may be used, it is preferred that the mouthpiece be fit to the specific teeth and mouth of the user due to comfort and stability.

As mouthpieces are commonly worn during sleep, the inventors herein have developed a novel mouthpiece that can be personalized to an individual's anatomy to activate the facial and trigeminal nerves at barely perceptible and imperceptible levels during sleep. Once fit to a person's anatomy, they can be repeatably placed by the user, placing the electrodes easily and exactly every time relative to the nerve they prefer to stimulate. Furthermore, the mouthpiece electrodes will tend to hold their precise placement during sleep while the patient moves around during sleep. A mouthpiece implementation is also favorable for placement of the electrodes with relatively low stimulation capture levels considering that it is non-implantable. This is due to the facts that the mouth is a continuously wet environment, and the nerves are not deep in the tissue. This means that stimulation levels can be very low and without or minimal impact on other tissues or non-target nerve fibers. The mouth is a space or cavity where many types of devices have been place successfully to help patients sleep. These include mouthpiece to prevent snoring or the grinding of teeth.

In choosing a mouthpiece for a user, the user's sleeping style may be considered. The fit of the mouthpiece may vary if a user sleeps with his mouth open verses closed, and if so a biasing agent may be employed, such as a spring, hinge, or the like between a top and a bottom portion (if the mouthpiece has both portions—in some embodiments only one portion is present) to allow the mouthpiece to move with the user's mouth opening and closing without losing contact with the gum tissue, cheek, or other tissues. A user who sleeps on one side may place additional pressure on that side of the mouthpiece, either ensuring appropriate contact between the electrodes and tissue (i.e. gum and or cheek), or inappropriate contact do to the electrode moving away from the target position. Biasing agents may be added to preserve the positioning of the electrodes. For example, when the right side of the mouthpiece is under pressure, the top portion may pinch, driving the electrode in a desired direction, e.g., down. Likewise, the pressure that pushes into the right side may cause the left side to rise if the front portion of the mouthpiece is too stiff, and as such the left side may need to be biased back into place.

Biasing agents may also keep electrodes where they need to be with respect to the nerves, to achieve an acceptable level of electrical impedance and nerve capture, even as the device structure and shape changes slightly over time. For instance, mouthpieces are often made of a stock U shape of ethylene vinyl acetate copolymer (EVA) or equivalent polymer, such as polyethylene (PE), polypropylene (PP), and polybutylene (PB). This polymer may creep over time, changing its shape. But if the electrode or electrode support structure is design to accommodate these changes while maintaining originally fitted electrode position relative to the nerve then the user and system will not need to make corrections for these changes. The device may be designed so if the appropriate amount of mechanical biasing does not correct impedance sufficiently, then electrical measures maybe taken, such as increased output amplitude. The electrical changes may be automatic or through prompts from the cell phone application. If the impedance is not correctly and safely corrected then the stimulation may not begin, or may be terminated, with an error communicated through indicators on the devices and or through the cell phone application.

As some users will shift to different positions at night, the mouthpiece may need to have multiple biasing agents to ensure a proper fit. Of course, having multiple electrodes allows the system to sense which electrodes are in optimal position at any given time and sleeping position, and adjust the stimulation accordingly. The sensing to determine electrode position may be done through multiple modalities, including resistance, impedance, pressure, optical, electromagnetic positioning, etc. The system can then eliminate electrodes from the stimulation circuit as needed. The system may also be set to decide which electrodes are the anode versus cathode. The system may also decide to group multiple electrodes in parallel for the anode part of the circuit, depending on inputs from one or more sensing modalities.

In one embodiment of FIGS. 1 and 4, the stimulation electrodes are in contact with the inside of the cheek, such that specific fit of the mouthpiece to the teeth and gums is less necessary, since the conforming tissue of the cheek may place a consistent electrode contact distance and pressure on the cheek tissue. In this case, as an example, the targeted nerve may be the buccal nerve in the cheek. The device may have appropriate electrical insulation such that the electrical stimulation is precisely delivered to the target tissue. For instance, if the target is the mental nerve in the gum of the mouth, the cheek side of the device may have electrical insulation to minimize electrical stimulation of that tissue. Similarly, electrical insulation, such as polyimide, polyurethane, or similar may be at the edges of the electrodes on the gum side to focus electrical energy to a specific target. In other embodiments the electrode itself is made of a conforming material, or shaped to create more tissue-electrode surface contact. The electrode may also include an embedded steroid to keep the stimulation site viable.

Figure 10A:
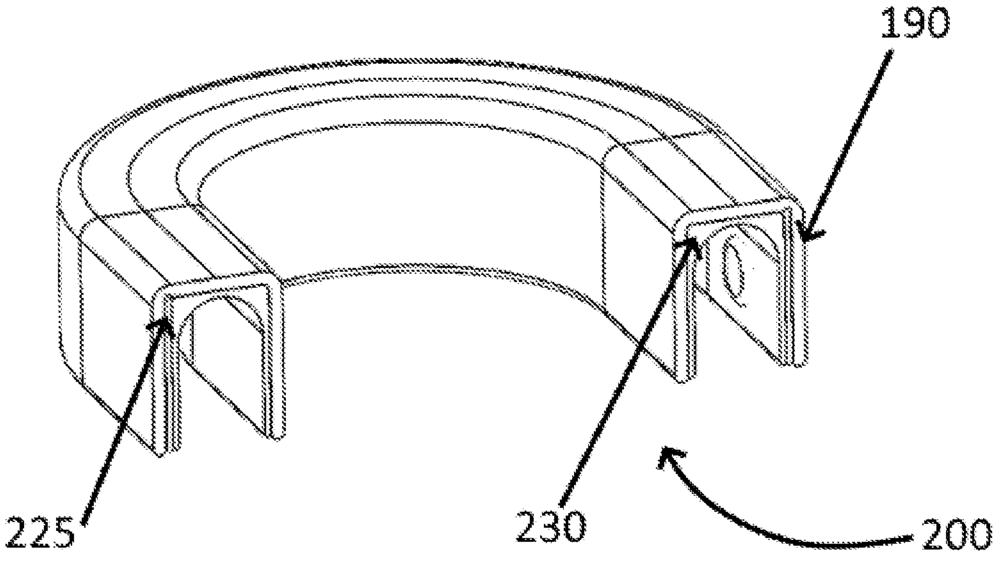
FIG. 10*a* is a partial perspective view of a mouthpiece of the present invention.
Figure 10B:
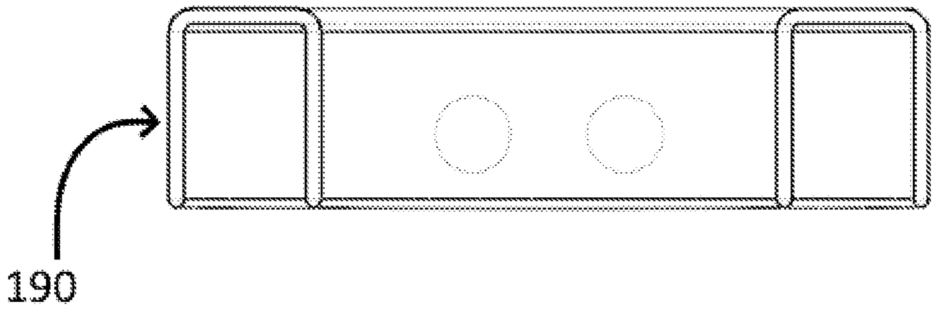
FIG. 10*b* is an exploded perspective view of a portion of the mouthpiece of FIG. 10*a;*
Figure 10C:
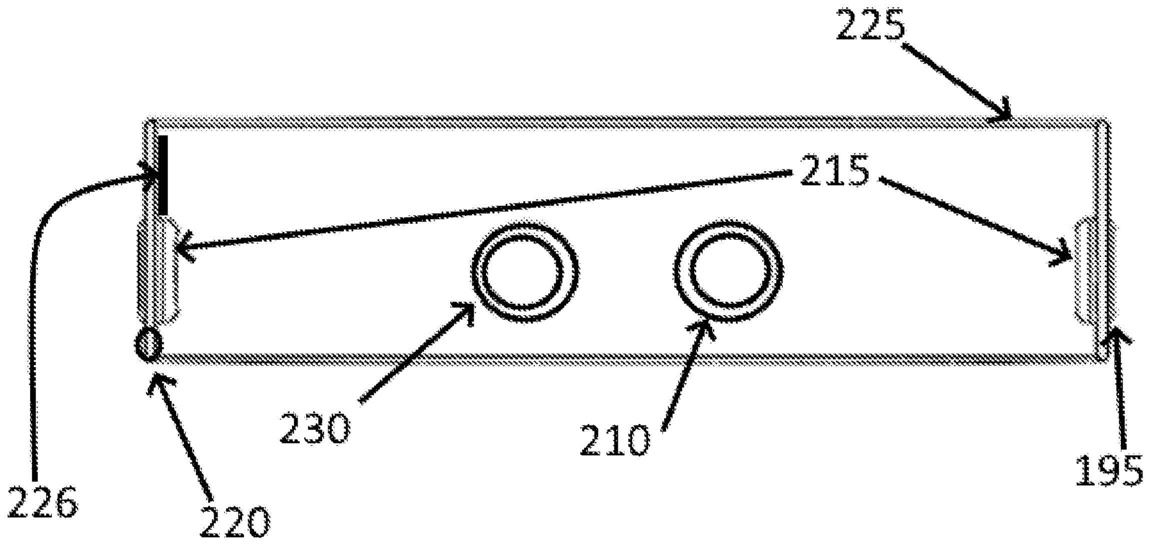
FIG. 10*c* is an exploded perspective view of a portion of the mouthpiece of FIG. 10*a;*
Figure 10D:
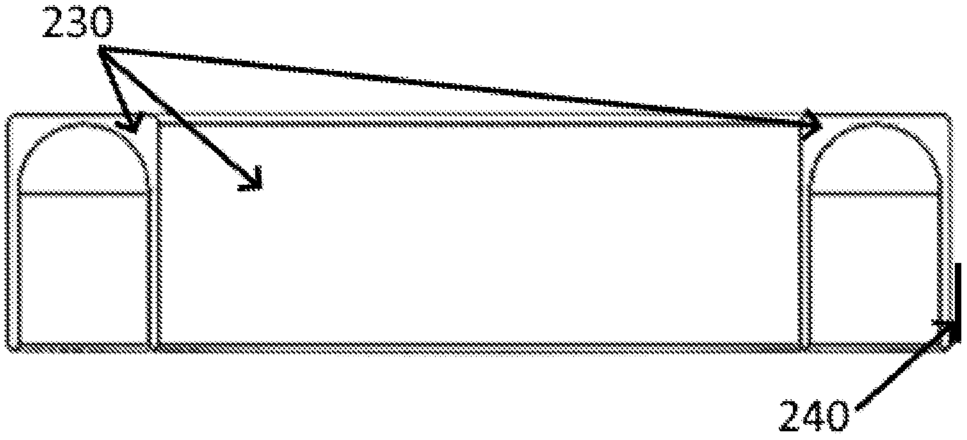
FIG. 10*d* is an exploded perspective view of a portion of the mouthpiece of FIG. 10*a;*

FIG. 10*a* is an embodiment of the mouthpiece 200, and is made up of three main components as shown in FIGS. 10*b-d*, and FIG. 25. First, a rigid shell 190 is made of a polymer that has a glass transition (Tg) temperature that is higher than boiling water such as PEEK, PMMA, or a heat-cured acrylic, epoxy, or a glass reinforce epoxy laminate such as FR4, or a ceramic material, or a metal material (e.g. titanium, stainless steel), or composites or polymer and ceramic, such that it holds its shape when placed in boiling water, for "boil and bite" formation. The rigid shell 190 may be of a general U shape like in most mouthpieces, or other shapes as necessary to hold the stimulator in an appropriately repeatable position. The rigid shell 190 may or may not also have slots or channels for an electrical circuit 225. The rigid shell 190 may or may not also have a slot for the custom shaped component 230. The rigid shell may have a variety of other slots, holes and other features for sensors, electrodes, switches, indicators, connectors. The rigid shell 190 may be made of two or more shell structures that can be joined together, by welding or gluing or similar joining techniques, such that the electrical circuit 225 maybe hermetically sealed within the rigid shell 190. The rigid shell 190 may have conductive elements molded or pressed into it, or placed or placed after molding or machining, to allow electrical communication between the circuit and electrodes or sensors in the custom shell 230. Similarly, the rigid shell may have optically clear materials between the electrical circuit 225 and the custom shell 230, to facilitate optical stimulation and or sensing. A second component, an electrical circuit 225, may be in the form of a flexible circuit, which may fit into the rigid shell slot, and be sealed from moisture. The electrical circuit 225, with battery, may be on a rigid board, a flexible board, or be made of a combination of flexible and rigid boards, or the electrical circuit 225 may be integrated into the custom shell 230 component by component, without a flexible of rigid board. The electrical circuit 225 may contain or hold an RF coil 226 for charging the battery, may contain or hold sensors 195, electrodes 215, switches 210, indicators 220, connectors, charging contacts 230, and be shaped in such a way that it may fit into or onto the rigid shell 190. A third component, a custom shell 230, may or may not be add, and may or may not be used to give the mouthpiece a better fit. The custom shell 230 may be 3D printed, molded or machined to fit the patients teeth, gum, and mouth, and be made of a hard or soft polymer, or other material. The custom shell 230 shape may also be shaped through the "boil and bite" shaping process, in which case the polymer of the custom shell 230 and, or, the custom shell electrode(s) are made from a polymer that has a glass transition temperature less than boiling water, including polyurethane, such as pellethane, polypropylene, polyethelene, ethylenevinylacetate (EVA), or another elastomeric plastic, and may be initially injection molded, machined, 3D printed, or made via another manufacturing process. The custom shell 230 may have electrodes 240 and or sensors or sensors openings that align and contact the circuit electrodes 215, and or are made to align with and contact electrodes 215 on the electrical circuit 225, and the electrodes may be made of an electrically conductive material, such as stainless steels, platinum, gold, carbon nanotubes, silver, copper, or composites where the matrix material is a polymer, or another metal, which holds the conductive materials such as carbon nanotubes, conductive metal flakes, and coatings such as DC-plated platinum black, sonico-plated platinum black, Pt-nanograss, NanoPt coating, gold nanowires, nanoporous gold, Au nanoparticles, Graphene, PEDOT, Polypyrrole SIROF, EIROF, AIROF, nanoporous AIROFs, IrOx/Pt gray, and IrOx/Pt gray-coated metals and conductive polymers. The custom shell electrodes 240 may be printed into the custom shell 230 at the time of 3D printing of both, or they may be molded together, machined together, or made separately and then assembled. The circuit, rigid shell and custom shell may be thermally bonded, or bonded with adhesives, which are conductive or non-conductive, depending on what components are being adhered by one skilled in the art. The custom shell electrodes that are made of composites may or may not be conformable and compatible with the "boil and bite" shaping process, as in some cases it may be optimal for them to conform to the shape of tissues for a close fit, and in other cases a precise shape of the electrode may be more important. The rigid shell 190 and the custom shell 230 may be printed during a single printing session, of different polymers, of different polymer durometers, and with or without electrodes.

The size of the stimulation electrode(s) may be at least 0.05 mm in effective area, or up to at least 10 mm in effective area, or no more than 1000 mm in area. Attachment of the custom shell 230 to the rigid shell and electrical circuit 225 components may be a snap or interference fit, or the attachment may be a thermal bond, or the attachment may be completed with an adhesive. In any case, if an adhesive is used, an electrically conductive adhesive may be used between electrical contacts. In one embodiment of FIG. 10 the custom shell 230 and the rigid shell 190 are made or 3D printed as one piece, with a slot or cavity which the electrical circuit 225 is dropped into, connected, and then sealed from moisture. The electrical circuit 225 may be housed in a hermetic case.

In a preferred embodiment, the electrode placement is optimized using one or more methods. For instance, the buccal nerve is located along the back molars and the cheek. Accordingly, if the buccal nerve is targeted, the electrodes would be placed along the cheek or gum on the outside of the lower jaw and by below the back molars. In one method, a user's CT, MRI or other 3D scanning techniques can identify the exact nerve pathway and the electrode may then be placed along the path of the nerve, or at the nerve ending, or at a node, or particularly concentrated intersection. In the case of the 3D printed mouthpiece the electrode can be directly printed into the polymer at that location. In another method, pooled data from past users of the device type will inform the best position for the electrodes to target the nerve. In this approach electrode locations that provide the optimal effect on blood and CSF flow are prioritized as initial settings future devices and future users. In yet another method, multiple electrodes are used, or mobile electrodes that can be moved within the device, and based on feedback through a closed loop the device determines the optimal electrode location.

In another embodiment, electrode optimization requires two devices. A first device is a measurement device. The measurement device includes electrodes or other stimulation elements. The measurement device may further include a means to measure one or more of the arterial pulse, the CSF flow, respiration cycle timing, cerebral slow wave (delta) pulsation timing, blood flow, oxygenation, etc. The device may have many more electrodes than the mouthpiece will have. The measurement device is employed in or around the mouth, and various stimulation patterns and electrodes are used to stimulate the target nerves. Measurements are taken of the desired metric, and the optimal electrode location is then determined. Optionally, a scan of the mouth anatomy, such as an MRI, ultrasound, or CT scan, may be employed as well. The mouthpiece is then built accordingly. For transcutaneous stimulation adhesives like hydrogels loaded with carbon fibers may be used to reduce impedance to extend battery life.

Electrode Details

In many of these embodiments, it is preferable that the electrodes be conformable to the anatomy of the user to provide a consistent stimulation surface, give more stimulation options, or a more accurate or more targeted delivery of the stimulation, keep power consumption low, and not wake the patient. The electrode may be preformed around the shape of the anatomy. For example, an electrode may be preshaped based on typical anatomy to match the tooth shape, gum shape, or the cheek shape. If a mold or a CT scan is available, the electrode may rely on that data to be preshaped.

In another approach, the electrode, or the electrode supporting material, may be flexible, and in use would conform itself to the anatomy of the user, or to that of the mouthpiece which may itself be conforming to the user. Conformable electrodes can be formed of polymers, particularly conductive polymers, a 2D or 3D stretchable metallic wire structure, a wired patch held together by a coating, thin metals, silicon based electrical components, flexible circuits, thin materials (that are flexible due to their slight thickness), and the like. It is also preferable that the electrode be stretchable in many situations, and that it be biocompatible, or be encapsulated by biocompatible material.

In one embodiment the device includes a biasing agent that will press the conformable electrode into the gum, cheek, or other desired surface, causing it to conform to the shape of the area targeted. Biasing agents include springs, nitinol wires, expandable or inflatable materials, soft polymer, fluid chamber, gas chamber, foam materials, and the like.

The electrode can also be heat activated, such that when the mouthpiece is boiled the electrode is flexible at elevated temperatures, but as the mouthpiece cools it becomes hardened, or a cross linking (or curing) process begins resulting in a resilient electrode shape. The electrodes may be structured or have a roughened surface, by use of coatings like PEDOT or Pt-Black, or titanium nitride (TiN), or iridium oxide (IrOx), or laser structuring, of mechanical roughening, increasing the effective surface area and lowering impedance.

In one preferred embodiment the stimulation device is actually a series or grid of electrodes. For example, the stimulation device can include a plurality of spot electrodes. The software can then choose the ideal portion to use for stimulation. In another embodiment the electrode is shielded on one side to direct the stimulation out away from the teeth and into the nerves.

The electrodes could be made of a solid piece of machined or molded platinum or platinum alloy or they could be made of another metal like a type of stainless steel or the electrodes may be made of carbon particulate, silver nanowire (AgNW), or nanotube imbedded in a hard or soft polymer matrix material. The electrodes may also be of thin film material such as those on flexible circuits, and the flex circuit may be conformable. The flexible circuit substrate maybe made of a thermoset like polyimide, or may be made of a thermoplastic like polyurethane. The thermoplastic substrate may have a glass transition temperature low enough that it softens when placed in boiling water, such that the electrodes conform to the surface of the gum tissue when a "boil and bite" design is implemented. The electrode form may be designed and made in such a way that it may be custom fit to the customers gum or tissue shape. The mouthpiece may be made, at least in part, of a soft polymer such that the mouthpiece can be placed in boiling water, then removed, and then the patient bites into the softened polymer to form and fit the mouthpiece to the patient. The electrodes listed above may be in the soft polymer and conform to the patients tissue shape along with the polymer that the mouthpiece is made of. If the mouthpiece is self fit using boiling water, known as "boil and bite" the circuit container would need to be able to withstand boiling water or be detachable from the mouthpiece during softening of the soft polymer prior to forming. The electrodes or sensors are fit to the rigid polymer structure or the soft polymer structure. If they are fit to the rigid polymer the fit would need to be relatively precise or have a biasing feature such as a spring feature to make up for any imperfections during fitting or change in shape over time. The electrodes or sensors may also be placed into the soft polymer.

Conformable electrodes, or conformable polymer holding electrodes, may be designed in multiple form factors and used in multiple ways, and combine with non-conformable electrode designs. Examples of some of these are, first, the "boil and bite" design, such that electrodes, or electrode holding polymers, are made to conform to a particular tissue shape when the electrode or polymers holding the electrode is warmed, and then set to a conforming shape when cooled, and second, the conformable electrode, or conformable electrode holding polymer, may be of a design which is not thermally set in a conforming shape, but rather remains "actively conformable", meaning that it has a standard manufactured shape, but which conforms to the users tissue shape each time it is used, and third, a conformable electrode may be partly of a "boil and bite" design, such the user shape is mostly thermally set, but the electrode still remain at least partly "actively conformable", such that any mismatch in electrode and tissue shape may be minimized, and forth, the three previously mentioned designs may be combined with non-conformable electrodes, and all of the above maybe combined with a clinician fitment. An example of the latter maybe one in which initial fitment of the device to the patient is done by taking a 3D data set of the mouth and then custom shaping the device, including or not including shaping of the electrodes, and having the device design be of a form factor such that the electrode(s) or electrode supporting materials adjust to optimize electrode to tissue alignment over time. Examples of conformable electrodes are found in those of wearable electronics, such as wearable organic photovoltaics (WOPVs) for self-powered electronic skins, human—machine interactions, real-time health monitoring, internet of things, which require a strong and comfortable adhesion that conforms to skin movement without compromising their performance. Among different flexible transparent electrodes, silver nanowires (AgNWs) are perceived as the promising for their low percolation threshold, and high electrical conductivity, and excellent flexibility, combined with a matrix material of polyethylene terephthalate (PET) the electrode may be made smooth and flexible. However, the plastic polymer substrates, such as PET, polyethylene naphthalate (PEN), perylene, and polyimide (PI) with Young's moduli of 2.8-6.1 Gpa or more, elastic polymers such as polydimethylsiloxane (PDMS), polyurethane (PU), and polyurethane acrylate (PUA), all of which have a similar Young's modulus to the human body and are more conformable. Hydrogel loaded with carbon fibers or other may be included to help conformance, especially for ear bud or headband versions (which will also alter the interface less during sweating).

Conformable electrodes, or electrodes supporting structures, may be made of any highly elastic material, with electrode conductive materials being held within. These could be, for example, a flexible circuit with a polyurethane substrate with copper electrodes which are plated with noble metals and copper conductive traces of a serpentine shape to provide them stretchability. Alternatively, a machined platinum iridium electrode could be attached to a copper wire and embedded in, or molded into, a highly elastic polymer, like polyurethane, and the polyurethane may have air bladders to enhance active shape conformance between the electrode and tissue.

Alternatively, the device may not be conformable at all, but rather preshaped or custom shaped for each user at or prior to fitment. Electrodes could be shaped to contact tissue, or they may be recessed into the device such that they do not contact tissue, but rather, since the mouth is a moist environment, saliva is relied upon to be a conductive means between tissue and electrode. In this way electrode irritation of tissue may be minimized.

While the inventors contemplate the use of electrodes for stimulation, this is not the exclusive means of stimulating the blood vessels. Ultrasound stimulation, in particular collimated ultrasonic beams, in the presence of a magnetic field, can induce a current by Lorentz forces as the tissue is conductive. Thermal waves, mechanical vibration, acoustic waves, pressure waves, optogenetic stimulation using light to stimulate nerves, magnetic stimulation to produce electric currents via electromagnetic induction, temporal interference (multiple, especially high-frequency, electric fields that only cause activation where they overlap), are also possible stimulation mechanisms, as discussed above.

Small implantable or non-implantable electrodes, or electrodes with antennas, may also be placed closer to the nerve, such that the stimulator device may use lower power to stimulate. The electrodes may be made of solid conductive metals, metal particulate dispersed into a polymer or other matrix material, or carbon nanotubes. The electrode assembly could be designed to only contact tissue on the gum, only on the check, or both. An example of a design which contacts both is made similar to implantable pacing leads, which are made of polymer tubes, conductors and metal ring electrodes. The metal ring electrodes may sit in or close to the cheek and gum connection point, such that the ring electrode is in contact with both check and gum.

Stimulator Circuit

Portions of the device's electronics have been discussed above. Turning to the electronics in detail, the device will include a power source, a circuit, one or more electrodes, and optionally a sensor or sensors. The power source is typically an internal battery, but an external power source is also possible, particularly in the case of the probe, or if the mouthpiece is a part of a larger system. The battery may be rechargeable, replaceable, or the device may be considered disposable. The battery may be rechargeable through contacts via placement in a charger. The device may have RF charging of a rechargeable battery or be powered via RF under or in the pillow of the sleeping patient. In another embodiment, the electrode is actually an RF antenna, and receives RF energy from outside the user, generating a current in the antenna for stimulation.

The device may have a way of saving the battery by shutting off when not in use. For example, the circuit may include a clock, and be programmed to be off during the day, and on during the night. In one embodiment the mouthpiece has a simple non-contact on off and power setting switches. Alternatively the switch may be controlled by the user pushing a sealed button with a finger, or it could be also controlled by the user through biting. A first bite for on, another bite for off. Sensors may also control the power delivery, as for example sensing saliva, tissue impedance or capacitance, tissue temperature, the device may begin the power delivery. The device will further have a circuit for controlling the delivery of power. In the most basic sense, the circuit will be programed to deliver the power—in particular to an electrode or to another stimulation device—according to one or more algorithms below. The circuit may further be capable of receiving input from one or more sensors, measurement assemblies, or diagnostic elements as described below, and may be capable of altering the power delivery based on analysis of those inputs. Impedance of the stimulation circuit will be measured prior to and during stimulation delivery, via DC measurement, by having the system generate a very small constant current (10-50 uA) and measuring the resultant voltage drop across the body, which is commonly used in tDCS (transcranial direct current stimulation). Alternatively, measurements of the current/voltage at the end of the pulse can be made. Alternatively, measurements of the voltage drop at the end of the pulse can be made. Any of these may be used to adjust the stimulator output power.

The circuit will typically include a modulator for modulating the power deliver, or the carrier wave's amplitude according to a desired signal or stimulation level. In a simplest configuration, the modulator passes the signal without modification during a first stimulation period and turns off the signal during a second period. The modulating signal may be a discontinuous waveform such as a pulse or square wave. As is understood in the art, signal modulation by the modulator may provide an envelope of the signal peaks, the peaks being of much higher frequency than the rest of the signal. The signal may also be a smooth curve. By interleaving stimulation with periods of rest, recovery processes of the glymphatic, neural activity, and meningeal lymphatic system may be accommodated to allow greater clearance. This is also more natural, so may alter glial response in a positive way (continuous stimulation likely causes glia to change a lot due to the non-natural metabolic demand). Glial cells are responsible for maintenance of the extracellular space, and release gliotransmitter to damp down burst of neural activity that cause a flood of ATP/Ca/Lactate, etc. into the extracellular space. In essence triggering the glial cells to damp down the neural activity, but care is taken to not drive them too hard and overdrive their response (which may change them into an inflammatory phenotype). Similarly, for neurovascular coupling mediated changes in blood flow, care is taken to not overdrive the metabolic demand in a limited supply situation.

In one aspect the mouthpiece can include a plurality of sensors, measurement assemblies, and diagnostic elements. Exemplary sensors would include electrodes. In this aspect, it is contemplated that these devices can be spaced around the mouthpiece, or placed at particular locations useful for that device. A saliva sensor may be placed on the interior of the device so that it can be where saliva is most plentiful.

Many sensors, and typically the electrodes are spaced from one another about the mouthpiece, and configured for contact with a portion of the mouth of the user, including the gums, cheeks, lips, palate, and tongue of the user. At least one electrode may be positioned over the mental branch nerve. At least one electrode may be positioned over the inferior alveolar nerve, or lingual nerve, or buccal nerve.

The sensors can be a part of the mouthpiece itself, but can also be a part of an associated device that is in communication with the mouthpiece, the external charging station, or another device, such as a cell phone. Many users utilize a smart watch which has various sensors, and the mouthpiece may connect via blue tooth to the smart watch to use the data generated. Likewise, many users rely on a CPAP machine at night, and it may connect with the mouthpiece to exchange data.

In a preferred embodiment the device includes an external input mechanism. This could include a Bluetooth connection, RF connection, wired connection, or a connection through a charging station. The external input mechanism is a mechanism that allows a user to input control commands, or download data and information from the device. In particular, the external input mechanism allows a user or a doctor to adjust the power delivery, stimulation levels, stimulation duration, time of day the power is delivered, electrode position, sensor inputs, or other portions of the device. For example, the user's cell phone may establish a blue tooth connection with the mouthpiece. The cell phone can be programed to turn on the mouthpiece at the same time it enters into a sleep mode for the evening, or based on a user input on the cell phone. A reader or a cleaning case may have its own SIM card or other connection, and may be used for similar purposes. Likewise, the cell phone may be used to adjust parameters. In one embodiment a remote user, such as a doctor or technician, may communicate through a cell phone, or a docking station, with the mouthpiece and adjust the parameters. The mouthpiece can be turned on and off by sensor data (such as capacitive or impedance data), or through RF communication (with software in an application on a cell phone or computer), or through a switch (like a mechanical bite switch, or capacitive or impedance switch, temperature switch, or any of the previously mentioned sensors), or through a combination of two or more of the above, such that the battery does not become drained inadvertently.

The external input mechanism is particularly useful if the mouthpiece has a broader stimulation power range, as this allows users to more carefully tune the stimulation parameters to the user's needs. It may also be designed in such a way that allows the electrodes to be tuned and positioned more carefully to meet the user's needs.

Figure 18:
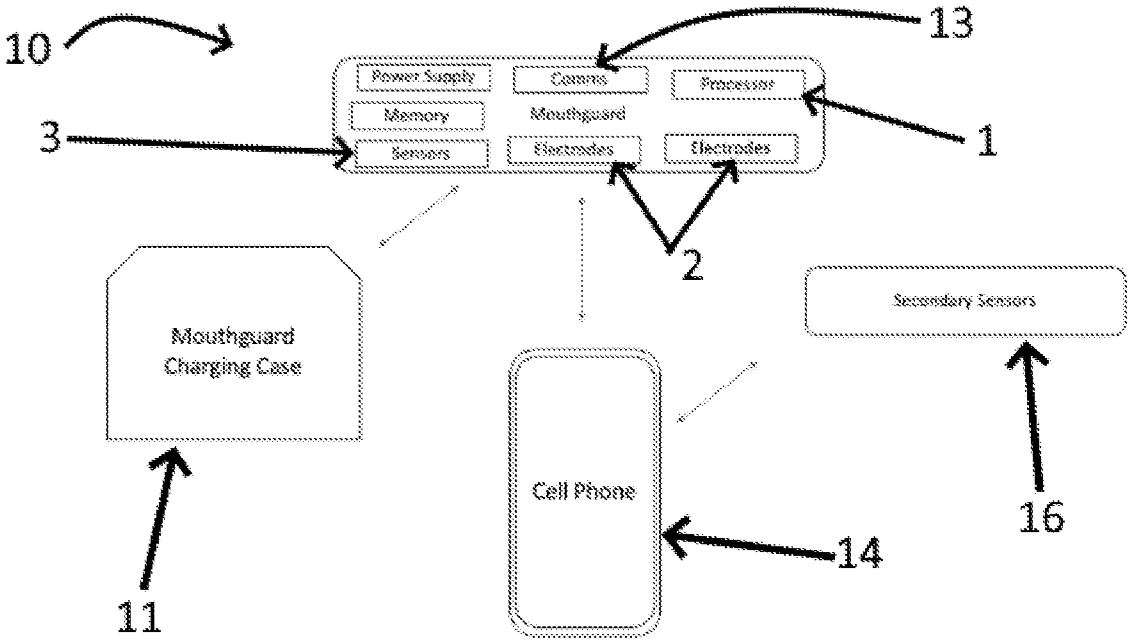
FIG. 18 is a diagram of a stimulator system of the present invention.

A preferred embodiment of the product is shown in FIG. 18, which shows one embodiment of a mouthpiece, an associated remote device 14 which communicates with mouth guard 10 through communications module 13 on the mouthguard, as well as with secondary sensors 16. The remote devices are described above, but can include a user cell phone with a custom control application, an associated external charger case, and additional secondary sensors on the cell phone or an auxiliary device such as a watch, monitor, or other set of sensors. Sensor feedback paths could be contained within the stimulation system, or include other devices like watches, cell phones, or other equipment. Information from one portion of the system is fed into a controller in the circuit. The controller is then used to compare the output of the system, and or the data from the sensors, etc., to the desired result, and adjust the stimulation accordingly. The controller maybe preprogrammed or user programmed, or clinician programmed, or the program may be adjusted using machine learning techniques as in FIG. 21. The stimulation output of the device may be at least partly dependent on one or more of temporal measures, sensor data, user input, controller calculation, and clinician inputs, to optimize therapeutic benefit or minimize side effects or maximize patient safety.

The stimulation system may measure electrode impedance to determine how well it may be in contact with tissue. The impedance data could be processed within the stimulator system and the power delivery is adjusted to compensate for the distance sensed, or a different electrode could be automatically selected, based on set or adjustable algorithms. This type of adjustable algorithm could be in a cell phone application rather than on board within the stimulator system, or it may be in both locations. In order for this automated, semi-automated, or manual adjustments to be made the stimulator may need to communicate at least in part with a device like a cell phone, or an intermediary or interface device like the charger, which acts like a signal booster or amplifier. In other systems, the CSF flow is sensed, or reported, and one or more portions of the power delivery (amplitude, stimulation levels, duration, etc.) is again adjusted to achieve optimal or desired CSF flow.

Figure 14:
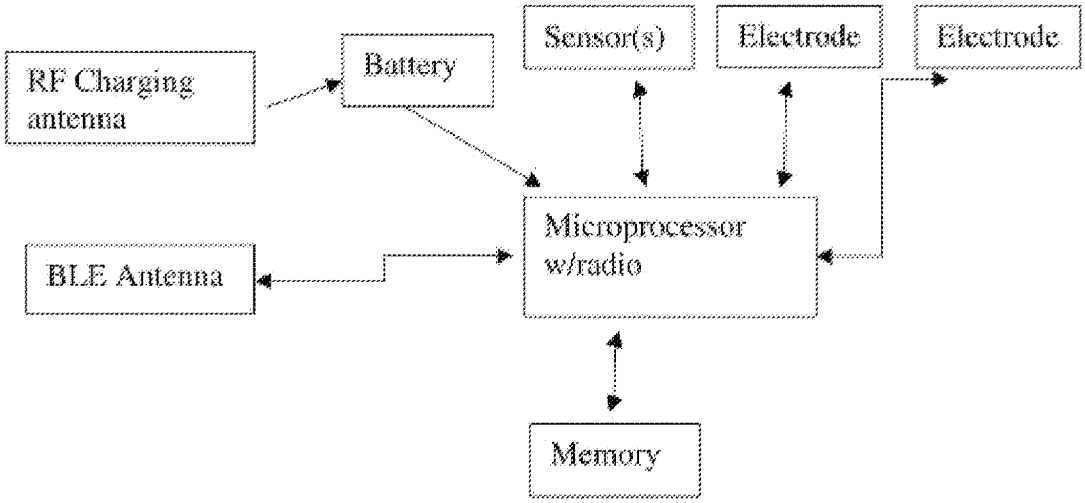
FIG. 14 is a diagram of a circuit for a stimulator system of the present invention.

An example block diagram of the stimulation circuit FIG. 14 shows a microprocessor. The circuit may include or may not include a microchip like a 555, or a FPGA, or a CPLD, or similar. The microprocessor contains or is connected to memory, a battery, and a Bluetooth radio and antenna. The battery is connected to an RF coil antenna for charging. The microprocessor is also connected to two electrodes and possibly at least one additional sensor.

Figure 8:
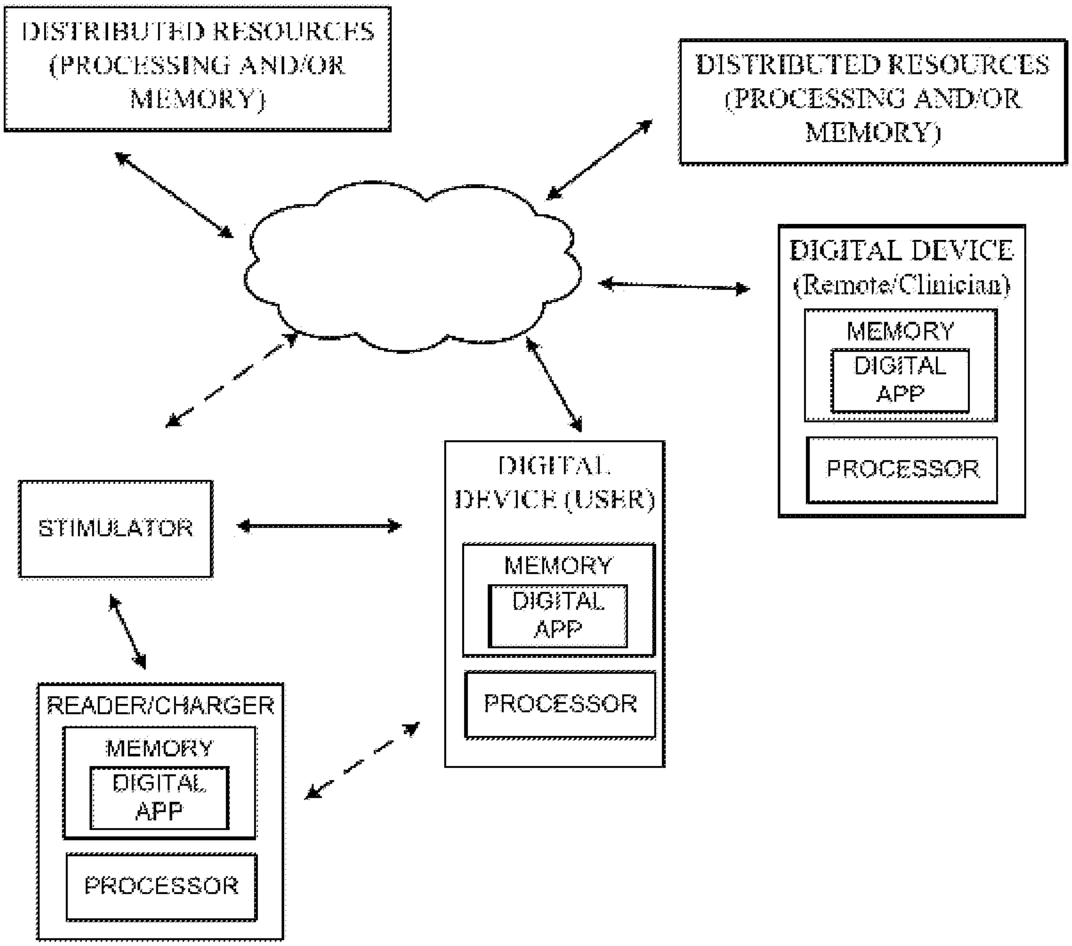
FIG. 8 is a diagram of a method of using the stimulator system of the present invention.

FIG. 8 illustrates another example system which includes a plurality of digital devices that wirelessly communicate over a local network (e.g., Bluetooth, radio, wi-fi, etc.) and, optionally, over a second network (e.g., Internet). For example, the plurality of digital devices may include devices located locally with respect to an environment of the user (e.g., wearable or otherwise associated with the user), which may be referred to as “local devices”. Example local devices include the stimulator, reader/charger, and a digital device associated with the user (e.g., smartphone, Holter monitor, watch, other wearable), sometimes herein referred to as “a local digital device”. The system may optionally include a plurality of remotely-located and/or distributed digital devices, such as cloud distributed processing and memory resources. In some exam-pies, the system further includes a remotely-located digital device, such as a digital device associated with a clinician.

As shown, each of the various devices may include a processor and memory. Each memory may include a computer-readable storage medium storing a set of instructions and other data, such as digital application(s) and/or machine learning models or other types of data models. Example computer-readable storage medium includes Read-Only Memory (ROM), Random-Access Memory (RAM), Electrically Erasable Programmable Read-Only Memory (EEPROM), flash memory, a solid state drive, Electrically Programmable Read Only Memory aka write once memory (EPROM), physical fuses and e-fuses, and/or discrete data register sets. In some examples, computer-readable storage medium may be a non-transitory storage medium, where the term “non-transitory” does not encompass transitory propagating signals. The processors may be a central processing unit (CPU), a semiconductor-based microprocessor, a graphics processing unit (GPU), a microcontroller or other type of controller, special purpose logic hardware controlled by microcode or other hardware devices suitable for retrieval and execution of instructions stored in the non-transitory computer-readable storage medium, or combinations thereof. In addition to or alternatively to retrieving and executing instructions, the processor may include at least one IC, other control logic, other electronic circuits, or combinations thereof that include a number of electronic components for performing the function.

In various examples, the local digital device associated with the user may communicate over the network (illustrated by the cloud) with a remotely-located cloud resource (e.g., processor or server) of a cloud system to download a digital application from a database. The cloud system may include a plurality of remotely located processing resources and memory resources. The digital application may include a machine learning model which is trained based on inputs for similar users to the user. The local digital device may execute the digital application to ask for patient feedback or other questions, as described above, cognitive test, provide data from the stimulator to external digital devices or cloud resources, among other functionalities. In some examples, the local digital device may download the trained machine learning model and communicate the same to the stimulator or to the reader for controlling stimulation provided to the user. In some examples, the stimulator communicates sensed data to the local digital device which communicates to the cloud processing resource via the digital application and network. The cloud processing resource(s) adjust or retrain the machine learning model over time, and communicate the adjusted or retrained machine learning model back to the local digital device.

Reader/Cleaner/Charger

A reader such as a custom digital pad 14 with a memory housing a digital software application may be specifically designed to be used to directly or indirectly connect to the stimulator circuit. This reader may also be the stimulator controller but will be referred to in this section as a reader. In this way the setup, use, and security for the entire system is simplified. The reader may be used to control or adjust stimulator 10’s settings. The reader may communicate with the stimulator 10, the cloud, computers, and the charger via electrical conductor wires, or through Bluetooth, Wi-Fi or similar radio methods. The reader may also collect and process data from the stimulator, from the readers environment, or from other devices in the patients environment or in or on the patient, secondary sensors 16, or from local or over the web data bases. The reader may transfer data to and from the stimulator or the cloud or devices such as cell phones, or other connected devices. The reader may be used to enhance user compliance and adherence. The reader may be in the form of a handheld digital tablet, a computer, a smart watch, a smart ring, a smart phone or similar, or a module that plugs into such a device. It may also be part of or connected to other components of the system, such as the charger or cleaning case. The reader may have the same or similar custom digital application software that may be downloaded to other digital devices, or since the reader is designed and sold specifically to interface with the stimulator part of the system, it may have different digital application software. The digital application software on the reader may be the same software that is on the as that available for uploading onto a smart phone, and may operate in a similar fashion. However, since the digital application software needs to 1) link with another system component, like the stimulator, such that the stimulator can upload data to the software, and download settings, and 2) allow the user, caregiver, or collaborator the appropriate and efficient access to view the data, collaborate, and manage settings, it is important that the system be easy to use, and especially for the elderly patients who may already have some form of dementia. For this reason, a custom reader may be preferred over the same software on the patients smartphone or digital tablet. The reader may enable patient control, charging, cleaning, and data transfer via Bluetooth/Wifi to Cloud, of on-board and connected sensor data, including Bio-feedback, Actigraphy, COGs Test Results, Sleep Score, seizure frequency, tremor frequency, Apnic frequency, Adherence, Electrode Apposition to name a few.

Figure 9A:
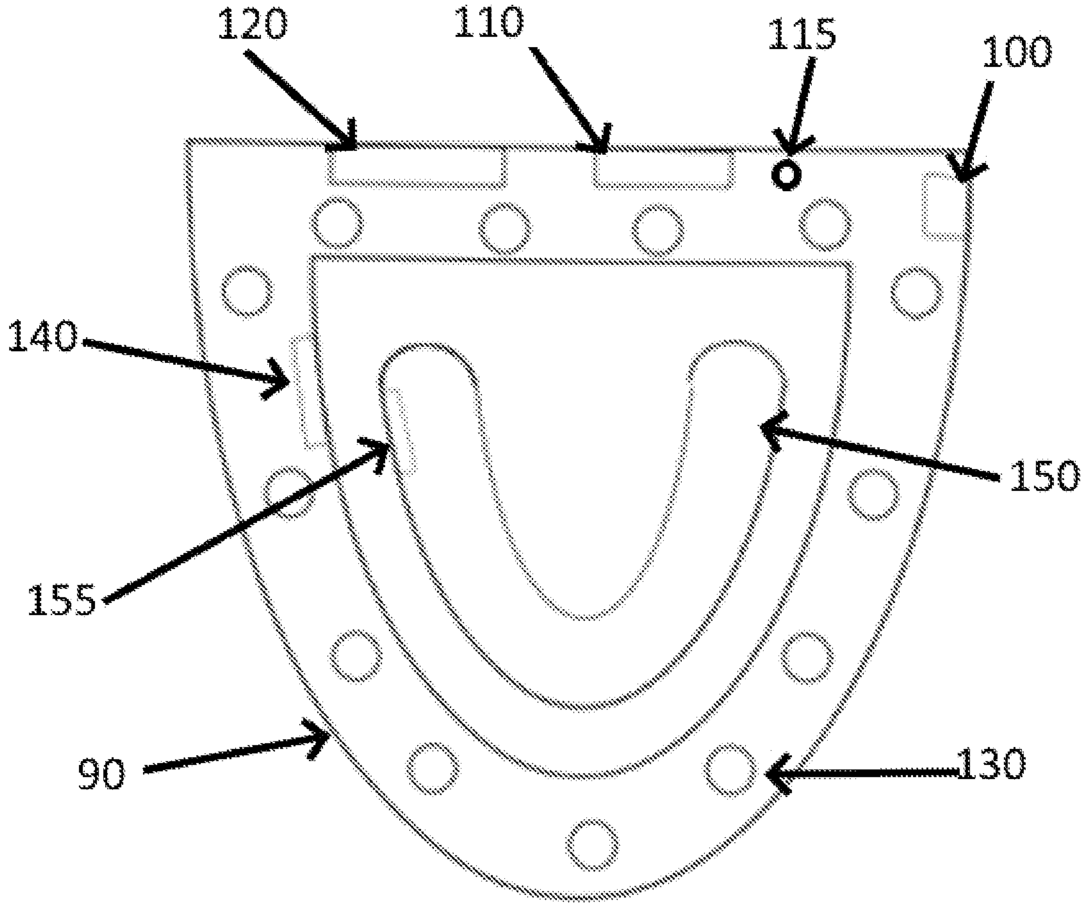
FIG. 9*a* is a partial perspective view of a charging station of the present invention.
Figure 9B:
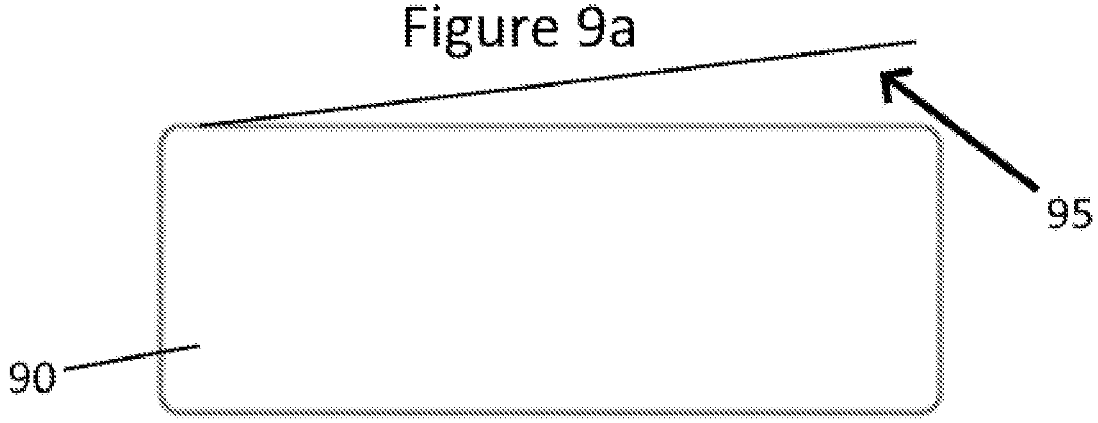
FIG. 9*b* is a side perspective view of the charging station of FIG. 9*a;*

In one embodiment the charger may also clean the mouthpiece, either actively or passively. Cleaning may be done with UV light, ultrasound, ionized air, a liquid cleaning solution such as those used for dentures, or other means. FIG. **9*a* shows a charger case 90. The charger case may have a battery 120 or be powered with RF, or powered through a charger cable plugged into an electric cable socket 100. The battery of the charger may also be charged via an RF coil 140. The same or a different RF coil 140 may then in turn charge the mouthpiece 150 through its RF charging coil 155, or through charging contacts. The battery 120 and the electric cable socket 100 may be connected to a circuit 110, which may complete the appropriate power conversion, and may communicate with a cell phone application via Bluetooth, and may have an on off switch, and may drive visual indicators 115 like an LED to indicate on off, or charging data, or other data, and the circuit may also turn on UV or similar lights 130 to clean and disinfect the mouthpiece 150. The charging case 90 may have a lid 95 as shown in FIG. 9*b***.

The charging case 90 on off switch may be mechanical, capacitive or similar, and may turn on and off depending on if the mouthpiece is present or not, and if the mouthpiece is fully charged or not.

Method of Use

Figure 19:
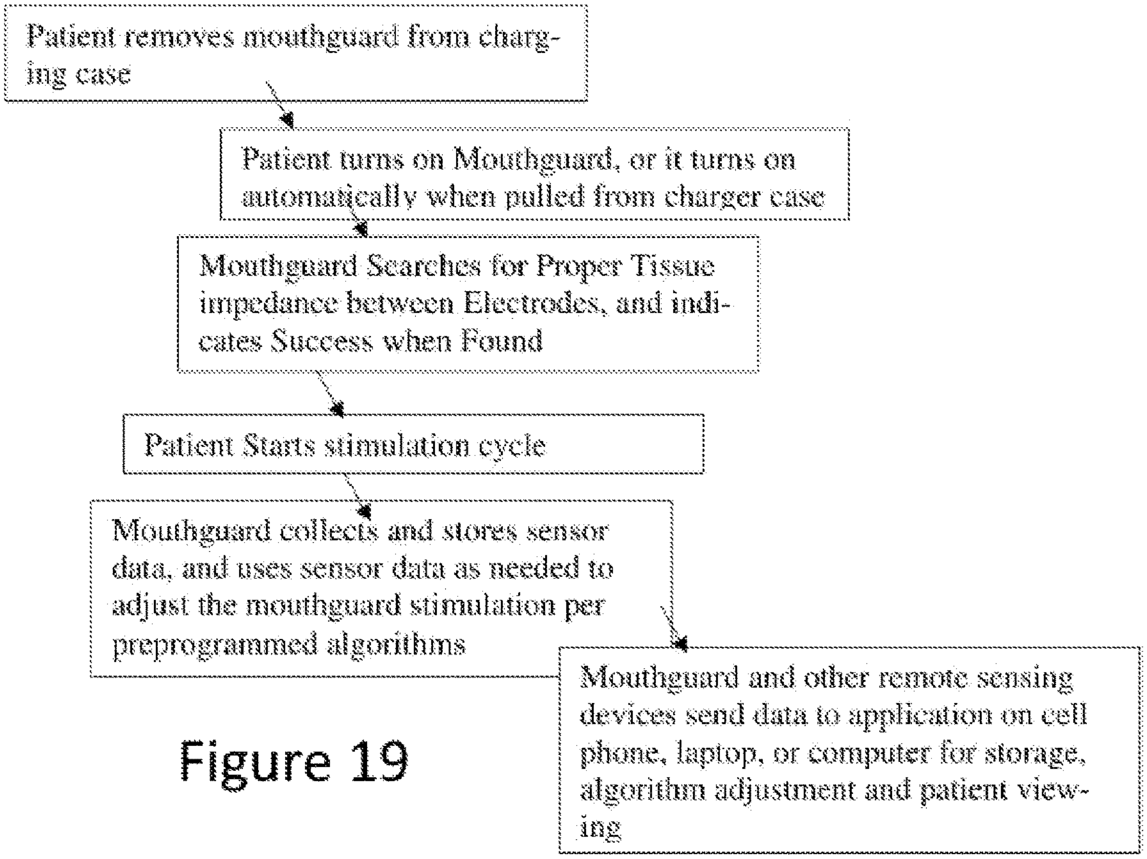
FIG. 19 is a flow chart of the method of using a stimulator system of the present invention.

In FIG. 19 a basic stimulation system use case is described. First, the patient removes the stimulator from the charger, after an indication that charging is sufficient. The patient then turns on the stimulator, unless it automatically turns on when it is removed from the charger. Next, the stimulator may go into a mode in which it senses for appropriate electrode to tissue impedance, after which the stimulation system may start a preselected stimulation algorithm or stimulation cycle. The stimulation system, and the stimulation digital application software on another device, may then collect and store sensed data, and also use the data to; inform the patient of the stimulation effectiveness, inform necessary adjustments to the stimulator output, and inform a pooled source to inform future improvements to any future product variable.

The stimulator or a connected device may measure tension in muscles, such as facial muscles. Lack of tension in those muscles may mean or like means that the patient is in deep sleep, which is an important input for appropriate stimulation algorithm adjustment. The connected device maybe, for example, a CPAP mask with a built in EMG or other means of measuring muscle activation or tension. It may also be a watch, or ring, clothing, bedding or similar measuring actigraphy or body movement.

Digital Application

Figure 26:
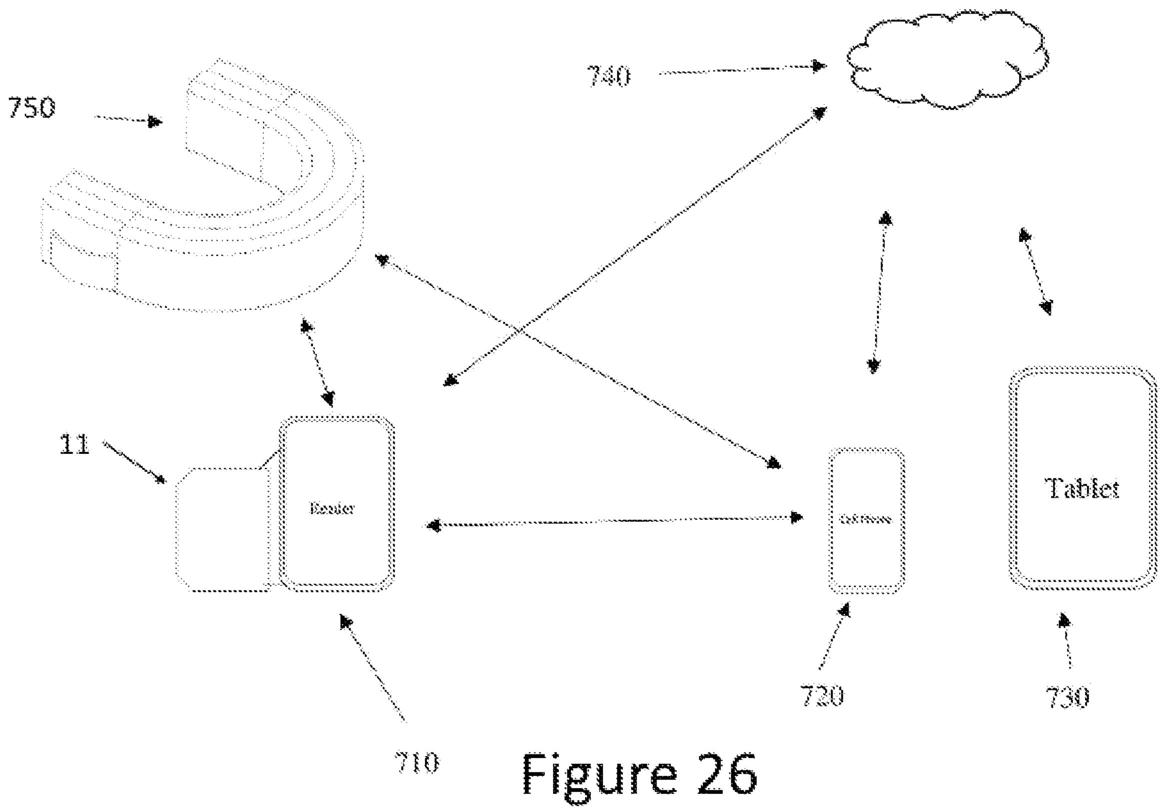
FIG. 26 is a block diagram of a stimulation system of the present invention.

A digital application for the stimulator 750, as in FIG. 26, may reside on the reader 710, a patient interface tool or a physician interface tool. The interface tool may be a computer, and digital pad 730, a smart phone 720, a smart watch, or similar device. The digital application software may be used as a patient interface, such that the patient may setup and adjust stimulation and sensing setting, upload data to the cloud, and communicate with physicians. The digital application software may also be used to collect patient reported outcome data to the cloud, for clinician monitoring. The patient data may include sleep data from a variety of sensors, patient sleep scoring data, patient cognitive test data, biomarker data, adherence data, electrode apposition data, device health data, and other typical patient data. The device containing the digital application software may connect directly to the stimulator or through another device, like a reader, using a wireless or wired connections. The digital application may access artificial intelligence or machine learning algorithms to support initial stimulator settings and to actively adjust those settings or prompt or recommended setting adjustments by the patient, care giver, or clinician. The digital application diagnostic capability may be acquired and used separately from the rest of the system. An example of this use would be by a patient who has a desire to understand or monitor their cognitive status, motor tremor level, sleep quality, speech tremor level, heart rate variability, or similar, as an input to understand the need or the effectiveness of the system in this invention, or other therapies, or combinations of therapies. The digital application software may have a variety of active or passive data collection inputs, both realtime and temporal changes, to facilitate a patient diagnosis, including; digital biomarkers (see Kourtis, L. C., Regele, O. B., Wright, J. M. et al. Digital biomarkers for Alzheimer's disease: the mobile/wearable devices opportunity. *npj Digital Med* 2, 9 (2019). https://doi.org/10.1038/s41746-019-0084-2), imaging biomarkers, data from cognitive tests, genetic test results, biofluid test results, patient movement data and changes in that data, patient communication data and changes in that data, eye movement data, sleep data, nervous system functional data, and neuropsychiatric data. The application software may use a single patient data to acutely suggest and improve its suggestion over time, when and what therapeutic solutions the patient may benefit from using. The acute and chronic suggestions may be improved if the machine learning techniques are used, and they may be improved even more if broader patient data sets are used within the machine learning algorithm. Active or passive sensors which may be collected directly or indirectly by sensors on part of the system, part of ancillary devices (smart watches, wrist bands, smart rings, smart phones, etc. . . . ) connected to parts of the system may include, social network algorithms, electromyography sensors, thermistors or thermometers, light sensors, accelerometers, global positioning sensors, EEG, ECG, impedance, touch screens, microphones, cameras, blood oxygenation, barometer, IMU, logic, PPG, galvanic sensors, force (stress/strain) sensors, actigraphy, acidity, etc. . . . .

Figure 21:
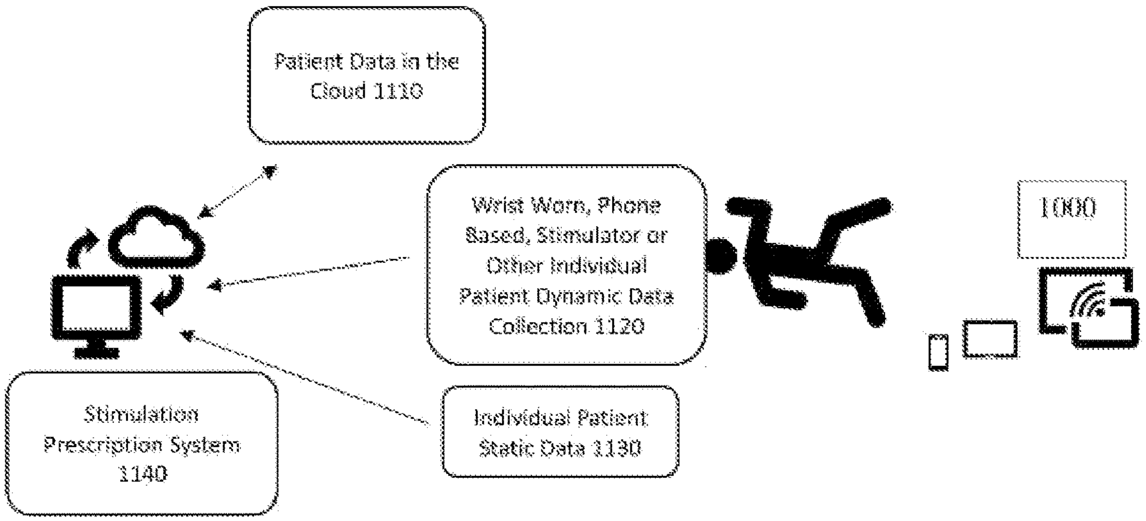
FIG. 21 is a block diagram of a machine learning system of the present invention.

Data analysis of stimulator output data, stimulator sensor data, patient imaging data, and or patient calibration data, may be used in machine learning techniques FIG. 21 to optimize short-term and long-term stimulator outputs and outcomes for specific patients or for groups of patients. Learnings from such analysis may be implemented in the form of software or firmware updates to the stimulator or an application controlling the stimulator, at time of initial fitment, at follow-up office visits, or through online updates through user applications. Realtime variable adjustments to the stimulator system can also be done through Bluetooth and or online connections to systems using machine learning techniques. The machine learning algorithms maybe included in the individual users application, and or it may be in the cloud, such that learnings may be pooled.

The predictive data model can include an artificial intelligence (AI) model or machine learning model. Various machine learning (ML) available from multiple providers which provide open-source ML datasets and tools to enable developers to design, train, validate, and deploy machine learning model, such as AI/ML processors. AI/ML processors (sometimes referred to as hardware accelerators (MLAs), or Neural Processing Units (NPUs)) can accelerate processing of MLMs. ML processors are integrated circuits (ASICs) that can have multi-core designs and employ precision processing with optimized dataflow architectures and memory use to accelerate calculation and increase computational throughput when processing machine learning models.

The machine learning model(s) may be stored as model files having a representational data format which describes the architecture of the model (e.g., input, output, and hidden layers, layer weights, nodes of each layer, interconnections between nodes of different layers, and ML operations of each node/layer) along with operating parameters and, thus, describe or represent a process flow between input and output layers of an machine learning model. After development, the machine learning model may be deployed in environments other than the environment or framework in which the model is initially trained. For example, distributing processing resources of a cloud system may train the machine learning models and distribute the trained machine learning model(s) to local digital devices a to implement.

In some examples, a machine learning model can be trained using known inputs and known outputs. The known inputs may comprise sensor signals indicative of HR, EEG, HRV, and other inputs including time of day, time zone, time of year, day of the week, sleep patterns, activity patterns, etc. The known inputs may be received from various sources, such as the stimulator, other sensors, external databases that store data from a plurality of stimulators and/or a digital application, among other sources. The machine learning model may be trained for a particular patient or a representative group of patients, and/or may be updated over time using feedback associated with the particular patient and/or the representative group of patients. The known outputs may comprise electrical outputs to test the electrical circuit, or electrical outputs to deliver nerve stimulation therapy (such as increasing CSF or blood flow), or electrical outputs to augment therapy (such as slow CSF flow for enhanced drug delivery), or direct non-stimulation therapy (such as drug delivery), or sensor outputs (such as IR light to sense blood oxygenation), but other outputs may also be included. Once the machine learning model is trained, currently inputs may be input to the trained machine learning model, which produces as output indicative of the stimulation to provide, e.g., the stimulation cycle output or other outputs such as the examples previously listed. Based on the output, the stimulation provided to the user is adjusted.

Regardless of where the stimulator is located or when it is used, there will be a need to optimize the output stimulation parameters, to optimize therapy and to minimize potential safety issues. Necessary stimulation parameters to optimize blood flow and CSF flow to and from the brain may be highly variable, depending on patient comorbidities, patient lifestyles, where the patient lives (latitude on earth or where in space), patient specific sleep patterns, patient specific day time activity, patient specific sleep disruptions, etc. . . . . The arterial lumen diameter pulsates throughout sleep, driven by the forms of pulsation previously mentioned. The perivascular space cross sectional area may increase and decrease in opposite directions to the arterial lumen diameter, such that when one increases the other decreases. During NREM sleep and light sleep arterial pulsations supply blood to the brain and also supplies CSF to the brain and mixes new CSF with ISF. During REM sleep there may be a further increase in arterial dilation, supplying more blood to the brain and pushing out the mixed CSF through the various CSF exit routes. Restoring this blood and CSF flow to natural or optimized levels may require a sophisticated algorithm with multiple input variables. For instance, only restoring a patients CSF flow back to their original flow levels may be what is actually optimal for that patient. To optimize for any specific patient, it may be important to consider specific patient data in the context of a broader patient pool, and what CSF flow levels work optimally for similar patients. Restoring a natural level of CSF flow for a specific patient might not equate to optimizing the flow for that patient. For any given patient there is likely a level of blood and CSF flow through the brain that is too low and a level that is too high. Optimizing initial parameters for each patient, prior to use, may start with initial patient intake information such as patient height, weight, and their previous sleep study information as examples. During use, the stimulator may have built in sensors which sense patient specific data such as heart rate or heart rate variability. Similar information can gathered from other devices the patient is using and are connected to the system (stimulator, reader, digital application or cloud) in this invention. The heart rate, or breathing rate, or other information, or a combination of these can be used to determine if the patient is sleeping and what sleep stage they are in. Stimulation may be used to help a patient fall asleep, or it may not start until a patient is asleep. Once asleep the stimulation pattern may be adjusted to optimal stimulation patterns specific for each sleep stage, such that the temporal patterning match as closely as possible optimal patterning for each patient. These sleep patterns may start with sleep cycle temporal patterns gathered from multiple patient sleep studies, including considerations from a patient's health records (co-morbidities, bio data, etc. . . . ), and combined with information from a broader patient pool. The temporal patterning can further be adjusted by data from onboard sensors or connected sensors, sensing realtime heart rate, respiratory rate, patient movement and slow wave vasomotion. The temporal patterning can be refined even further by adjustments to more closely match previous patterns which gave the patient the most rested feeling, either by self sleep scores or by data from a sleep study. This pattern may also be adjusted over time, by a machine learning algorithm or clinician inputs, based on data from a broader patient pool, or based on specific data from the patient. All of the above may be used as diagnostic information for clinicians and also for informing optimization of drug administration.

If the stimulator is used while awake, the stimulator may be adjusted to stimulate to optimize both day time brain function and clearance. For instance, different stimulation levels and patterns may be utilized in wake versus sleep use.

In one embodiment the digital application includes the means to share data, e.g., though the cloud, Bluetooth, Wi-Fi, peer to peer data connection, cellular network, radio, or a wired connection, between devices. As such, the patient or a provider can share the data with other caregivers, family members, providers, a social community or other outside entities. In one case the sharing is of select data, but in the case of multiple doctors collaborating to evaluate a patient, it may be advantageous to provide full access to the system and its data.

The digital application may provide an output to grade how successful the day's treatment was. Thus, the dashboard or an indicator on it can turn green/yellow/red based on the success of the day/night's treatment. Other indications are possible, and may be customized by the patient, to include backgrounds, images, colors, tones or music, meters, or graphs. It is also contemplated that the patient may have a graph or risk meter to see the risk of their treated condition based on any of the data items described herein. The system may also provide reminders to the patient to complete their sessions using any of the above.

With reference to FIG. 21, a wearable data collection device 1000 is worn by the patient, or is in close proximity. It collects dynamic individual patient data 1120. The data collection device 1000 may be a stimulator, wrist worn, e.g., a smart watch, a smart ring, in close proximity e.g., a smart phone, or more be a medical specific wearable akin to an EEG monitor, or be in a patients bedding e.g. a pillow, or sit on a table. It may also be a combination of modules, e.g., a smart watch, a smart ring, or EEG monitor that utilizes the smart phone for processing or communication with the stimulation prescription system and software 1140, which ideally uses both the individual patient data 1130 and cumulative or historical patient data 1110.

Wearable data collection device 1000 (FIG. 21) may seek to collect key data that is used to diagnose dementia. For example, wearable data collection device 1000 may collect blood pulse data and EEG data. To collect this data, the wearable data collection device may be a stimulator and include a blood pulse monitoring apparatus.

While the wearable data collection device 1000 may not be capable of gathering all of the data relevant to a dementia diagnosis, the physician, user, or stimulation prescription system and software 1140 may provide additional static data regarding the patient to the data collection device. In addition, the user may input additional data on the data collection device 1000, such as if the user had a head ache in the morning, noticed a medical issue such as mental fogginess, took a temperature, or the like. The wearable data collection device 1000 may also collect ambient data, such as temperature, humidity, smog, location, or other ambient information.

Data collection device 1000 may be used to continuously collect dynamically changing data from the user regarding the user's heart health. For example, data collection device 1000 may collect data regarding user heart rate, heart rate variability, pulse pressure wave morphology, and other features that may provide predictive value regarding the health of the user, and be used as patient input data before stimulation, during or after. Data collection device 1000 may also provide feedback, alerts, reminders, and other indications to patient that may encourage self-care and tell the patient and clinician if the stimulation parameters need to be adjusted up, down, or closed. The system may include a variety of data collection, data entry, data processing and data output equipment, such as body weight scales, EEG devices, implanted blood pressure sensors, exercise equipment, digital stethoscopes, and other devices (not shown) that provide an indication of one or more aspects of the health of patient. The output of data collection device may be transferred to wearable computing device, wrist worn dynamic sensor systems, additional computing devices, stimulation prescription system and software 1140 and/or cloud computing devices for analysis, including use in a predictive machine learning model for collecting static data, dynamic data, and pooled patient data, as discussed below.

The stimulation prescription system and software 1140 may allow for a clinician or data technician to input and view all patient static and dynamic data, run various scenarios, create adjustments to the machine learning algorithm (discussed below) prior to calculating optimal stimulation parameters, stimulation recommended range, and risks. The clinician may then use this data to prescribe stimulation parameter, device fitment, or device adjustments. Patient specific post procedure data collection can be used to update the quality of the patient pool data, which in turn may be used to update the software based machine learning model or algorithm for specifying general future patient stimulation parameters, or stimulation adjustments. The stimulation system may also be used to trend data such that intervention can be adopted prior to an irrecoverable medical situation. The wearable data collection device 1000 may include an algorithm such as a machine learning algorithm to identify when immediate intervention is warranted, and then utilize a communication means (discussed herein) to alert the user or a physician.

In some cases, the stimulation prescription system and software 1140 may identify patients that should be excluded from a stimulation prescription. For example, the software may identify that the patient has a high CSF pressure, and that increasing CSF flow is not beneficial. The software may also identify a situation where the patient will not get increased CSF flow from the stimulation. However, this is patient, diagnosis, and comorbidity specific, and as such the system 1140 is trained to identify how much higher for a specific patient with a specific diagnosis. Likewise, in some patients the relationship between changes in stimulation and increased CSF flow is not preferred. Thus, the system is also trained to identify the relationship that best indicates a stimulation.

Figure 22:
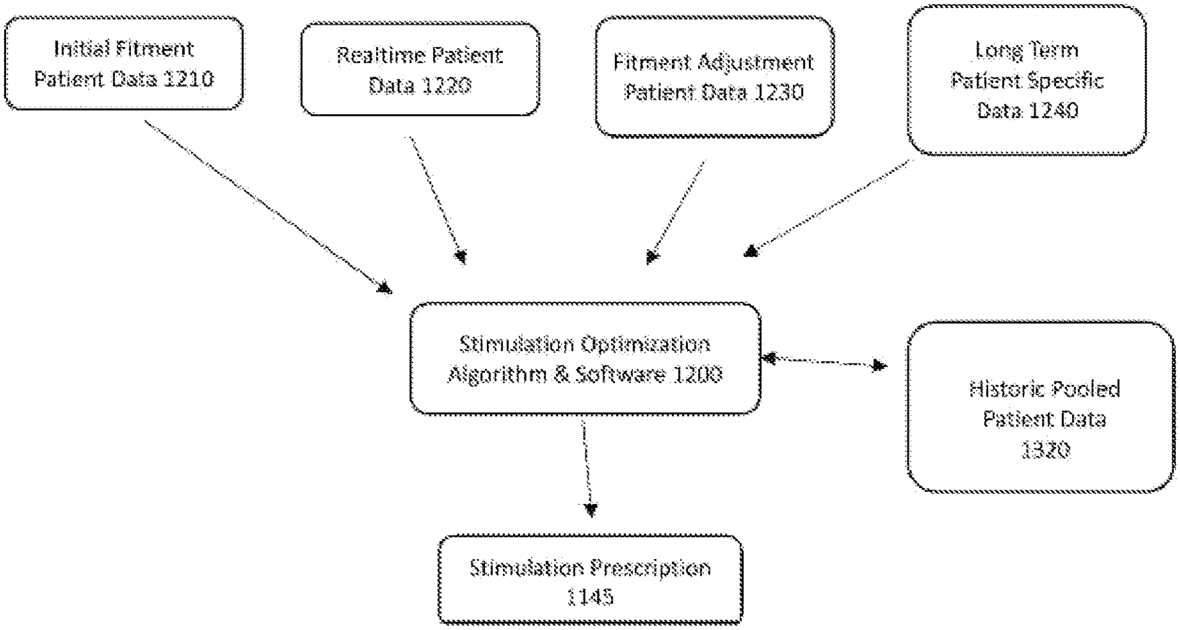
FIG. 22 is a block diagram of a machine learning system of the present invention.

With reference to FIGS. 21 and 22, stimulation prescription system 1140 and software 1200 includes several inputs and outputs. Patient initial fitment data 1210, realtime patient data 1220, patient fitment adjustment data 1230 and long term patient data 1240, both static and dynamic, as well as historic pooled patient data 1320 may all be inputs to define a stimulation prescription 1145. The historic data 1320 thus includes data gathered at different time points for each patient. It includes some, most, or preferably all of the input data types that would be included with data. While the initial data gathered would have a different time point than the realtime or historic data, it is also true that even with the initial data there may be multiple measurements at multiple times, even of the same test, e.g., multiple pulse measurements, multiple EEG tests, and the like.

The patient data inputs may include those described earlier, and may also include some or all of the data which was used to diagnose the heart failure and additional metrics, including, but not limited to, general laboratory data, electrocardiography data, ADAS Cogs test scores, other questionnaire scores (physical limitation score, symptom stability score, symptom frequency score, symptom burden score, brain metabolite scores, tests for misfolded proteins like beta amyloid and tau, total symptom score, self-efficacy score, quality of life score, social limitation score, overall summary score, and clinical summary score), HF hospitalizations, level of pulmonary congestion, a basic measurement of vital signs, EEG, electrocardiogram (ECG), an echocardiography and other imaging modalities to assess cardiac output, glucose levels, ventricular contraction and filling, atrial size, and cardiac valve function, etc., measurement of pulmonary capillary wedge pressure (PCWP), body weight, 6 minutes' walk test, body frame size, BMI, ECG data, demographic information, medications taken before, during, and after hospitalization, patient vital signs, patient lab results, patient weight change during hospitalization, echo-cardiogram results, comorbidities, blood pressure, blood tests to check for chemicals such as brain natriuretic peptide (BNP and Nterminal pro-B-type natriuretic peptide (NT-proBNP), a stress test, maximum systolic slope, systolic rise time, election time, dicrotic notch height, dicrotic notch timing, total pulse pressure, pulse arrival time, pulse transit time, heart rate, heart rate variability, pressure wave morphology, activity level, step count, sleep time, sleep quality, posture, reflected wave arrival time, cardiac catheterization and/or an MRI or CT scan.

The patient data may also include patient anatomical size, neurohormonal effects, drugs, stage of disease, chamber compliance, complicating comorbidities, and post procedure physiological remodeling. Other patient data may include amount of lung congestion, Creatinine (a chemical waste product of creatine, an amino acid, excreted in urine), Blood urea nitrogen (a waste product produced as a result of digestion of protein; an indicator of kidney function), Hemoglobin (a protein responsible for transporting oxygen in blood), White blood cell count, Plate-lets (a type of blood cell that helps form clots to stop bleeding), patient happiness score, Albumin (a liver-produced protein that helps keep fluid in the bloodstream and not leak into other tissues), Red blood cell distribution. Due to the complexity and number of these patient data input variables which need to go into calculating proper stimulation, and the interdependencies between them, an intelligent system is preferred to tailor stimulation for specific patients.

In one embodiment, the patient data inputs may also include all comorbidities which may potentially impact the prescription, either through direct impact, like hemodynamic flow reduction due to PAD, hypertension, small vessel disease, hardening of the arteries, or indirect variables from patient historic pool data which caused morbidity or mortality.

All of these input variables may be later also used as output variables. That is, in an advanced embodiment the software may predict how the variables may change after stimulation, as the patient ages, and the body remodels. In addition, in one embodiment the physician may input target values for one or more variables, and the software may provide options, e.g., stimulation and or medication, for achieving those values. The system may also identify additional information that would be valuable for the calculation, in the instant case, as well as variables that are suspect and should be re-measured.

The stimulation prescription 1145 output may include a binary output indicating if a patient may benefit from stimulation, what the possible risks are and their risk levels, the ideal stimulation range, and as noted above, the software may predict how all or many of the input variables may change after stimulation is done for a given period of time and the patient tissue and physiology remodels. After the initial stimulation further patient data input into the system can be used to monitor trends, correct recommendation on the stimulation, assess risk levels, and adjust predicted outcomes. Collectively these outputs, before, during and after stimulation may be included in a stimulation prescription 1145. The patient may have a means to collect and send input data to the stimulation prescription software in real time, and be able to get direct output in real time. Alternatively the output alarms could be set such the patient is not notified unless a certain alarm parameter is met.

Figure 23:
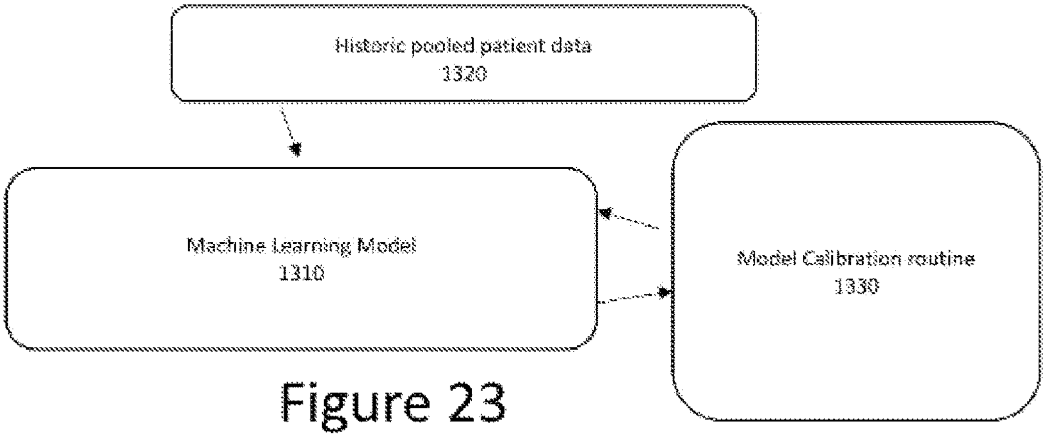
FIG. 23 is a block diagram of a machine learning system of the present invention.

As shown in FIG. 23, the machine learning system 1310 may include one or more computers or servers for data processing, storage, data retrieval, data input, and the like. In some implementations, medical data, such as data can be processed by a compiled binary or software executed with the system processor and the memory of the server, to provide a stimulation prescription. The binary or other software executed with the server may implement one or more machine learning models on the medical data, as discussed below. Typically, when the output is a desired stimulation or stimulation range, e.g., stimulation prescription, the model will use a supervised learning algorithm such as a neural network, deep neural network, support vector machine model, decision tree, random forest algorithm, extreme gradient boosting, or the k-nearest neighbor algorithm. With use of the learning model, the machine learning system is able to produce accurate and detailed stimulation prescription through a data-driven cycle of training, processing, and expert verification of results.

Using a prepared historical data set, the algorithm is trained to provide a stimulation prescription. In some examples, the trained detection algorithm may process historical pooled data inputs and one or more of current data inputs at different levels of the model. Alternatively, an unsupervised algorithm such as Apriori or K-means may be utilized to identify unknown or unappreciated factors in stimulation.

In one embodiment, the machine learning system produces data indications to identify future diagnostic or interventional efforts that would affect the stimulation prescription or efficacy. In some implementations, the machine learning system may establish descriptors, markings, annotations, or additional metadata, for data may indicate the presence of particular comorbidities or conditions, the absence of certain identified conditions, the likelihood/probability/or other certainty score of such identified conditions, and other related outputs from the operation of a recognition algorithm on the medical data.

Prior to the machine learning system receiving the data, the data should be prepared for use in the system. In particular, data gathered from many different devices (such as numerous different types of EEG machines), will need to be standardized, or may be limited to particular sources. Alternatively, the data can be entered with an indication of the source for the algorithm to differentiate between different data sources. The more detailed the metadata for a particular datum, the broader the applicability of the developed model. However, it will be more difficult to train the model. Accordingly, while a large historical data set may be preferred, a more homogenous data set enables quicker training. In one embodiment the invention uses a real time model of the cerebral or glymphatic system to generate data to train the machine learning system. This data model is then phased out as actual patient data is generated.

When the system receives data it will process the data for further handling in the workflow. This processing may include converting the data to a different format, standardizing the data, or rejecting the data. The machine learning system may also operate to extract metadata from each data file. For example, the extracted metadata may include header data providing patient information and medical facility information for the facility that gathered the data. The machine learning system may then store all or part of the extracted information in a study record that may be correlated with other like data.

A machine learning model within the stimulation prescription software and learning model may be initially trained by all or a subset of historic pooled patient data. After the data is input into the machine learning model the output can be compared to expected or known outputs in a model calibration routine 1330, which feeds weight and bias adjustments back into the machine learning model, via back propagation, regression, co-adaptation or similar. A model performance assessment may be done on a variety of machine learning models, such as random forest, gradient boosting, support vector machine, logic regression, logic regression with lasso. Patient specific models of the clearance systems based on imaging data may be used to optimize stimulation parameters to interact with specific points of intervention (CSF production, AQP4 channels, pulsatility, respiratory/heart rate).

Then the model which seems the most accurate for the given set of data and variables may be selected for utilization. Data samples from the pool may be initially be sorted into critical and non-critical, based on which input variable ranges have the greatest impact on the output variable ranges. As an example, patient frame size is likely to be a significant predictor of necessary stimulation. So it is optimal to sort and use training data which covers the broadest possible range of patient frame sizes. Also, it will be important that the training data include both those patients who have had optimal results from their stimulation, from improved ADAS Cog's scores, improved mental clarity, lower hospitalization rates, etc. and from those patients who have had the worst follow-up results, such that the model is trained to not prescribe stimulation prescriptions which will potentially give poor results. The data samples used for model training include all variables, and ideally the full range of critical variable data.

Applicants have identified EEG results, ADAS Cog's testing, and misfolded protein load, as critical variables for understand stimulation needs and potential benefits. As a result, the data used should include this information, and similar information, and it should be more heavily weighted in the software.

Figure 24:
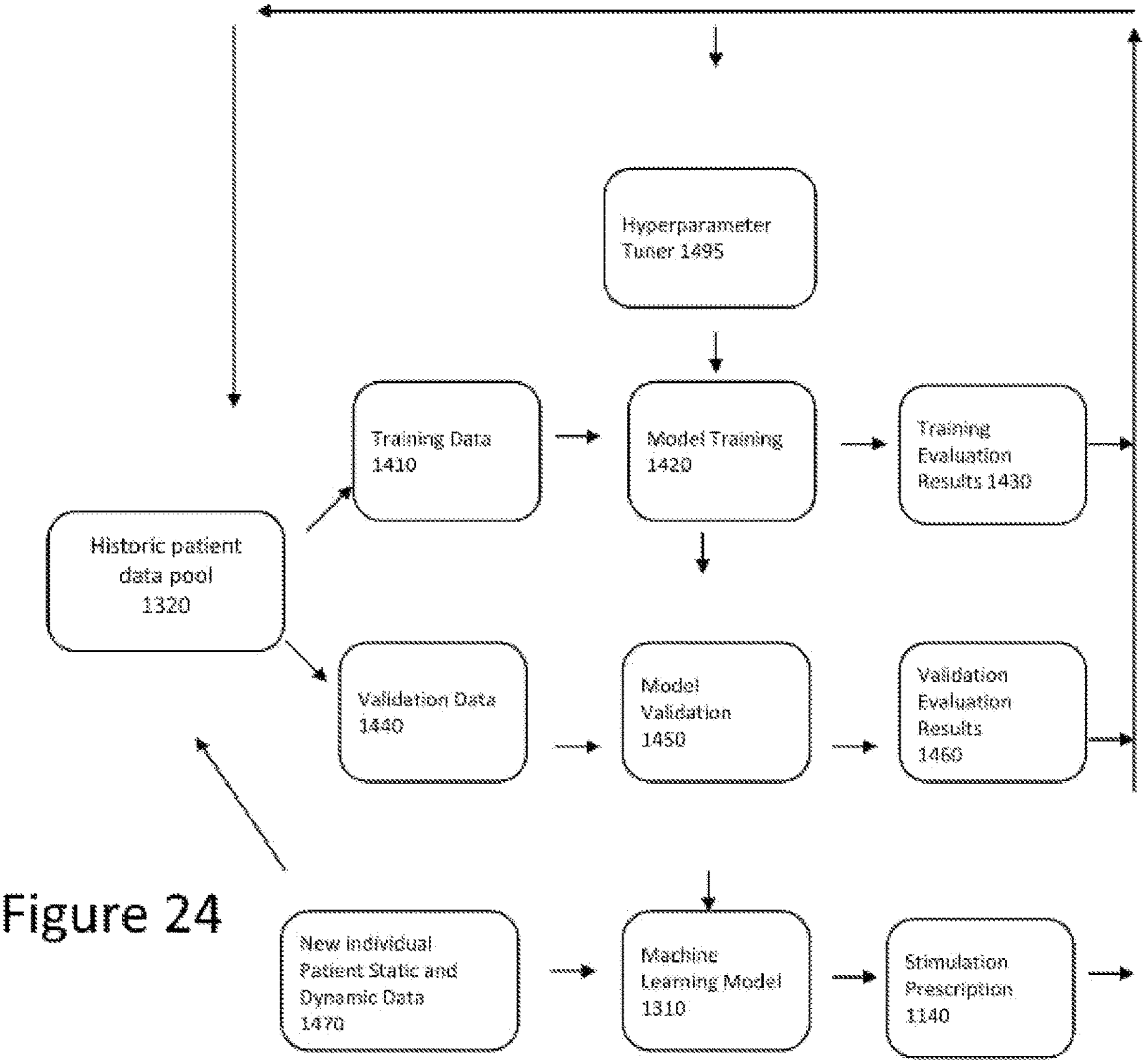
FIG. 24 is a block diagram of a machine learning system of the present invention.
Figure 25:
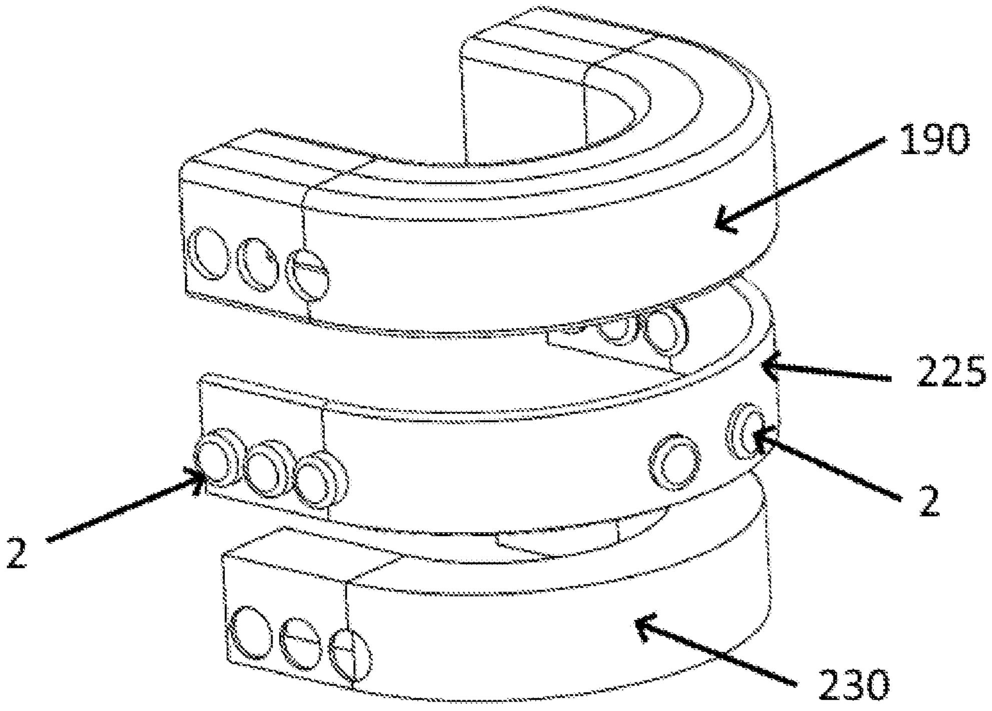
FIG. 25 is an exploded partial perspective view of a mouthpiece of the present invention.

FIG. 24 shows a more detailed model for training, validating, and commercial implementation for continuously updating a machine learning model 1310 within the software. A training data subset 1410 is pulled from the historical patient pooled data set 1320. In one embodiment the training data is 75% of the pooled data set 1320. In another embodiment it is 60%. After the data is curated, training data 1410 is fed into the model for model training 1420, resulting in training evaluation results 1430. In particular, the critical variables identified above are given an increased weight in the model. These results may be run through multiple models or algorithms 1310, depending on the results. The model 1310 may be adjusted based on the training evaluation results 1430. Likewise, the data may be tuned, added too, or reduced based on the results 1430.

These training evaluation results 1430 are typically fed into a hyperparameter tuner 1495 to adjust the model, in a preferred embodiment using Bayesian optimization. However, if the results match measured results then they may also be fed back into the patient data pool 1320 as calculated results. Similarly a validation data subset 1440 of historical patient pooled data set 1320 is used for model validation 1450. In one embodiment the validation data is 25% of the pooled data set 1320. In another embodiment there are two validation cohorts of 20% each. In a similar manner to training data 1410, the validation evaluation results 1460 may be fed into either the hyperparameter tuner 1495 or the pooled patient data 1320 or both. Once validated, new patient data 1470 may then be fed into the prescription software 1200 and the machine learning model 310. The software 1200 and/or model 1310 calculate a prescription 1140. The prescription 1260 can be fed into the hyperparameter tuner 1495 to continue model training, and into the historic patient data pool 1320.

In this way the software helps the machine learning model to continuously learn. FIG. 24 shows how a model may continue to learn from each individual patient dataset even after initial calibration from pooled data sets, by use of continued back propagation routines, to adjust weighting and bias. In particular, the critical variables identified above are given an increased weight in the model. Likewise, data generated outside the model and the specific patients can be pooled and fed into the model 1310.

Initially the model 1310 is trained by historic pooled patient input and output data 1320, simulated patient data, or both. The accuracy of model 1310's output—prescription 1140 or an identification of unknown or unappreciated factors in stimulation—will depend greatly on the quantity and quality of the historical pooled data 1320. Data preparation includes several steps. First off, all applicable regulations, privacy rules, and ethical rules must be observed before the data may be used. Often the data must be cleaned of certain identifying information. The data must then be reviewed for quality control, curated, structured, and expertly labeled, as well as consistently labeled. With reference to FIG. 5A, a medical provider 1600 will gather relevant local patient data 1610. Local patient data may be in a standardized format, such as an electronic health record (EHR) Likewise, the system may require that data be in a standardized EHR format. Local data 1610 is then provided to a central data storage 1620. Data technicians may ensure that the data is properly labeled, curated, and complies with all regulations either prior to transmittal from provider 1600, or at the centralized data storage facility. Alternatively, the data can be cleaned during model development, or the data 1610 may be partially cleaned and/or curated locally and partially at a centralized setting.

Once the data has been properly cleaned by removing or modifying data that is incorrect, incomplete, irrelevant, duplicated, or improperly formatted it will be utilized in training the model. Likewise, during training the data technician may employ dimensionality reduction to remove data nodes that are redundant to other data, or to combine nodes. In an optional step the data technician will seek to create visualizations, tests, or relationship matrices for the data and its relationship to stimulation. Expertly identifying the key data components as discussed above and their relationship to stimulation will assist in model training.

A first set of new patient data in the form of static and dynamic preprocedural data 1210 is received for a user, fed into the machine learning software 1200, and one or more prescriptions 1140 are generated by a machine-learning model based on the set of data.

Clinical or cloud computing is used in aggregate, subset, single institutional form, or single clinician form to train the machine learning model 1310. In aggregate, a single patient pool of data 1320 is collected and shared between clinical sites, which allow for a broader data set to more properly adjust the algorithm via machine learning. However, there are situations where a clinician or clinic may only want data from a single institution, individual clinician, or individual patient. In addition, the system may favor data from a particular physician or institution in providing a result for further procedures from that physician, institution, or another location. Accordingly, in data training the system 1300 allows the data technician to give greater weight to data from a particular source in training the system, or to train the system 1300 using data from a particular source.

The amount of data utilized for the training set may determine which learning algorithm or model 1310 is utilized. For a large amount of data, a deep neural net training model is preferred by the inventors. Due to the large number of input characteristics, or features, the neural network has a large number of input neurons. As a result, the neural network may also have a very large number of hidden layers, each with its own parameters, before passing to the output layer. As information passes through the neurons, or nodes, it is weighted by expert input and model training as to the key information identified above. During training the data scientist will use back propagation, feeding the prediction errors back through the network modifying the weights of each neural connection until the error level is minimized. However, a deep neural network can overfit the data 13 due to the excessive number of layers, and as such some of the historical pool data must be not be used for training, and can only be used for validation to relax the overfit. That is, the first time the model sees this validation data 1440 is in validation. At present the inventors' preferred deep leaning technique is performed on a very powerful computer enhanced with GPU(s) rather than the handheld's disclosed herein due to the computer power requirements of a deep neural network. However, a handheld may be preferred for calculating a stimulation prescription and post operative stimulation monitoring to identify complications.

In the event that the system 1300 is to be employed solely within one clinic, or for one physician, the limited data subset gives preference to a support vector machine model 1310. If the model is to be formed quickly for a new patient, the support vector machine model may be faster to train, and may be more readily trained in a limited computing or time environment. Generally a supervised learning model like a supervised neural net or a SVM requires data with accurate labels for training.

A machine-learning training pool patient data set for calibrating the machine learning model within the software, within the system may be split into D and S data sets which respectively represent historic pooled dynamic data 1320 and static data 1470. The pooled data is initially input into a single classifier or regressor for stimulation calculation. The classifier sorts for optimized follow up data, based on initial data and prescription. To make sure that the machine learning model is not too tightly fit to an unwanted subset, the feature selection and regularization ideally include pooled data sets from multiple institutions, multiple physicians and multiple patient types (various comorbidities).

The static and dynamic pooled training data is fed into a single classifier or regressor in the model, to calculate patient suitability for a prescription. The dynamic and static data, can also be fed into separate classifiers. Also, dynamic data can be used to update static data and then be fed into a single static classifier. Classifiers may be adjusted based on dynamic data, medication or other variables. The data can combine features or keep them separate. For example, similar comorbidities might be combined. Also, separating data for initial training may help to calibrate the model more efficiently with less data. The best set of input variable features and weights can be determined manually by the clinician or by the machine learning model.

Due to the large number of both dynamic and static input variables, it is ideal that a deep neural net training model be used, though other training models may also work as well or better. A first model is trained by the historic data and has nodes in a penultimate layer which are trained to be predictive of the known stimulation which gave the best related patient outcomes from the stimulation. The model only needs to be trained once with the historical data, then later training can be done patient by patient as follow-up output data is available, or the new output data can be added to the historical patient pool and the model retrained on a periodic basis or once a specified number of new patients have been added to the pool.

After a patient receives stimulation the software can preferentially weight new data from the patient's new inputs to adjust its outputs to more closely align with the patient's specific details. The software may be set to increase input variable weighting for each new input.

In this way the model may be trained to learn a specific patient or subset of patients. Multilevel models may be used, such that once the classifiers and models are trained patient specific preprocedural data is entered into an intermediate model. The intermediate output values from the intermediate model are then concatenated with the dynamic procedural variables as available to form the feature vector for the final model and prescription. Later, in a similar way another concatenation may be done with post procedural patient data such that a new prescription could include a stimulation adjustment or other medical prescriptions. Deep neural net training models may also be used. In this way brain and whole body remodeling may be accounted for.

That is to say one intermediate or final model layer may be to account for remodeling, or remodeling may be accounted for in a single main model, or a completely separate model may be used for post stimulation patients. For specific patients, the program or software may be configured in a way which the machine-learning model is taught based on the patient's static data only, or combined with historical data from a large patient data pool. This data may then be used with future dynamic patient specific data to update the model on an ongoing basis. Specific classifiers may be used on new patient data to determine prescriptions. Training classifiers and models with only patient specific data may be useful in limiting the impact the multitude of important variables certain to be left out of the model. However, patient specific classifier and model training can only occur after the initial prescription is created and post procedure data collected.

Training dynamic data classifiers may include dampener algorithms to account for medications typically given to patients (e.g., rate limiters, diuretics, vasodilators) which have a significant acute effect that can be observed within dynamic data. Also for specific patients a machine learning model similar to the one used for determining the prescription may also be used to track the patients progress post stimulation, from seconds to decades after. The model may prescribe adjustment of the prescriptions.

After either in the initial training or the validation, the parameters are tuned. Thus, the number of training steps, the learning rate, and the initialization values, and the distribution can be adjusted to improve the model. This is an iterative process.

Dynamic data collection may be via wearable physiological monitoring devices, computers, phones, tablets, catheters, voice interface devices, implantable devices, etc., with sensors such as microphones, visible-light sensors, ultraviolet sensors temperature sensors, pressure transducing device, electrodes, a contact sensor module—EKG measuring cardiac pressure sensors, motion sensors, accelerometer, gyroscope, and magnetometer, GPS, electromagnetic guidance systems. All of these are used to measure the patient's blood-oxygen level, pulse, blood glucose levels, or other biometric markers with optical signatures, EEG, ADAS Cogs test, ECG, augmentation index, maximum systolic slope, systolic rise time, ejection time, dicrotic notch height, dicrotic notch timing, total pulse pressure, reflected wave arrival time, activity level, step count, sleep time, sleep quality, posture, etc. The data may be used to adjust an active stimulation system in real time.

The machine learning model may be in any program in any computing device(s) such as desk top or laptop computer, a tablet, a phone, a watch, in the cloud, or on an institutional server. There may be a plurality of models running in parallel or series. The patient pool data may be on a computing device or in the cloud, in RAM, optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.). Information may be displayed on monitors with light emitting diode (LED) array, a liquid-crystal display (LCD) array, (LCOS) array) may, active-matrix organic light-emitting diode (AMOLED) displays or quantum dot displays. Data may be transferred with two-way Bluetooth, cellular, near-field communication and/or other radios. In some implementations, communication suite may include an additional transceiver for optical (e.g., infrared) communication.

What is claimed is:

1. A stimulation system for changing cerebral spinal fluid flow rates through the brain comprising:

a stimulator, the stimulator comprising a first electrode positioned and designed to stimulate a cranial nerve by creating a stimulator output;

the stimulator further comprising a stimulator circuit and configured to generate temporally patterned electrical stimulation; wherein the stimulator output is configured to modulate cerebral spinal fluid flow in the brain;

a modulator system designed to provide the temporally patterned electrical stimulation to the first electrode;

a power controller designed to control the power of the stimulation wave to the first electrode and configured to control current amplitude between 100 microamps and 40 milliamps;

a communications module integrated with the stimulator;

an arterial pulsatility sensor;

wherein the temporally patterned stimulation is configured to enhance cerebral arterial pulsatility to increase cerebrospinal fluid penetration into brain tissue and enhance glymphatic clearance.

2. The stimulation system of claim 1, wherein the stimulator further comprises a second electrode, and wherein the stimulation system is configured to provide the stimulation wave to the electrode and a second, different stimulation wave to the second electrode.

3. The stimulation system of claim 1, wherein the stimulator further comprises a second electrode, and wherein the stimulation system is configured to automatically determine which electrode to stimulate.

4. The stimulation system of claim 1, wherein the power controller is configured to control the voltage and the current to the electrode.

5. The stimulation system of claim 1, wherein the temporally patterned electrical stimulation is a temporally patterned short higher frequency burst.

6. The stimulation system of claim 5, wherein the stimulator output is output to a first location and in a first pattern, the first location and the first pattern is configured to cause pulsations of cerebral vessel dilation and contraction.

7. The stimulation system of claim 1, wherein the stimulator output is output to a first location and in a first pattern, the first location and the first pattern is configured to open APQ4 channels.

8. The stimulation system of claim 1, wherein the stimulation wave is configured to increase the distance between neuronal/non-neuronal cells to allow more flow around these cells.

9. The stimulation system of claim 1, wherein the temporally patterned electrical stimulation is configured to increase phagocytic activity in glial cells.

10. The stimulation system of claim 1, wherein the temporally patterned electrical stimulation is configured to reduce central sympathetic tone.

11. The stimulation system of claim 1, wherein the temporally patterned electrical stimulation has a predetermined periodicity providing a first period of stimulation of the perivascular system and a second period of relaxation of the perivascular system.

12. The stimulation system of claim 1, wherein the stimulator further comprises a sleep sensor.

13. The stimulation system of claim 1, wherein the stimulator further comprises a respiratory sensor.

14. The stimulation system of claim 1, wherein the arterial pulsatility sensor is selected from the group consisting of EEG, MRI, CT Scan, x-ray, diffuse optical imaging, magnetoencephalography, PET, single photon emission computed tomography, and wherein the arterial pulsatility sensor has a sensor output, the system further comprising a processor, the processor configured to convert the sensor output into a cerebral spinal fluid flow measurement.

15. The stimulation system of claim 1, wherein the arterial pulsatility sensor is an IR light sensor, the IR light sensor configured to sense blood oxygenation.

16. The stimulation system of claim 1, wherein the arterial pulsatility sensor comprises a blood volume or a blood oxygenation sensor that indirectly measures cerebral spinal fluid flow.

17. A stimulation system for changing cerebral spinal fluid flow rates through the brain comprising:

a stimulator, the stimulator comprising a first electrode designed to stimulate a cranial nerve by creating a stimulator output; wherein the stimulator output is configured to modulate cerebral spinal fluid flow in the brain;

a modulator designed to provide a stimulation wave form to the stimulator;

a power controller designed to control the power of the stimulation wave to the stimulator;

a communications module designed to receive instructions executable by one of the stimulator, the modulator system, or the power controller to change the stimulation wave;

a vasomotion sensor.

18. A stimulation method for changing cerebral spinal fluid flow rates through the brain, comprising:

creating a stimulator output; wherein the stimulator output is configured to modulate cerebral spinal fluid flow in the brain;

stimulating a nerve with the stimulator output;

modulating the cerebral spinal fluid flow in the brain;

modulating the stimulation;

controlling the power of the stimulation;

communicating stimulation instructions between a remote device and the stimulator;

a stimulator, the stimulator comprising a first electrode designed to stimulate a cranial nerve by creating a stimulator output; wherein the stimulator output is configured to modulate cerebral spinal fluid flow in the brain;

a modulator system designed to provide a stimulation wave to the first electrode;

a power controller designed to control the power of the stimulation wave to the first electrode;

a communications module designed to receive instructions executable by one of the stimulator, the modulator system, or the power controller to change the stimulation wave;

a remote device comprising;

a processor;

a memory coupled to the processor, the memory comprising computer readable instructions executable by the processor, the processor operable when executing the instructions to send instructions to the communications module to change the stimulation wave.

* * * * *